United States Patent [19]
Fischer et al.

[11] Patent Number: 5,808,135
[45] Date of Patent: Sep. 15, 1998

[54] 2-(2,4,6-TRIMETHYL PHENYL) CYCLOPENTANE-1,3-DIONE DERIVATIVES

[75] Inventors: Reiner Fischer, Monheim, Germany; Jacques Dumas, Orange, Conn.; Thomas Bretschneider, Lohmar, Germany; Christoph Erdelen, Leichlingen, Germany; Ulrike Wachendorff-Neumann, Neuwied, Germany; Hans-Joachim Santel, Leverkusen, Germany; Markus Dollinger, Leverkusen, Germany; Andreas Turberg, Erkrath, Germany; Norbert Mencke, Leverkusen, Germany

[73] Assignee: Bayer Aktiengesellschaft, Leverkusen, Germany

[21] Appl. No.: 765,917

[22] PCT Filed: Jul. 11, 1995

[86] PCT No.: PCT/EP95/02684

§ 371 Date: Jan. 15, 1997

§ 102(e) Date: Jan. 15, 1997

[87] PCT Pub. No.: WO96/03366

PCT Pub. Date: Feb. 8, 1996

[30] Foreign Application Priority Data

Jul. 21, 1994 [DE] Germany ............................ 44 25 953.0
Jan. 31, 1995 [DE] Germany ........................ 195 92 945.3
Jun. 13, 1995 [DE] Germany ........................ 195 21 430.7

[51] Int. Cl.$^6$ ......................... C07C 69/00; C07C 315/00; A01N 37/12; A01N 31/06
[52] U.S. Cl. ......................... 560/129; 568/327; 564/263; 564/250; 564/180; 558/214; 504/313; 504/348; 504/344; 504/343; 504/336; 504/290; 504/295; 504/194; 549/39; 549/453
[58] Field of Search ................................... 560/256, 129; 568/327; 504/348, 344, 343, 336, 290, 295, 313, 194; 549/39, 453; 564/263, 250, 180; 558/214

[56] References Cited

U.S. PATENT DOCUMENTS 4,283,348 8/1981 Wheeler .................................. 568/327
4,436,666 3/1984 Wheeler .................................. 568/327

Primary Examiner—Deborah C. Lambkin
Attorney, Agent, or Firm—Sprung Kramer Schaefer & Briscoe

[57] ABSTRACT

The present invention relates to novel substituted bicyclic 2-mesityl-cyclopentane-1,3-dione derivatives of the formula (I)

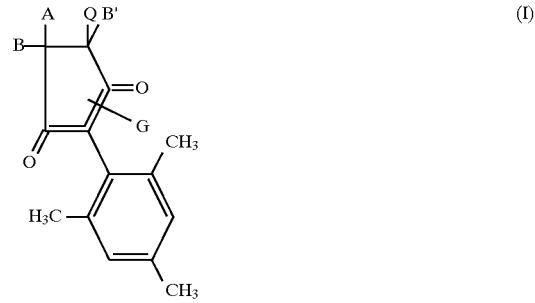

in which

A and Q together represent alkanediyl or alkenediyl, which is in each case optionally substituted by halogen, hydroxyl, mercapto or in each case optionally substituted alkyl, alkoxy, alkylthio, cycloalkyl, benzyloxy or aryl, and which furthermore optionally contains one of the following groups

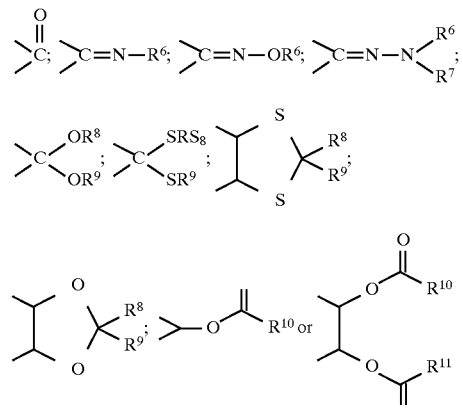

or is bridged by an alkanediyl group
and B, B' and G have the meaning given in the description, process for their preparation and their use as agents for controlling pests, and herbicides.

6 Claims, No Drawings

2-(2,4,6-TRIMETHYL PHENYL) CYCLOPENTANE-1,3-DIONE DERIVATIVES

This application is a 371 of PCT/EP95/02684 filed Jul. 11, 1995.

The present invention relates to novel 2-aryl-3-hydroxy-$\Delta^2$-cyclopenten-1-one derivatives, processes for their preparation and their use as herbicides and agents for controlling pests.

It is known that certain substituted 2-arylcyclopentanediones, such as, for example, 2-(2',4'-dimethylphenyl)-4,5,6,7,8,9-hexahydro-1,3-indanedione, have herbicidal and acaricidal properties (cf., for example, U.S. Pat. Nos. 4,283,348; 4,338,122; 4,436,666; 4,526,723; 4,551,547 and 4,626,698). 2-(2,4,6-trimethylphenyl)-1,3-indanedione is furthermore known from the publication J. Economic Entomology, 66, (1973), 584 and the laid-open specification DE 2 361 084, with mention of herbicidal and acaricidal actions.

However, the activity of these known compounds is not completely satisfactory in all fields of use, especially when low amounts and concentrations are applied.

Novel substituted bicyclic 2-mesityl-cyclopentane-1,3-dione derivatives of the formula (I)

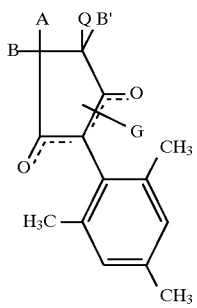

in which
A and Q together represent alkanediyl or alkenediyl, which is in each case optionally substituted by halogen, hydroxyl, mercapto or in each case optionally substituted alkyl, alkoxy, alkylthio, cycloalkyl, benzyloxy or aryl, and which furthermore optionally contains one of the following groups

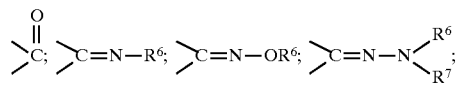

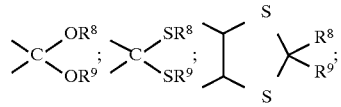

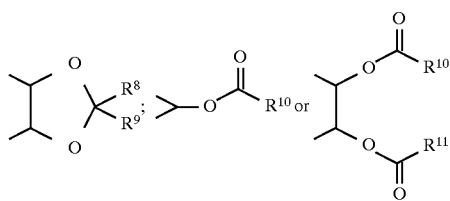

or is bridged by an alkanediyl group,
B and B' independently of one another represent hydrogen, halogen or alkyl, or together represent in each case optionally substituted alkanediyl or alkenediyl, G represents hydrogen (a), or represents one of the groups

 (b)

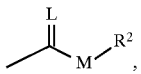 (c)

 (d)

 (e)

E (f)

or

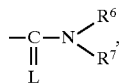 (g)

in which
E represents a metal ion equivalent or an ammonium ion,
L represents oxygen or sulphur and
M represents oxygen or sulphur,
$R^1$ represents in each case optionally substituted alkyl, alkenyl, alkoxyalkyl, alkylthioalkyl, polyalkoxyalkyl or cycloalkyl, which can contain at least one heteroatom, or in each case optionally substituted phenyl, phenylalkyl, hetaryl, phenoxyalkyl or hetaryloxyalkyl,
$R^2$ represents in each case optionally substituted alkyl, cycloalkyl, alkenyl, alkoxyalkyl or polyalkoxyalkyl, or in each case optionally substituted phenyl or benzyl,
$R^3$ represents in each case optionally substituted alkyl, phenyl or phenylalkyl,
$R^4$ and $R^5$ independently of one another represent in each case optionally halogen-substituted alkyl, alkoxy, alkylamino, dialkyl amino, alkylthio, alkenylthio, cycloalkylthio, or represent in each case optionally substituted phenyl, phenoxy or phenylthio,
$R^6$ represents hydrogen or in each case optionally halogen-substituted alkyl, alkenyl or alkoxyalkyl, or represents optionally substituted phenyl, or represents in each case optionally substituted cycloalkyl or benzyl,
$R^7$ represents hydrogen or in each case optionally halogen-substituted alkyl or alkenyl, or
$R^6$ and $R^7$, together with the N atom to which they are bonded, represent a ring which optionally contains oxygen or sulphur,
$R^8$ and $R^9$ independently of one another represent hydrogen or in each case optionally substituted alkyl, phenyl or phenylalkyl, or together represent an optionally substituted alkanediyl radical and
$R^{10}$ and $R^{11}$ independently of one another represent in each case optionally halogen-substituted alkyl, alkenyl, alkoxy, alkylamino, dialkylamino, alkenylamino or dialkenylamino or in each case optionally substituted phenyl or benzyl, have now been found.

Depending on a position of the substituent G, the compounds of the formula (I) can be present in the two isomeric forms of the formulae (I-A) and (I-B), which the broken line in the formula (I) is intended to illustrate:

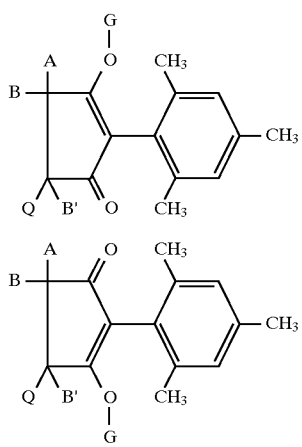

The compounds of the formula (I-A) and (I-B) can be present both as mixtures and in the form of their pure isomers. If appropriate, mixtures of the compounds of the formulae (I-A) and (I-B) can be separated by physical methods, for example by chromatographic methods.

For better clarity, in each case only one of the possible isomers is shown below. This does not mean that the compound in question cannot be present, where appropriate, as an isomer mixture or in the other particular isomeric form.

Incorporating the various meanings (a), (b), (c), (d), (e), (f) and (g) of group G, the following main structures (Ia) to (Ig) result:

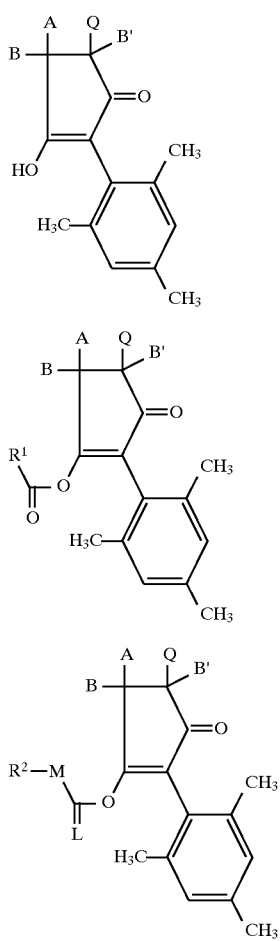

wherein

A, B, B', E, L, M, Q, $R^1$, $R^2$, $R^3$, $R^4$, $R^5$, $R^6$ and $R^7$ have the abovementioned meanings.

Because of one or more chirality centres, the compounds of the formula (Ia)–(Ig) are in general obtained as a stereoisomer mixture. They can be present and used both in the form of their diastereomer mixtures and as pure diastereomers or enantiomers.

It has furthermore been found that the novel substituted 2-mesityl-cyclopentane-1,3-dione derivatives of the formula (I) are obtained by one of the processes described below.

(A) 2-Mesityl-cyclopentane-1,3-diones and enols thereof, of the formula (Ia)

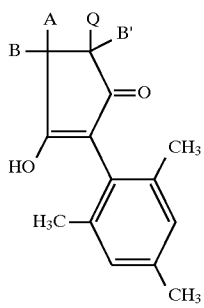
(Ia)

in which

A, B, B' and Q have the abovementioned meaning, are obtained when 5-aryl-4-keto-valeric acid esters of the formula (II)

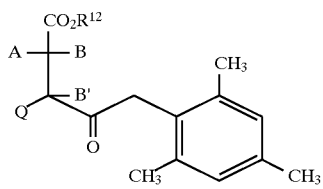
(II)

in which

A, B, B' and Q have the abovementioned meaning and $R^{12}$ represents alkyl (preferably $C_1$–$C_6$-alkyl) are subjected to an intramolecular condensation reaction in the presence of a diluent and in the presence of a base; and (B) compounds of the formula (Ib)

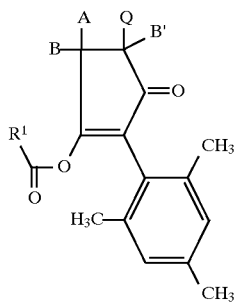
(Ib)

in which

A, B, B', Q and $R^1$ have the abovementioned meaning, are obtained when compounds of the formula (Ia),

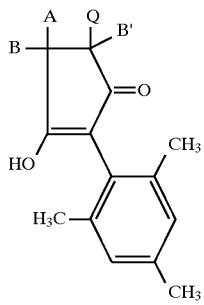
(Ia)

in which

A, B, B' and Q have the abovementioned meaning,

α) are reacted with acid halides of the formula (III)

(III)

in which

R' has the abovementioned meaning and Hal represents halogen (in particular chlorine and bromine), if appropriate in the presence of a diluent and if appropriate in the present of an acid-binding agent, or β) are reacted with carboxylic acid anhydrides of the formula (IV)

$R^1$—CO—O—CO—$R^1$ (IV)

in which $R^1$ has the abovementioned meaning, if appropriate in the presence of a diluent and if appropriate in the presence of an acid-binding agent; and (C) compounds of the formula (Ic-1)

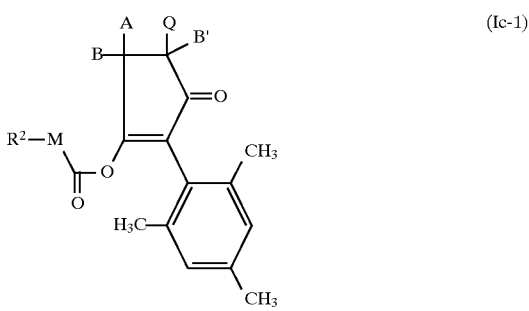
(Ic-1)

in which

A, B, B', Q and $R^2$ have the abovementioned meaning, and

M represents oxygen or sulphur, are obtained when compounds of the formula (Ia)

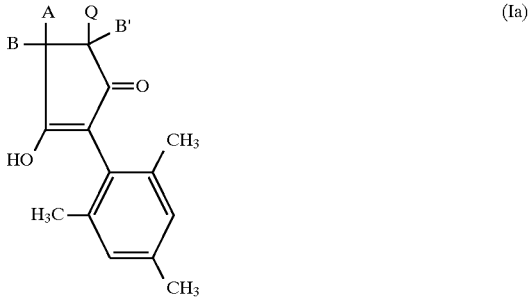
(Ia)

in which

A, B, B' and Q have the abovementioned meaning, are reacted with a chloroformic acid ester or chloroformic acid thiolester of formula (V)

$R^2$—M—CO—Cl (V)

in which $R^2$ and M have the abovementioned meaning, if appropriate in the presence of a diluent and if appropriate in the presence of an acid-binding agent; and (D) the compounds of the formula (Ic-2)

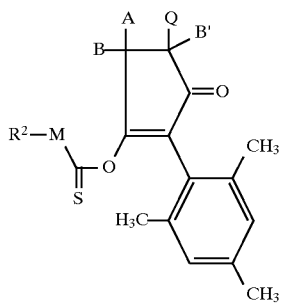

(Ic-2)

in which

A, B, B', Q and $R^2$ have the abovementioned meaning and M represents oxygen or sulphur, are obtained when compounds of the formula (Ia)

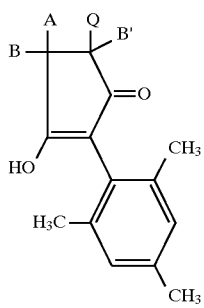

(Ia)

in which

A, B, B' and Q have the abovementioned meaning,

α) are reacted with a chloromonothioformic acid ester or chlorodithioformic acid ester of the formula (VI)

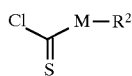

(VI)

in which

M and $R^2$ have the abovementioned meaning, if appropriate in the presence of a diluent and if appropriate in the presence of an acid-binding agent, β) are reacted with carbon disulphide and then with alkylhalides of the general formula (VII)

$R^2$-Hal    (VII)

in which $R^2$ has the abovementioned meaning and Hal represents chlorine, bromine or iodine, if appropriate in the presence of a diluent and if appropriate in the presence of a base; and (E) the compounds of the formula (Id)

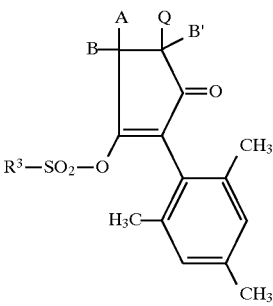

(Id)

in which

A, B, B', Q and $R^3$ have the abovementioned meaning, are obtained when compounds of the formula (Ia)

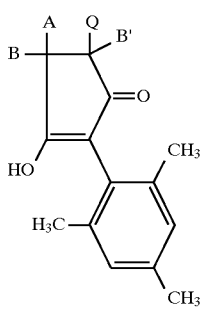

(Ia)

in which

A, B, B' and Q have the abovementioned meaning, are reacted with sulphonic acid chlorides of the formula (VIII)

$R^3$—$SO_2$—Cl    (VIII)

in which $R^3$ has the abovementioned meaning, if appropriate in the presence of a diluent and if appropriate in the presence of an acid-binding agent; and (F) compounds of the formula (Ie)

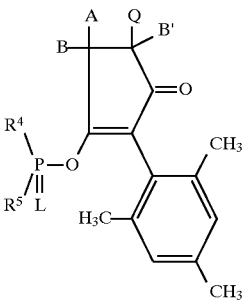

(Ie)

in which

A, B, L, B', Q, $R^4$ and $R^5$ have the abovementioned meaning, are obtained when compounds of the formula (Ia) or enols thereof

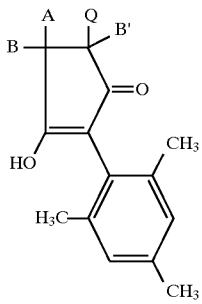
(Ia)

in which

A, B, B' and Q have the abovementioned meaning, are reacted with phosphorus compounds of the formula (IX)

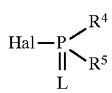
(IX)

in which

L, $R^4$ and $R^5$ have the abovementioned meaning and

Hal represents halogen (in particular chlorine and bromine), if appropriate in the presence of a diluent and if appropriate in the presence of an acid-binding agent; and (G) compounds of the formula (If)

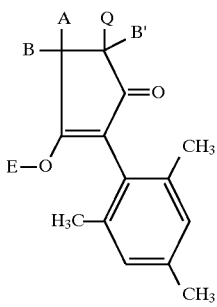
(If)

in which

A, B, B' and Q have the abovementioned meaning and

E represents a metal ion equivalent, or represents an ammonium ion, are obtained when compounds of the formula (Ia)

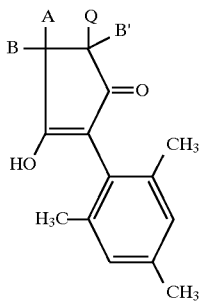
(Ia)

in which

A, B, B' and Q have the abovementioned meaning, are reacted with metal compounds or amines of the formulae (X) and (XI)

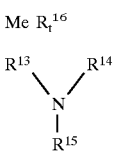
(X)

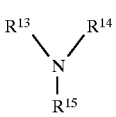
(XI)

in which

Me represents mono- or divalent metal ions (in particular alkali metal or alkaline earth metal ions, for example of lithium, sodium, potassium, magnesium or calcium), t represents a number 1 or 2, $R^{13}$, $R^{14}$ and $R^{15}$, independently of one another represent hydrogen or alkyl (in particular $C_1$–$C_8$-alkyl) and $R^{16}$ represents hydrogen, hydroxyl or $C_1$–$C_4$-alkoxy, if appropriate in the presence of a diluent.

(H) It has furthermore been found that compounds of the formula (Ig)

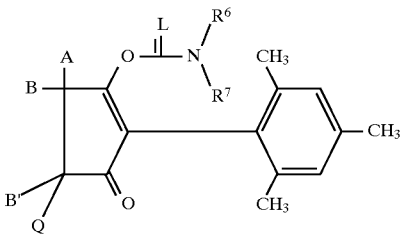
(Ig)

in which

A, B, L, B', Q, $R^6$ and $R^7$ have the abovementioned meaning, are obtained when compounds of the formula (Ia)

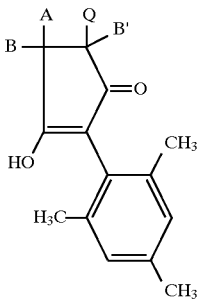
(Ia)

in which

A, B, B' and Q have the abovementioned meaning, are reacted

α) with compounds of the formula (XII)

(XII)

in which

L and $R^6$ have the abovementioned meaning, if appropriate in the presence of a diluent and if appropriate in the presence of a catalyst, or β) with carbamic acid chlorides or thiocarbamic acid chlorides of the formula (XIII)

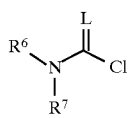 (XIII)

in which

L, $R^6$ and $R^7$ have the abovementioned meaning, if appropriate in the presence of a diluent and if appropriate in the presence of an acid-binding agent.

It has furthermore been found that the novel 2-(2,4,6-trimethylphenyl)-cyclopentane-1,3-dione derivatives of the formula (I) are distinguished by outstanding insecticidal, acaricidal and herbicidal actions.

Formula (I) provides a general definition of the compounds according to the invention.

Preferred substituents and ranges of the radicals listed in the formulae mentioned above and below are explained in the following.

A and Q together preferably represent $C_1$–$C_6$-alkane diyl or $C_2$–$C_6$-alkenediyl, which is in each case optionally substituted once to three times in an identical or different manner by halogen, hydroxyl or mercapto, or by $C_1$–$C_{10}$-alkyl, $C_1$–$C_6$-alkoxy, $C_1$–$C_6$-alkylthio or $C_3$–$C_7$-cycloalkyl, in each case optionally halogen-substituted once to nine times in an identical or different manner, or by benzyloxy or phenyl, in each case optionally substituted once to five times in an identical or different manner by halogen, $C_1$–$C_6$-alkyl or $C_1$–$C_6$-alkoxy, and which furthermore optionally contains one of the following groupings

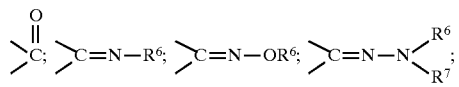

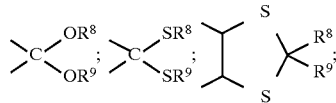

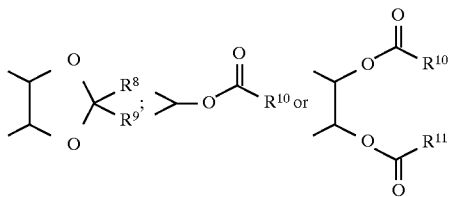

or is bridged by a $C_1$–$C_2$-alkanediyl group.

B and B' independently of one another preferably represent hydrogen, halogen or $C_1$–$C_6$-alkyl, or together represent $C_1$–$C_6$-alkanediyl or $C_4$-alkenediyl, in each case optionally substituted by $C_1$–$C_6$-alkyl.

G preferably represents hydrogen (a), or represents one of the groups

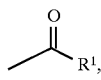 (b)

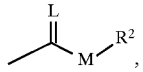 (c)

 (d)

 (e)

E (f)

or

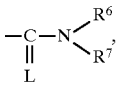 (g)

in which

E represents a metal ion equivalent or an ammonium ion,

L represents oxygen or sulphur and

M represents oxygen or sulphur.

$R^1$ preferably represents $C_1$–$C_{20}$-alkyl, $C_2$–$C_{10}$-alkenyl, $C_1$–$C_8$-alkoxy-$C_1$–$C_8$-alkyl, $C_1$–$C_8$-alkylthio-$C_1$–$C_8$-alkyl, or poly-$C_1$–$C_8$-alkoxy-$C_1$–$C_8$-alkyl, in each case optionally substituted once or several times in an identical or different manner by halogen, or represents cycloalkyl having 3 to 8 ring atoms, which is optionally substituted once or several times in an identical or different manner by halogen, $C_1$–$C_6$-alkyl or $C_1$–$C_6$-alkoxy and in which at least one methylene group can be replaced by an oxygen and/or sulphur atom, or represents phenyl which is optionally substituted once or several times in an identical or different manner by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents phenyl-$C_1$–$C_6$-alkyl which is optionally substituted once or several times in an identical or different manner by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which has 5 or 6 ring atoms and is optionally substituted once or several times in an identical or different manner by halogen or $C_1$–$C_6$-alkyl, or represents phenoxy-$C_1$–$C_6$-alkyl which is optionally substituted once or several times in an identical or different manner by halogen or $C_1$–$C_6$-alkyl, or represents hetaryloxy-$C_1$–$C_6$-alkyl which has 5 or 6 ring atoms and is optionally substituted once or several times in an identical or different manner by halogen, amino or $C_1$–$C_6$-alkyl.

$R^2$ preferably represents $C_1$–$C_{20}$-alkyl, $C_2$–$C_{10}$-alkenyl, $C_1$–$C_8$-alkoxy-$C_2$–$C_8$-alkyl, or poly-$C_1$–$C_8$-alkoxy-$C_2$–$C_8$-alkyl, in each case optionally substituted once or several times in an identical or different manner by halogen, or represents $C_3$–$C_6$-cycloalkyl which is optionally substituted once or several times in an identical or different manner by halogen, $C_1$–$C_6$-alkyl or $C_1$–$C_6$-alkoxy, or represents phenyl or benzyl, in each case optionally substituted once or several times in an identical or different manner by halogen, nitro, cyano, $C_1$–$C_6$-alkyl, $C_1$–$C_6$-alkoxy, $C_1$–$C_3$-halogenoalkoxy or $C_1$–$C_3$-halogenoalkyl.

$R^3$ preferably represents $C_1$–$C_{12}$-alkyl which is optionally substituted once or several times in an identical or different manner by halogen, or represents phenyl or phenyl-$C_1$–$C_4$-alkyl, in each case optionally substituted once or several times in an identical or different manner by halogen, $C_1$–$C_6$-alkyl, $C_1$–$C_6$-alkoxy, $C_1$–$C_3$-halogenoalkyl, $C_1$–$C_3$-halogenoalkoxy, cyano or nitro.

$R^4$ and $R^5$ independently of one another represent $C_1$–$C_8$-alkyl, $C_1$–$C_8$-alkoxy, $C_1$–$C_8$-alkylamino, di-($C_1$–$C_8$-alkyl)-amino, $C_1$–$C_8$-alkylthio, $C_3$–$C_5$-alkenylthio, or $C_3$–$C_7$-cycloalkylthio, in each case optionally substituted once or several times in an identical or different manner by halogen, or represent phenyl, phenoxy or phenylthio, in each case optionally substituted once or several times in an identical or different manner by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ preferably represents hydrogen or $C_1$–$C_{10}$-alkyl, $C_3$–$C_8$-alkenyl or $C_1$–$C_8$-alkoxy-$C_2$–$C_8$-alkyl, in each case optionally substituted once or several times in an identical or different manner by halogen, or represents $C_3$–$C_{10}$-cycloalkyl which is optionally substituted once or several times in an identical or different manner by halogen, $C_1$–$C_6$-alkyl, $C_1$–$C_6$-alkoxy, $C_1$–$C_3$-halogenoalkyl or $C_1$–$C_3$-halogenoalkoxy, or represents phenyl which is optionally substituted once or several times in an identical or different manner by halogen, $C_1$–$C_3$-halogenoalkyl, $C_1$–$C_8$-alkyl, $C_1$–$C_3$-halogenoalkoxy or $C_1$–$C_8$-alkoxy, or represents benzyl which is optionally substituted once or several times in an identical or different manner by halogen, $C_1$–$C_8$-alkyl, $C_1$–$C_3$-halogenoalkyl, $C_1$–$C_3$-halogenoalkoxy or $C_1$–$C_8$-alkoxy.

$R^7$ preferably represents hydrogen or $C_1$–$C_{10}$-alkyl or $C_3$–$C_{10}$-alkenyl, in each case optionally substituted once or several times in an identical or different manner by halogen, or $R^6$ and $R^7$, together with the N atom to which they are bonded, preferably represent a 3- to 7-membered ring which optionally contains oxygen or sulphur.

$R^8$ and $R^9$ independently of one another preferably represent hydrogen or $C_1$–$C_6$-alkyl or different manner by halogen, or represent phenyl or phenyl-$C_1$–$C_4$-alkyl, in each case optionally substituted once or several times in an identical or different manner by halogen, $C_1$–$C_6$-alkyl, $C_1$–$C_6$-alkoxy, $C_1$–$C_6$-halogenoalkyl, $C_1$–$C_6$-halogenoalkoxy, nitro or cyano, or together represent $C_2$–$C_6$-alkanediyl which is optionally substituted once or several times in an identical or different manner by halogen, $C_1$–$C_6$-alkyl, $C_1$–$C_6$-alkoxy or $C_1$–$C_3$-halogenoalkyl.

$R^{10}$ and $R^{11}$ independently of one another preferably represent $C_1$–$C_{10}$-alkyl, $C_2$–$C_{10}$-alkenyl, $C_1$–$C_{10}$-alkoxy, $C_1$–$C_{10}$-alkylamino or di-($C_1$–$C_{10}$-alkyl)-amino, $C_3$–$C_{10}$-alkenylamino or di-($C_3$–$C_{10}$-alkenyl)-amino, in each case substituted once or several times in an identical or different manner by halogen, or phenyl or benzyl, in each case optionally substituted once or several times in an identical or different manner by halogen, $C_1$–$C_4$-alkyl, $C_1$–$C_4$-alkoxy, $C_1$–$C_4$-halogenoalkyl, nitro or cyano.

A and Q together particularly preferably represent $C_1$–$C_5$-alkanediyl or $C_2$–$C_5$-alkenediyl, which is in each case optionally substituted once to three times in an identical or different manner by fluorine, chlorine, bromine, hydroxyl or mercapto, or by $C_1$–$C_8$-alkyl, $C_1$–$C_4$-alkoxy, $C_1$–$C_4$-alkylthio, $C_5$–$C_7$-cycloalkyl or phenyl, in each case optionally substituted once to five times in an identical or different manner by fluorine or chlorine, and which furthermore optionally contains one of the following groupings:

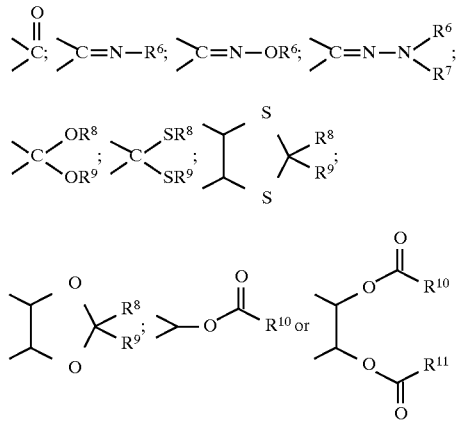

or is bridged by a $C_1$–$C_2$-alkanediyl group.

B and B' independently of one another particularly preferably represent hydrogen, fluorine, chlorine or $C_1$–$C_4$-alkyl, or together represent $C_1$–$C_5$-alkanediyl or $C_4$-alkenediyl, in each case optionally substituted by $C_1$–$C_4$-alkyl.

G particularly preferably represents hydrogen (a) or represents one of the groups

 (b)

 (c)

 (d)

 (e)

E (f)

or

 (g)

in which

E represents a metal ion equivalent or an ammonium ion,

L represents oxygen or sulphur and

M represents oxygen or sulphur.

$R^1$ particularly preferably represents $C_1$–$C_{16}$-alkyl, $C_2$–$C_8$-alkenyl, $C_1$–$C_6$-alkoxy-$C_1$–$C_6$-alkyl, $C_1$–$C_6$-alkylthio-$C_1$–$C_6$-alkyl, or poly-$C_1$–$C_6$-alkoxy-$C_1$–$C_6$-alkyl, in each case optionally substituted once to nine times in an identical or different manner by fluorine or chlorine, or represents cycloalkyl which has 3 to 7 ring atoms, and is optionally substituted once to three times in an identical or different manner by fluorine, chlorine, $C_1$–$C_4$-alkyl or $C_1$–$C_4$-alkoxy, and in which one or two methylene groups can be replaced by oxygen and/or sulphur atoms, or represents phenyl which is optionally substituted once to three times in an identical or different manner by fluorine, chlorine, bromine, cyano, nitro, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted once to three times in an identical or different manner by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents furanyl, thienyl, pyridyl, pyrimidyl, thiazolyl or pyrazolyl, in each case optionally substituted once or twice in an identical or different manner by fluorine, chlorine, bromine or $C_1$–$C_4$-alkyl, or represents phenoxy-$C_1$–$C_5$-alkyl which is optionally substituted once to three times in an identical or different manner by fluorine, chlorine or $C_1$–$C_4$-alkyl, or represents pyridyloxy-$C_1$–$C_6$-alkyl, pyrimidinyloxy-$C_1$–$C_6$-alkyl or thiazolyloxy-$C_1$–$C_6$-alkyl, in each case optionally substituted once or twice in an identical or different manner by fluorine, chlorine, amino or $C_1$–$C_4$-alkyl.

$R^2$ particularly preferably represents $C_1$–$C_{16}$-alkyl, $C_2$–$C_8$-alkenyl, $C_1$–$C_6$-alkoxy-$C_2$–$C_6$-alkyl, or poly-$C_1$–$C_6$-alkoxy-$C_2$–$C_6$-alkyl, in each case optionally substituted once to nine times in an identical or different manner by fluorine or chlorine, or represents $C_3$–$C_6$-cycloalkyl which is optionally substituted once to five times in an identical or different manner by fluorine, chlorine, $C_1$–$C_4$-alkyl or $C_1$–$C_4$-alkoxy, or represents phenyl or benzyl, in each case optionally substituted once to three times in an identical or different manner by fluorine, chlorine, bromine, nitro, cyano, $C_1$–$C_4$-alkyl, $C_1$–$C_4$-alkoxy, $C_1$–$C_2$-halogenoalkoxy or $C_1$–$C_2$-halogenoalkyl.

$R^3$ particularly preferably represents $C_1$–$C_9$-alkyl which is optionally substituted once to five times in an identical or different manner by fluorine or chlorine, or represents phenyl or phenyl-$C_1$–$C_2$-alkyl, in each case optionally substituted once to three times in an identical or different manner by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

$R^4$ and $R^5$ independently of one another particularly preferably represent $C_1$–$C_6$-alkyl, $C_1$–$C_6$-alkoxy, $C_1$–$C_6$-alkylamino, di-($C_1$–$C_6$-alkyl)-amino, $C_1$–$C_6$-alkylthio, $C_3$–$C_4$-alkenylthio, or $C_3$–$C_6$-cycloalkylthio, optionally substituted once to five times in an identical or different manner by fluorine, or chlorine, or represent phenyl, phenoxy or phenylthio, in each case optionally substituted once to three times in an identical or different manner by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ particularly preferably represents hydrogen or $C_1$–$C_8$-alkyl, $C_3$–$C_6$-alkenyl or $C_1$–$C_6$-alkoxy-$C_2$–$C_6$-alkyl, in each case optionally substituted once to five times in an identical or different manner by fluorine or chlorine, or represents $C_3$–$C_8$-cycloalkyl which is optionally substituted once to three times in an identical or different manner by fluorine, chlorine, $C_1$–$C_4$-alkyl, $C_1$–$C_4$-alkoxy, $C_1$–$C_2$-halogenoalkyl or $C_1$–$C_2$-halogenoalkoxy, or represents phenyl which is optionally substituted once to three times in an identical or different manner by fluorine, chlorine, bromine, $C_1$–$C_2$-halogenoalkyl, $C_1$–$C_5$-alkyl, $C_1$–$C_2$-halogenoalkoxy or $C_1$–$C_5$-alkoxy, or represents benzyl which is optionally substituted once to three times in an identical or different manner by fluorine, chlorine, bromine, $C_1$–$C_5$alkyl, $C_1$–$C_2$-halogenoalkyl, $C_1$–$C_2$-halogenoalkoxy or $C_1$–$C_5$-alkoxy.

$R^7$ particularly preferably represents hydrogen or $C_1$–$C_8$-alkyl or $C_3$–$C_8$-alkenyl, in each case optionally substituted once to five times in an identical or different manner by fluorine or chlorine, or $R^6$ and $R^7$, together with the N atom to which they are bonded, particularly preferably represent a 4- to 7-membered ring which optionally contains oxygen or sulphur.

$R^8$ and $R^9$ independently of one another particularly preferably represent hydrogen or $C_1$–$C_4$-alkyl which is optionally substituted once to five times in an identical or different manner by fluorine or chlorine, or represent phenyl which is optionally substituted once to three times in an identical or different manner by fluorine, chlorine, $C_1$–$C_4$-alkyl, $C_1$–$C_4$-alkoxy, $C_1$–$C_2$-halogenoalkyl, $C_1$–$C_2$-halogenoalkoxy, nitro or cyano, or together represent $C_2$–$C_5$-alkanediyl which is optionally substituted once to three times in an identical or different manner by fluorine, chlorine, $C_1$–$C_4$-alkyl, $C_1$–$C_4$-alkoxy or $C_1$–$C_2$-halogenoalkyl.

$R^{10}$ and $R^{11}$ independently of one another particularly preferably represent $C_1$–$C_8$-alkyl, $C_2C_8$-alkenyl, $C_1$–$C_8$-alkoxy, $C_1$–$C_8$-alkylamino, $C_3$–$C_8$-alkenylamino, di-($C_1$–$C_8$-alkyl)-amino or di-($C_3$–$C_8$-alkenyl)-amino, in each case optionally substituted once to five times in an identical or different manner by fluorine or chlorine.

A and Q together especially preferably represent $C_1$–$C_4$-alkanediyl or $C_2$–$C_4$-alkenediyl, which is in each case optionally substituted once or twice in an identical or different manner by fluorine, chlorine, hydroxyl or mercapto, or by $C_1$–$C_6$-alkyl, $C_1$–$C_2$-alkoxy, $C_1$–$C_2$-alkylthio, $C_5$–$C_6$-cycloalkyl or phenyl, in each case optionally substituted once to three times in an identical or different manner by fluorine or chlorine, and which furthermore optionally contains one of the following groups:

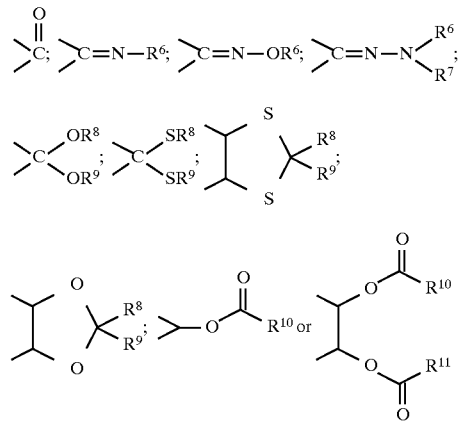

or is bridged by a $C_1$–$C_2$-alkanediyl group.

B and B' independently of one another especially preferably represent hydrogen, fluorine, chlorine, methyl or ethyl, or together represent $C_1$–$C_4$-alkanediyl or $C_4$-alkenediyl, in each case optionally substituted by methyl or ethyl.

G especially preferably represents hydrogen (a) or represents one of the groups

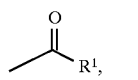 (b)

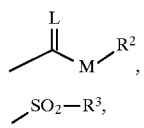 (c)

 (d)

 (e)

E (f)

or

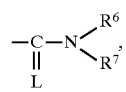 (g)

in which
E represents a metal ion equivalent or an ammonium ion,
L represents oxygen or sulphur and
M represents oxygen or sulphur.

$R^1$ especially preferably represents $C_1-C_{14}$-alkyl, $C_2-C_6$-alkenyl, $C_1-C_4$-alkoxy-$C_1-C_6$-alkyl, $C_1-C_4$-alkylthio-$C_1-C_6$-alkyl, or poly-$C_1-C_4$-alkoxy-$C_1-C_4$-alkyl, in each case optionally substituted once to five times in an identical or different manner by fluorine or chlorine, or represents cycloalkyl which has 3 to 6 ring atoms and is optionally substituted once or twice in an identical or different manner by fluorine, chlorine, methyl, ethyl, methoxy or ethoxy, and in which one or two methylene groups can be replaced by oxygen and/or sulphur atoms, or represents phenyl which is optionally substituted once or twice in an identical or different manner by fluorine, chlorine, bromine, methyl, ethyl, propyl, i-propyl, methoxy, ethoxy, trifluoromethyl, trifluoromethoxy, cyano or nitro, or represents benzyl which is optionally substituted once or twice in an identical or different manner by fluorine, chlorine, bromine, methyl, ethyl, propyl, i-propyl, methoxy, ethoxy, trifluoromethyl or trifluoromethoxy, or represents thienyl, furanyl or pyridyl, in each case optionally substituted once or twice in an identical or different manner by fluorine, chlorine, bromine, methyl or ethyl, or represents phenoxy-$C_1-C_4$-alkyl which is optionally substituted once or twice in an identical or different manner by fluorine, chlorine, methyl or ethyl, or represents pyridyloxy-$C_1-C_4$-alkyl, pyrimidyloxy-$C_1-C_4$-alkyl or thiazolyloxy-$C_1-C_4$-alkyl, in each case optionally substituted once or twice in an identical or different manner by fluorine, chlorine, amino, methyl or ethyl.

$R^2$ especially preferably represents $C_1-C_{14}$-alkyl, $C_2-C_6$-alkenyl, $C_1-C_4$-alkoxy-$C_2-C_6$-alkyl, or poly-$C_1-C_4$-alkoxy-$C_2-C_6$-alkyl, in each case optionally substituted once to five times in an identical or different manner by fluorine or chlorine, or represents $C_3-C_6$-cycloalkyl which is optionally substituted once to three times in an identical or different manner by fluorine, chlorine, methyl, ethyl, methoxy or ethoxy, or represents phenyl or benzyl, in each case optionally substituted once or twice in an identical or different manner by fluorine, chlorine, nitro, cyano, methyl, ethyl, propyl, i-propyl, methoxy, ethoxy, trifluoromethoxy or trifluoromethyl.

$R^3$ especially preferably represents $C_1-C_6$-alkyl which is optionally substituted once to three times in an identical or different manner by fluorine or chlorine, or represents phenyl or benzyl, in each case optionally substituted once or twice by fluorine, chlorine, bromine, methyl, ethyl, methoxy, ethoxy, trifluoromethyl, trifluoromethoxy, cyano or nitro.

$R^4$ and $R^5$ independently of one another especially preferably represent $C_1-C_4$-alkyl, $C_1-C_4$-alkoxy, $C_1-C_4$-alkylamino, di-($C_1-C_4$-alkyl)-amino, $C_1-C_4$-alkylthio, in each case optionally substituted once to three times in an identical or different manner by fluorine or chlorine, or represent phenyl, phenoxy or phenylthio, in each case optionally substituted once or twice in an identical or different manner by fluorine, chlorine, bromine, nitro, cyano, $C_1-C_2$-alkoxy, trifluoromethoxy, $C_1-C_2$-alkylthio, trifluoromethyl or $C_1-C_3$-alkyl.

$R^6$ especially preferably represents hydrogen or $C_1-C_6$-alkyl or $C_1-C_6$-alkoxy-$C_2-C_4$-alkyl, in each case optionally substituted once to three times in an identical or different manner by fluorine or chlorine, or represents $C_3-C_6$-cycloalkyl which is optionally substituted once or twice in an identical or different manner by fluorine, chlorine, methyl, methoxy, trifluoromethyl or trifluoromethoxy, or represents phenyl which is optionally substituted once or twice in an identical or different manner by fluorine, chlorine, trifluoromethyl, $C_1-C_4$-alkyl, trifluoromethoxy or $C_1-C_4$-alkoxy, or represents benzyl which is optionally substituted once or twice in an identical or different manner by fluorine, chlorine, $C_1-C_4$-alkyl, trifluoromethyl, trifluoromethoxy or $C_1-C_4$-alkoxy.

$R^7$ especially preferably represents hydrogen or $C_1-C_6$-alkyl or $C_3-C_6$-alkenyl, in each case optionally substituted once to three times in an identical or different manner by fluorine or chlorine, or $R^6$ and $R^7$, together with the N atom to which they are bonded, especially preferably represent a 5- to 7-membered ring which optionally contains oxygen or sulphur.

$R^8$ and $R^9$ independently of one another especially preferably represent hydrogen or $C_1-C_4$-alkyl which is optionally substituted once to three times in an identical or different manner by fluorine or chlorine, or represent phenyl which is optionally substituted once or twice in an identical or different manner by fluorine, chlorine, methyl, ethyl, methoxy, ethoxy, trifluoromethyl, trifluoromethoxy, nitro or cyano, or together represent $C_2-C_5$-alkanediyl which is optionally substituted once or twice in an identical or different manner by fluorine, chlorine, methyl, ethyl, methoxy, ethoxy or trifluoromethyl.

$R^{10}$ and $R^{11}$ independently of one another especially preferably represent $C_1-C_6$-alkyl or $C_2-C_6$-alkenyl.

The abovementioned definitions of radicals and explanations given generally or in preferred ranges can be combined as desired with one another, that is to say also between the particular ranges and preferred ranges. They apply accordingly to the end products and to the precursors and intermediate products.

In the abovementioned definitions, saturated or unsaturated hydrocarbon radicals, including in combination with heteroatoms (for example alkoxy or alkenylthio), can in each case, where possible, be straight-chain or branched.

Compounds of the formula (I) which are preferred according to the invention are those in which a combination of the meanings given above as preferred (preferably) is present.

Compounds of the formula (I) which are particularly preferred according to the invention are those in which a combination of the meanings given above as particularly preferred is present.

Compounds of the formula (I) which are especially preferred according to the invention are those in which a combination of the meanings given above as especially preferred is present.

In addition to the compounds mentioned in the preparation examples, the following 2-mesityl-3-hydroxy-$\Delta^2$-cyclopentenone derivatives of the formulae (Ia) to (Ig) (Tables 1 to 6) may be mentioned specifically.

TABLE 1

(Ia)

| A | Q | B | B' |
|---|---|---|---|
| —CH$_2$— | | H | H |
| —(CH$_2$—)$_2$— | | H | H |
| —CH═CH— | | H | H |
| —CH——CH— <br>     \|       \| <br>   CH$_3$   CH$_3$ | | H | H |
| —(CH$_2$)$_2$— | | CH$_3$ | CH$_3$ |
| —(CH$_2$)$_3$— | | H | H |
| —(CH$_2$)$_2$—CHCH$_3$— | | H | H |
| —(CH$_2$)$_2$—CHOCH$_3$— | | H | H |
| —CH$_2$—CHCH$_3$—CH$_2$— | | H | H |
| —CH$_2$—CHOCH$_3$—CH$_2$— | | H | H |
| —CH$_2$—CHCH$_3$—CHCH$_3$— | | H | H |
| —CH$_2$——CHOCH$_3$—CHOCH$_3$ | | H | H |
| —(CH$_2$)$_4$— | | H | H |
| —(CH$_2$)$_3$—CHCH$_3$— | | H | H |
| —(CH$_2$)$_3$—CHOCH$_3$— | | H | H |
| —(CH$_2$)$_2$—CHCH$_3$—CH$_2$— | | H | H |
| —(CH$_2$)$_2$—CHOCH$_3$—CH$_2$— | | H | H |
| —(CH$_2$)$_3$—CHCH$_3$— | | H | H |
| —(CH$_2$)$_3$—CHOCH$_3$— | | H | H |
| —(CH$_2$)$_4$— | | CH$_3$ | H |
| —CH$_2$—CHCH$_3$—CHCH$_3$—CH$_2$— | | H | H |
| —(CH$_2$)$_2$—CHCH$_3$—CHCH$_3$— | | H | H |
| —(CH$_2$)$_2$—CHOH—CH$_2$— | | H | H |
| —CH$_2$—CHOH—CHOH—CH$_2$— | | H | H |
| —CH$_2$—CH————CH—CH$_2$— <br>         \|           \| <br>         O—CH$_2$—O | | H | H |
| —CH$_2$—CH————CH—CH$_2$— <br>         \|           \| <br>      O—C(CH$_3$)$_2$—O | | H | H |
| —(CH$_2$)$_4$— | | —CH$_2$— | |
| —(CH$_2$)$_4$— | | —(CH$_2$)$_2$— | |
| —(CH$_2$)$_2$—C—CH$_2$— <br>          \|\| <br>          O | | H | H |

TABLE 1-continued (Ia)

| A | Q | B | B' |
|---|---|---|---|
| —(CH$_2$)$_2$—C—CH$_2$— <br>          \|\| <br>         N—OCH$_3$ | | H | H |

TABLE 2

(Ib)

| A | Q | B | B' | R$^1$ |
|---|---|---|---|---|
| —CH$_2$— | | H | H | CH$_3$ |
| —(CH$_2$)$_2$— | | H | H | CH$_3$ |
| —CH——CH— <br>    \|      \| <br>   CH$_3$  CH$_3$ | | H | H | CH$_3$ |
| —(CH$_2$)$_2$— | | CH$_3$ | CH$_3$ | CH$_3$ |
| —(CH$_2$)$_3$— | | H | H | CH$_3$ |
| —(CH$_2$)$_2$—CHCH$_3$— | | H | H | CH$_3$ |
| —(CH$_2$)$_2$—CHOCH$_3$— | | H | H | CH$_3$ |
| —CH$_2$—CHCH$_3$—CH$_2$— | | H | H | CH$_3$ |
| —CH$_2$—CHOCH$_3$—CH$_2$— | | H | H | CH$_3$ |
| —CH$_2$—CHCH$_3$—CHCH$_3$— | | H | H | CH$_3$ |
| —CH$_2$—CHOCH$_3$—CHOCH$_3$ | | H | H | CH$_3$ |
| —(CH$_2$)$_4$— | | H | H | CH$_3$ |
| —(CH$_2$)$_3$—CHCH$_3$— | | H | H | CH$_3$ |
| —(CH$_2$)3—CHOCH$_3$— | | H | H | CH$_3$ |
| —(CH$_2$)$_2$—CHCH$_3$—CH$_2$— | | H | H | CH$_3$ |
| —(CH$_2$)$_2$—CHOCH$_3$—CH$_2$— | | H | H | CH$_3$ |
| —(CH$_2$)$_3$—CHCH$_3$— | | H | H | CH$_3$ |
| —(CH$_2$)$_3$—CHOCH$_3$ | | H | H | CH$_3$ |
| —(CH$_2$)$_4$— | | CH$_3$ | H | CH$_3$ |
| —CH$_2$—CHCH$_3$—CHCH$_3$—CH$_2$— | | H | H | CH$_3$ |
| —(CH$_2$)$_2$—CHCH$_3$—CHCH$_3$ | | H | H | CH$_3$ |
| —(CH$_2$)$_2$—CHOH—CH$_2$— | | H | H | CH$_3$ |
| —CH$_2$—CHOH—CHOH—CH$_2$— | | H | H | CH$_3$ |
| —CH$_2$—CH————CH—CH$_2$— <br>         \|           \| <br>         O—CH$_2$—O | | H | H | CH$_3$ |
| —CH$_2$—CH————CH—CH$_2$— <br>         \|           \| <br>      O—C(CH$_3$)$_2$—O | | H | H | CH$_3$ |
| —(CH$_2$)$_4$— | | —CH$_2$— | | CH$_3$ |
| —(CH$_2$)$_4$— | | —(CH$_2$)$_2$— | | CH$_3$ |

TABLE 2-continued $$\text{(Ib)}$$

Structure (Ib): cyclopentanone-type ring with substituents A, Q, B, B' on ring carbons, R¹−C(=O)−O− attached to the enol carbon, and a 2,4,6-trimethylphenyl group attached to the adjacent ring carbon.

| A Q | B | B' | R¹ |
|---|---|---|---|
| −(CH₂)₂−C(=O)−CH₂− | H | H | CH₃ |
| −(CH₂)₂−C(=N−OCH₃)−CH₂− | H | H | CH₃ |
| −CH₂− | H | H | i-C₃H₇ |
| −(CH₂)₂− | H | H | i-C₃H₇ |
| −CH(CH₃)−CH(CH₃)− | H | H | i-C₃H₇ |
| −(CH₂)₂− | CH₃ | CH₃ | i-C₃H₇ |
| −(CH₂)₃− | H | H | i-C₃H₇ |
| −(CH₂)₂−CHCH₃− | H | H | i-C₃H₇ |
| −(CH₂)₂−CHOCH₃− | H | H | i-C₃H₇ |
| −CH₂−CHCH₃−CH₂− | H | H | i-C₃H₇ |
| −CH₂−CHOCH₃−CH₂− | H | H | i-C₃H₇ |
| −CH₂−CHCH₃−CHCH₃− | H | H | i-C₃H₇ |
| −CH₂−CHOCH₃−CHOCH₃− | H | H | i-C₃H₇ |
| −(CH₂)₄− | H | H | i-C₃H₇ |
| −(CH₂)₃−CHCH₃− | H | H | i-C₃H₇ |
| −(CH₂)₃−CHOCH₃− | H | H | i-C₃H₇ |
| −(CH₂)₂−CHCH₃−CH₂− | H | H | i-C₃H₇ |
| −(CH₂)₂−CHOCH₃−CH₂− | H | H | i-C₃H₇ |
| −(CH₂)₃−CHCH₃− | H | H | i-C₃H₇ |
| −(CH₂)₃−CHOCH₃− | H | H | i-C₃H₇ |
| −(CH₂)₄− | CH₃ | H | i-C₃H₇ |
| −CH₂−CHCH₃−CHCH₃−CH₂− | H | H | i-C₃H₇ |
| −(CH₂)₂−CHCH₃−CHCH₃− | H | H | i-C₃H₇ |
| −(CH₂)₂−CHOH−CH₂− | H | H | i-C₃H₇ |
| −CH₂−CHOH−CHOH₂−CH₂− | H | H | i-C₃H₇ |
| −CH₂−CH(−O−CH₂−O−)CH−CH₂− | H | H | i-C₃H₇ |
| −CH₂−CH(−O−C(CH₃)₂−O−)CH−CH₂− | H | H | i-C₃H₇ |
| −(CH₂)₄− | −CH₂− | | i-C₃H₇ |
| −(CH₂)₄− | −(CH₂)₂− | | i-C₃H₇ |
| −(CH₂)₂−C(=O)−CH₂− | H | H | i-C₃H₇ |
| −(CH₂)₂−C(=N−OCH₃)−CH₂− | H | H | i-C₃H₇ |
| −CH₂− | H | H | t-C₄H₉ |
| −(CH₂)₂− | H | H | t-C₄H₉ |
| −CH(CH₃)−CH(CH₃)− | H | H | t-C₄H₉ |
| −(CH₂)₂− | CH₃ | CH₃ | t-C₄H₉ |
| −(CH₂)₃− | H | H | t-C₄H₉ |
| −(CH₂)₂−CHCH₃− | H | H | t-C₄H₉ |
| −(CH₂)₂−CHOCH₃− | H | H | t-C₄H₉ |
| −CH₂−CHCH₃−CH₂− | H | H | t-C₄H₉ |
| −CH₂−CHOCH₃−CH₂− | H | H | t-C₄H₉ |
| −CH₂−CHCH₃−CHCH₃− | H | H | t-C₄H₉ |
| −CH₂−CHOCH₃−CHOCH₃− | H | H | t-C₄H₉ |
| −(CH₂)₄− | H | H | t-C₄H₉ |
| −(CH₂)₃−CHCH₃− | H | H | t-C₄H₉ |
| −(CH₂)₃−CHOCH₃− | H | H | t-C₄H₉ |
| −(CH₂)₂−CHCH₃−CH₂− | H | H | t-C₄H₉ |
| −(CH₂)₂−CHOCH₃−CH₂− | H | H | t-C₄H₉ |
| −(CH₂)₃−CHCH₃− | H | H | t-C₄H₉ |
| −(CH₂)₃−CHOCH₃− | H | H | t-C₄H₉ |
| −(CH₂)₄− | CH₃ | H | t-C₄H₉ |
| −CH₂−CHCH₃−CHCH₃−CH₂− | H | H | t-C₄H₉ |
| −(CH₂)₂−CHCH₃−CHCH₃− | H | H | t-C₄H₉ |
| −(CH₂)₂−CHOH−CH₂− | H | H | t-C₄H₉ |
| −CH₂−CHOH−CHOH−CH₂− | H | H | t-C₄H₉ |
| −CH₂−CH(−O−CH₂−O−)CH−CH₂− | H | H | t-C₄H₉ |
| −CH₂−CH(−O−C(CH₃)₂−O−)CH−CH₂− | H | H | t-C₄H₉ |
| −(CH₂)₄− | −CH₂− | | t-C₄H₉ |
| −(CH₂)₄− | −(CH₂)₂− | | t-C₄H₉ |
| −(CH₂)₂−C(=O)−CH₂− | H | H | t-C₄H₉ |
| −(CH₂)₂−C(=N−OCH₃)−CH₂− | H | H | t-C₄H₉ |
| −CH₂− | H | H | Ph (= Phenyl) |
| −(CH₂)₂− | H | H | Ph |
| −CH(CH₃)−CH(CH₃)− | H | H | Ph |
| −(CH₂)₂− | CH₃ | CH₃ | Ph |
| −(CH₂)₃− | H | H | Ph |
| −(CH₂)₂−CHCH₃− | H | H | Ph |
| −(CH₂)₂−CHOCH₃− | H | H | Ph |
| −CH₂−CHCH₃−CH₂− | H | H | Ph |
| −CH₂−CHOCH₃−CH₂− | H | H | Ph |
| −CH₂−CHCH₃−CHCH₃− | H | H | Ph |
| −CH₂−CHOCH₃−CHOCH₃− | H | H | Ph |
| −(CH₂)₄− | H | H | Ph |
| −(CH₂)₃−CHCH₃− | H | H | Ph |
| −(CH₂)₃−CHOCH₃− | H | H | Ph |
| −(CH₂)₂−CHCH₃−CH₂− | H | H | Ph |
| −(CH₂)₂−CHOCH₃−CH₂− | H | H | Ph |
| −(CH₂)₃−CHCH₃− | H | H | Ph |
| −(CH₂)₃−CHOCH₃− | H | H | Ph |
| −(CH₂)₄− | CH₃ | H | Ph |
| −CH₂−CHCH₃−CHCH₃−CH₂− | H | H | Ph |
| −(CH₂)₂−CHCH₃−CHCH₃− | H | H | Ph |
| −(CH₂)₂−CHOH−CH₂− | H | H | Ph |
| −CH₂−CHOH−CHOH−CH₂− | H | H | Ph |

TABLE 2-continued (Ib) structure: cyclopentanone with A, B, Q, B' substituents, R¹C(O)O- group, and 2,4,6-trimethylphenyl group

| A | Q | B | B' | R¹ |
|---|---|---|---|---|
| —CH₂—CH(O—CH₂—O)CH—CH₂— | | H | H | Ph |
| —CH₂—CH(O—C(CH₃)₂—O)CH—CH₂— | | H | H | Ph |
| —(CH₂)₄— | | —CH₂— | | Ph |
| —(CH₂)₄— | | —(CH₂)₂— | | Ph |
| —(CH₂)₂—C(=O)—CH₂— | | H | H | Ph |

TABLE 2-continued (Ib) structure

| A | Q | B | B' | R¹ |
|---|---|---|---|---|
| —(CH₂)₂—C(=N—OCH₃)—CH₂— | | H | H | Ph |

TABLE 3

(Ic) structure: with R²—M—C(=L)—O— group

| A | Q | B | B' | L | M | R² |
|---|---|---|---|---|---|---|
| —CH₂— | | H | H | O | O | CH₃ |
| —(CH₂)₂— | | H | H | O | O | CH₃ |
| —CH(CH₃)—CH(CH₃)— | | H | H | O | O | CH₃ |
| —(CH₂)₂— | | CH₃ | CH₃ | O | O | CH₃ |
| —(CH₂)₃— | | H | H | O | O | CH₃ |
| —(CH₂)₂—CHCH₃— | | H | H | O | O | CH₃ |
| —(CH₂)₂—CHOCH₃— | | H | H | O | O | CH₃ |
| —CH₂—CHCH₃—CH₂— | | H | H | O | O | CH₃ |
| —CH₂—CHOCH₃—CH₂— | | H | H | O | O | CH₃ |
| —CH₂—CHCH₃—CHCH₃— | | H | H | O | O | CH₃ |
| —CH₂—CHOCH₃—CHOCH₃— | | H | H | O | O | CH₃ |
| —(CH₂)₄— | | H | H | O | O | CH₃ |
| —(CH₂)₃—CHCH₃— | | H | H | O | O | CH₃ |
| —(CH₂)₃—CHOCH₃— | | H | H | O | O | CH₃ |
| —(CH₂)₂—CHCH₃—CH₂— | | H | H | O | O | CH₃ |
| —(CH₂)₂—CHOCH₃—CH₂— | | H | H | O | O | CH₃ |
| —(CH₂)₃—CHCH₃— | | H | H | O | O | CH₃ |
| —(CH₂)₃—CHOCH₃— | | H | H | O | O | CH₃ |
| —(CH₂)₄— | | CH₃ | H | O | O | CH₃ |

TABLE 3-continued

[Structure (Ic): cyclopentanone ring fused with A-B bridge and Q-B' substituent, bearing R²-M-C(=O)-O- group and 2,6-dimethylphenyl with additional CH₃ substituent]

| A | Q | B | B' | L | M | R² |
|---|---|---|---|---|---|---|
| —CH₂—CHCH₃—CHCH₃—CH₂— | | H | H | O | O | CH₃ |
| —(CH₂)₂—CHCH₃—CHCH₃— | | H | H | O | O | CH₃ |
| —(CH₂)₂—CHOH—CH₂— | | H | H | O | O | CH₃ |
| —CH₂—CHOH—CHOH—CH₂— | | H | H | O | O | CH₃ |
| —CH₂—CH(—O—CH₂—O—)CH—CH₂— | | H | H | O | O | CH₃ |
| —CH₂—CH(—O—C(CH₃)₂—O—)CH—CH₂— | | H | H | O | O | CH₃ |
| —(CH₂)₄— | | —CH₂— | | O | O | CH₃ |
| —(CH₂)₄— | | —(CH₂)₂— | | O | O | CH₃ |
| —(CH₂)₂—C(=O)—CH₂— | | H | H | O | O | CH₃ |
| —(CH₂)₂—C(=N—OCH₃)—CH₂— | | H | H | O | O | CH₃ |
| —CH₂— | | H | H | O | O | i-C₃H₇ |
| —(CH₂)₂— | | H | H | O | O | i-C₃H₇ |
| —CH(CH₃)—CH(CH₃)— | | H | H | O | O | i-C₃H₇ |
| —(CH₂)₂— | | CH₃ | CH₃ | O | O | i-C₃H₇ |
| —(CH₂)₃— | | H | H | O | O | i-C₃H₇ |
| —(CH₂)₂—CHCH₃— | | H | H | O | O | i-C₃H₇ |
| —(CH₂)₂—CHOCH₃— | | H | H | O | O | i-C₃H₇ |
| —CH₂—CHCH₃—CH₂— | | H | H | O | O | i-C₃H₇ |
| —CH₂—CHOCH₃—CH₂— | | H | H | O | O | i-C₃H₇ |
| —CH₂—CHCH₃—CHCH₃ | | H | H | O | O | i-C₃H₇ |
| —CH₂—CHOCH₃—CHOCH₃ | | H | H | O | O | i-C₃H₇ |
| —(CH₂)₄— | | H | H | O | O | i-C₃H₇ |
| —(CH₂)₃—CHCH₃— | | H | H | O | O | i-C₃H₇ |
| —(CH₂)₃—CHOCH₃— | | H | H | O | O | i-C₃H₇ |
| —(CH₂)₂—CHCH₃—CH₂— | | H | H | O | O | i-C₃H₇ |
| —(CH₂)₂—CHOCH₃—CH₂— | | H | H | O | O | i-C₃H₇ |
| —(CH₂)₃—CHCH₃— | | H | H | O | O | i-C₃H₇ |
| —(CH₂)₃—CHOCH₃— | | H | H | O | O | i-C₃H₇ |
| —(CH₂)₄— | | CH₃ | H | O | O | i-C₃H₇ |
| —CH₂—CHCH₃—CHCH₃—CH₂— | | H | H | O | O | i-C₃H₇ |
| —(CH₂)₂—CHCH₃—CHCH₃— | | H | H | O | O | i-C₃H₇ |
| —(CH₂)₂—CHOH—CH₂— | | H | H | O | O | i-C₃H₇ |
| —CH₂—CHOH—CHOH—CH₂ | | H | H | O | O | i-C₃H₇ |
| —CH₂—CH(—O—CH₂—O—)CH—CH₂— | | H | H | O | O | i-C₃H₇ |
| —CH₂—CH(—O—C(CH₃)₂—O—)CH—CH₂— | | H | H | O | O | i-C₃H₇ |
| —(CH₂)₄— | | —CH₂— | | O | O | i-C₃H₇ |
| —(CH₂)₄— | | —(CH₂)₂— | | O | O | i-C₃H₇ |

TABLE 3-continued (Ic) structure: cyclopentenone with A-B ring closure at position bearing Q, B'; R²—M—C(=O)—O— attached to enol carbon; 2,6-dimethyl-4-methylphenyl (2,3,6-trimethylphenyl actually — with CH₃ at positions showing 2,6 and para CH₃) aryl substituent.

| A | Q | B | B' | L | M | R² |
|---|---|---|----|---|---|----|
| —(CH₂)₂—C(=O)—CH₂— | | H | H | O | O | i-C₃H₇ |
| —(CH₂)₂—C(=N—OCH₃)—CH₂— | | H | H | O | O | i-C₃H₇ |
| —CH₂— | | H | H | O | O | i-C₄H₉ |
| —(CH₂)₂— | | H | H | O | O | i-C₄H₉ |
| —CH(CH₃)—CH(CH₃)— | | H | H | O | O | i-C₄H₉ |
| —(CH₂)₂— | | CH₃ | CH₃ | O | O | i-C₄H₉ |
| —(CH₂)₃— | | H | H | O | O | i-C₄H₉ |
| —(CH₂)₂—CHCH₃— | | H | H | O | O | i-C₄H₉ |
| —(CH₂)₂—CHOCH₃— | | H | H | O | O | i-C₄H₉ |
| —CH₂—CHCH₃—CH₂— | | H | H | O | O | i-C₄H₉ |
| —CH₂—CHOCH₃—CH₂— | | H | H | O | O | i-C₄H₉ |
| —CH₂—CHCH₃—CHCH₃— | | H | H | O | O | i-C₄H₉ |
| —CH₂—CHOCH₃—CHOCH₃ | | H | H | O | O | i-C₄H₉ |
| —(CH₂)₄— | | H | H | O | O | i-C₄H₉ |
| —(CH₂)₃—CHCH₃— | | H | H | O | O | i-C₄H₉ |
| —(CH₂)₃—CHOCH₃— | | H | H | O | O | i-C₄H₉ |
| —(CH₂)₂—CHCH₃—CH₂— | | H | H | O | O | i-C₄H₉ |
| —(CH₂)₂—CHOCH₃—CH₂— | | H | H | O | O | i-C₄H₉ |
| —(CH₂)₃—CHCH₃— | | H | H | O | O | i-C₄H₉ |
| —(CH₂)₃—CHOCH₃— | | H | H | O | O | i-C₄H₉ |
| —(CH₂)₄— | | CH₃ | H | O | O | i-C₄H₉ |
| —CH₂—CHCH₃—CHCH₃—CH₂— | | H | H | O | O | i-C₄H₉ |
| —(CH₂)₂—CHCH₃—CHCH₃— | | H | H | O | O | i-C₄H₉ |
| —(CH₂)₂—CHOH—CH₂— | | H | H | O | O | i-C₄H₉ |
| —CH₂—CHOH—CHOH—CH₂ | | H | H | O | O | i-C₄H₉ |
| —CH₂—CH(—O—CH₂—O—)CH—CH₂— | | H | H | O | O | i-C₄H₉ |
| —CH₂—CH(—O—C(CH₃)₂—O—)CH—CH₂— | | H | H | O | O | i-C₄H₉ |
| —(CH₂)₄— | | —CH₂— | | O | O | i-C₄H₉ |
| —(CH₂)₄— | | —(CH₂)₂— | | O | O | i-C₄H₉ |
| —(CH₂)₂—C(=O)—CH₂— | | H | H | O | O | i-C₄H₉ |
| —(CH₂)₂—C(=N—OCH₃)—CH₂— | | H | H | O | O | i-C₄H₉ |
| —CH₂— | | H | H | O | O | Ph (=Phenyl) |
| —(CH₂)₂— | | H | H | O | O | Ph |
| —CH(CH₃)—CH(CH₃)— | | H | H | O | O | Ph |
| —(CH₂)₂— | | CH₃ | CH₃ | O | O | Ph |
| —(CH₂)₃— | | H | H | O | O | Ph |

TABLE 3-continued (Ic) structure: cyclopentanone with 2,6-dimethylphenyl (also with CH3 at position), R²—M—C(=O)—O— attached, A and B substituents on ring, Q B' group.

| A | Q | B | B' | L | M | R² |
|---|---|---|----|---|---|-----|
| —(CH₂)₂—CHCH₃— | | H | H | O | O | Ph |
| —(CH₂)₂—CHOCH₃— | | H | H | O | O | Ph |
| —CH₂—CHCH₃—CH₂— | | H | H | O | O | Ph |
| —CH₂—CHOCH₃—CH₂— | | H | H | O | O | Ph |
| —CH₂—CHCH₃—CHCH₃— | | H | H | O | O | Ph |
| —CH₂—CHOCH₃—CHOCH₃— | | H | H | O | O | Ph |
| —(CH₂)₄— | | H | H | O | O | Ph |
| —(CH₂)₃—CHCH₃— | | H | H | O | O | Ph |
| —(CH₂)₃—CHOCH₃— | | H | H | O | O | Ph |
| —(CH₂)₂—CHCH₃—CH₂— | | H | H | O | O | Ph |
| —(CH₂)₂—CHOCH₃—CH₂— | | H | H | O | O | Ph |
| —(CH₂)₃—CHCH₃— | | H | H | O | O | Ph |
| —(CH₂)₃—CHOCH₃— | | H | H | O | O | Ph |
| —(CH₂)₄— | | CH₃ | H | O | O | Ph |
| —CH₂—CHCH₃—CHCH₃CH₂— | | H | H | O | O | Ph |
| —(CH₂)₂—CHCH₃—CHCH₃— | | H | H | O | O | Ph |
| —(CH₂)₂—CHOH—CH₂— | | H | H | O | O | Ph |
| —CH₂—CHOH—CHOH—CH₂— | | H | H | O | O | Ph |
| —CH₂—CH(—O—CH₂—O—)CH—CH₂— | | H | H | O | O | Ph |
| —CH₂—CH(—O—C(CH₃)₂—O—)CH—CH₂— | | H | H | O | O | Ph |
| —(CH₂)₄— | | —CH₂— | | O | O | Ph |
| —(CH₂)₄— | | —(CH₂)₂— | | O | O | Ph |
| —(CH₂)₂—C(=O)—CH₂— | | H | H | O | O | Ph |
| —(CH₂)₂—C(=N—OCH₃)—CH₂— | | H | H | O | O | Ph |
| —CH₂— | | H | H | O | O | Bz (=Benzyl) |
| —(CH₂)₂— | | H | H | O | O | Bz |
| —CH(CH₃)—CH(CH₃)— | | H | H | O | O | Bz |
| —(CH₂)₂— | | CH₃ | CH₃ | O | O | Bz |
| —(CH₂)₃— | | H | H | O | O | Bz |
| —(CH₂)₂—CHCH₃— | | H | H | O | O | Bz |
| —(CH₂)₂—CHOCH₃— | | H | H | O | O | Bz |
| —CH₂—CHCH₃—CH₂— | | H | H | O | O | Bz |
| —CH₂—CHOCH₃—CH₂— | | H | H | O | O | Bz |
| —CH₂—CHCH₃—CHCH₃— | | H | H | O | O | Bz |
| —CH₂—CHOCH₃—CHOCH₃— | | H | H | O | O | Bz |
| —(CH₂)₄— | | H | H | O | O | Bz |
| —(CH₂)₃—CHCH₃— | | H | H | O | O | Bz |
| —(CH₂)₃—CHOCH₃— | | H | H | O | O | Bz |
| —(CH₂)₂—CHCH₃—CH₂— | | H | H | O | O | Bz |
| —(CH₂)₂—CHOCH₃—CH₂— | | H | H | O | O | Bz |
| —(CH₂)₃—CHCH₃— | | H | H | O | O | Bz |
| —(CH₂)₃—CHOCH₃— | | H | H | O | O | Bz |
| —(CH₂)₄— | | CH₃ | H | O | O | Bz |
| —CH₂—CHCH₃—CHCH₃—CH₂— | | H | H | O | O | Bz |
| —(CH₂)₂—CHCH₃—CHCH₃— | | H | H | O | O | Bz |

TABLE 3-continued (Ic) structure: cyclopentenone with A-B substituted carbon, Q-B' bearing ketone, R²-M-C(=O)-O- enol ester, and 2,6-dimethyl (with additional CH₃) phenyl group.

| A | Q | B | B' | L | M | R² |
|---|---|---|---|---|---|---|
| —(CH₂)₂—CHOH—CH₂— | | H | H | O | O | Bz |
| —CH₂—CHOH—CHOH—CH₂— | | H | H | O | O | Bz |
| —CH₂—CH—CH—CH₂— (O—CH₂—O bridge) | | H | H | Q | O | Bz |
| —CH₂—CH—CH—CH₂— (O—C(CH₃)₂—O bridge) | | H | H | O | O | Bz |
| —(CH₂)₄— | | —CH₂— | | O | O | Bz |
| —(CH₂)₄— | | —(CH₂)₂— | | O | O | Bz |
| —(CH₂)₂—C(=O)—CH₂— | | H | H | O | O | Bz |
| —(CH₂)₂—C(=N—OCH₃)—CH₂— | | H | H | O | O | Bz |
| —CH₂— | | H | H | O | S | i-C₃H₇ |
| —(CH₂)₂— | | H | H | O | S | i-C₃H₇ |
| —CH(CH₃)—CH(CH₃)— | | H | H | O | S | i-C₃H₇ |
| —(CH₂)₂— | | CH₃ | CH₃ | O | S | i-C₃H₇ |
| —(CH₂)₃— | | H | H | O | S | i-C₃H₇ |
| —(CH₂)₂—CHCH₃— | | H | H | O | S | i-C₃H₇ |
| —(CH₂)₂—CHOCH₃— | | H | H | O | S | i-C₃H₇ |
| —CH₂—CHCH₃—CH₂— | | H | H | O | S | i-C₃H₇ |
| —CH₂—CHOCH₃—CH₂— | | H | H | O | S | i-C₃H₇ |
| —CH₂—CHCH₃—CHCH₃— | | H | H | O | S | i-C₃H₇ |
| —CH₂—CHOCH₃—CHOCH₃— | | H | H | O | S | i-C₃H₇ |
| —(CH₂)₄— | | H | H | O | S | i-C₃H₇ |
| —(CH₂)₃—CHCH₃— | | H | H | O | S | i-C₃H₇ |
| —(CH₂)₃—CHOCH₃— | | H | H | O | S | i-C₃H₇ |
| —(CH₂)₂—CHCH₃—CH₃— | | H | H | O | S | i-C₃H₇ |
| —(CH₂)₂—CHOCH₃—CH₂— | | H | H | O | S | i-C₃H₇ |
| —(CH₂)₃—CHCH₃— | | H | H | O | S | i-C₃H₇ |
| —(CH₂)₃—CHOCH₃— | | H | H | O | S | i-C₃H₇ |
| —(CH₂)₄— | | CH₃ | H | O | S | i-C₃H₇ |
| —CH₂—CHCH₃—CHCH₃—CH₂— | | H | H | O | S | i-C₃H₇ |
| —(CH₂)₂—CHCH₃—CHCH₃— | | H | H | O | S | i-C₃H₇ |
| —(CH₂)₂—CHOH—CH₂— | | H | H | O | S | i-C₃H₇ |
| —CH₂—CHOH—CHOH—CH₂— | | H | H | O | S | i-C₃H₇ |
| —CH₂—CH—CH—CH₂— (O—CH₂—O bridge) | | H | H | O | S | i-C₃H₇ |
| —CH₂—CH—CH—CH₂— (O—C(CH₃)₂—O bridge) | | H | H | O | S | i-C₃H₇ |
| —(CH₂)₄— | | —CH₂— | | O | S | i-C₃H₇ |
| —(CH₂)₄ | | —(CH₂)₂— | | O | S | i-C₃H₇ |
| —(CH₂)₂—C(=O)—CH₂— | | H | H | O | S | i-C₃H₇ |

TABLE 3-continued (Ic) structure: cyclopentenone with A, B, B', Q substituents on ring, ketone (=O), R²-M-C(=O)-O- group, and 2,6-dimethyl-... aryl group with CH₃ substituents.

| A | Q | B | B' | L | M | R² |
|---|---|---|---|---|---|---|
| —(CH₂)₂—C(=N—OCH₃)—CH₂— | | H | H | O | S | i-C₃H₇ |
| —CH₂— | | H | H | O | S | t-C₄H₉ |
| —(CH₂)₂— | | H | H | O | S | t-C₄H₉ |
| —CH(CH₃)—CH(CH₃)— | | H | H | O | S | t-C₄H₉ |
| —(CH₂)₂— | | CH₃ | CH₃ | O | S | t-C₄H₉ |
| —(CH₂)₃— | | H | H | O | S | t-C₄H₉ |
| —(CH₂)₂—CHCH₃— | | H | H | O | S | t-C₄H₉ |
| —(CH₂)₂—CHOCH₃— | | H | H | O | S | t-C₄H₉ |
| —CH₂—CHCH₃—CH₂— | | H | H | O | S | t-C₄H₉ |
| —CH₂—CHOCH₃—CH₂— | | H | H | O | S | t-C₄H₉ |
| —CH₂—CHCH₃—CHCH₃— | | H | H | O | S | t-C₄H₉ |
| —CH₂—CHOCH₃—CHOCH₃— | | H | H | O | S | t-C₄H₉ |
| —(CH₂)₄— | | H | H | O | S | t-C₄H₉ |
| —(CH₂)₃—CHCH₃— | | H | H | O | S | t-C₄H₉ |
| —(CH₂)₃—CHOCH₃— | | H | H | O | S | t-C₄H₉ |
| —(CH₂)₂—CHCH₃—CH₂— | | H | H | O | S | t-C₄H₉ |
| —(CH₂)₂—CHOCH₃—CH₂— | | H | H | O | S | t-C₄H₉ |
| —(CH₂)₃—CHCH₃— | | H | H | O | S | t-C₄H₉ |
| —(CH₂)₃—CHOCH₃— | | H | H | O | S | t-C₄H₉ |
| —(CH₂)₄— | | CH₃ | H | O | S | t-C₄H₉ |
| —CH₂—CHCH₃—CHCH₃—CH₂— | | H | H | O | S | t-C₄H₉ |
| —(CH₂)₂—CHCH₃—CHCH₃— | | H | H | O | S | t-C₄H₉ |
| —(CH₂)₂—CHOH—CH₂— | | H | H | O | S | t-C₄H₉ |
| —CH₂—CHOH—CHOH—CH₂— | | H | H | O | S | t-C₄H₉ |
| —CH₂—CH(—O—CH₂—O—)CH—CH₂— | | H | H | O | S | t-C₄H₉ |
| —CH₂—CH(—O—C(CH₃)₂—O—)CH—CH₂— | | H | H | O | S | t-C₄H₉ |
| —(CH₂)₄— | | —CH₂— | | O | S | t-C₄H₉ |
| —(CH₂)₄— | | —(CH₂)₂— | | O | S | t-C₄H₉ |
| —(CH₂)₂—C(=O)—CH₂— | | H | H | O | S | t-C₄H₉ |
| —(CH₂)₂—C(=N—OCH₃)—CH₂— | | H | H | O | S | t-C₄H₉ |

TABLE 4

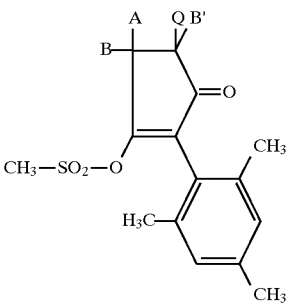
(Id)

| A Q | B | B' |
|---|---|---|
| —CH₂— | H | H |
| —(CH₂)₂— | H | H |
| —CH(CH₃)—CH(CH₃)— | H | H |
| —(CH₂)₂— | CH₃ | CH₃ |
| —(CH₂)₃— | H | H |
| —(CH₂)₂—CHCH₃— | H | H |
| —(CH₂)₂—CHOCH₃— | H | H |
| —CH₂—CHCH₃—CH₂— | H | H |
| —CH₂—CHOCH₃—CH₂— | H | H |
| —CH₂—CHCH₃—CHCH₃— | H | H |
| —CH₂—CHOCH₃—CHOCH₃— | H | H |
| —(CH₂)₄— | H | H |
| —(CH₂)₃—CHCH₃— | H | H |
| —(CH₂)₃—CHOCH₃— | H | H |
| —(CH₂)₂—CHCH₃—CH₂— | H | H |
| —(CH₂)₂—CHOCH₃—CH₂— | H | H |
| —(CH₂)₃—CHCH₃— | H | H |
| —(CH₂)₃—CHOCH₃— | H | H |
| —(CH₂)₄— | CH₃ | H |
| —CH₂—CHCH₃—CHCH₃—CH₂— | H | H |
| —(CH₂)₂—CHCH₃—CHCH₃— | H | H |
| —(CH₂)₂—CHOH—CH₂— | H | H |
| —CH₂—CHOH—CHOH—CH₂— | H | H |
| —CH₂—CH(—O—CH₂—O—)CH—CH₂— | H | H |
| —CH₂—CH(—O—C(CH₃)₂—O—)CH—CH₂— | H | H |
| —(CH₂)₄— | —CH₂— | |
| —(CH₂)₄— | —(CH₂)₂— | |
| —(CH₂)₂—C(=O)—CH₂— | H | H |
| —(CH₂)₂—C(=N—OCH₃)—CH₂— | H | H |

TABLE 5

| A | Q | B | B' |
|---|---|---|---|

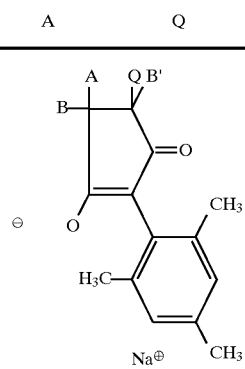
(If)

| A Q | B | B' |
|---|---|---|
| —CH₂— | H | H |
| —(CH₂)₂— | H | H |
| —CH(CH₃)—CH(CH₃)— | H | H |
| —(CH₂)₂— | CH₃ | CH₃ |
| —(CH₂)₃— | H | H |
| —(CH₂)₂—CHCH₃— | H | H |
| —(CH₂)₂—CHOCH₃— | H | H |
| —CH₂—CHCH₃—CH₂— | H | H |
| —CH₂—CHOCH₃—CH₂— | H | H |
| —CH₂—CHCH₃—CHCH₃— | H | H |
| —CH₂—CHOCH₃—CHOCH₃— | H | H |
| —(CH₂)₄— | H | H |
| —(CH₂)₃—CHCH₃— | H | H |
| —(CH₂)₃—CHOCH₃— | H | H |
| —(CH₂)₂—CHCH₃—CH₂— | H | H |
| —(CH₂)₂—CHOCH₃—CH₂— | H | H |
| —(CH₂)₃—CHCH₃— | H | H |
| —(CH₂)₃—CHOCH₃— | H | H |
| —(CH₂)₄— | CH₃ | H |
| —CH₂—CHCH₃—CHCH₃—CH₂— | H | H |
| —(CH₂)₂—CHCH₃—CHCH₃— | H | H |
| —(CH₂)₂—CHOH—CH₂— | H | H |
| —CH₂—CHOH—CHOH—CH₂— | H | H |
| —CH₂—CH(—O—CH₂—O—)CH—CH₂— | H | H |
| —CH₂—CH(—O—C(CH₃)₂—O—)CH—CH₂— | H | H |
| —(CH₂)₄— | —CH₂— | |
| —(CH₂)₄— | —(CH₂)₂— | |
| —(CH₂)₂—C(=O)—CH₂— | H | H |
| —(CH₂)₂—C(=N—OCH₃)—CH₂— | H | H |

TABLE 5-continued

| A | Q | B | B' |
|---|---|---|---|

(Ia) [structure: cyclopentanedione with 2,4,6-trimethylphenyl group, O⁻, and CH₃CH(NH₃⁺)CH₃ counterion]

| | —CH₂— | H | H |
| | —(CH₂)₂— | H | H |
| | —CH(CH₃)—CH(CH₃)— | H | H |
| | —(CH₂)₂— | CH₃ | CH₃ |
| | —(CH₂)₃— | H | H |
| | —(CH₂)₂—CHCH₃— | H | H |
| | —(CH₂)₂—CHOCH₃— | H | H |
| | —CH₂—CHCH₃—CH₂— | H | H |
| | —CH₂—CHOCH₃—CH₂— | H | H |
| | —CH₂—CHCH₃—CHCH₃— | H | H |
| | —CH₂—CHOCH₃—CHOCH₃— | H | H |
| | —(CH₂)₄— | H | H |
| | —(CH₂)₃—CHCH₃— | H | H |
| | —(CH₂)₃—CHOCH₃— | H | H |
| | —(CH₂)₂—CHCH₃—CH₂— | H | H |
| | —(CH₂)₂—CHOCH₃—CH₂— | H | H |
| | —(CH₂)₃—CHCH₃— | H | H |
| | —(CH₂)₃—CHOCH₃— | H | H |
| | —(CH₂)₄— | CH₃ | H |
| | —CH₂—CHCH₃—CHCH₃—CH₂— | H | H |
| | —(CH₂)₂—CHCH₃—CHCH₃— | H | H |
| | —(CH₂)₂—CHOH—CH₂— | H | H |
| | —CH₂—CHOH—CHOH—CH₂— | H | H |
| | —CH₂—CH(O—CH₂—O)CH—CH₂— | H | H |
| | —CH₂—CH(O—C(CH₃)₂—O)CH—CH₂— | H | H |
| | —(CH₂)₄— | —CH₂— | |
| | —(CH₂)₄— | —(CH₂)₂— | |
| | —(CH₂)₂—C(=O)—CH₂— | H | H |
| | —(CH₂)₂—C(=N—OCH₃)—CH₂— | H | H |

TABLE 6

| A | Q | B | B' |
|---|---|---|---|

(Ig) [structure: cyclopentanedione with N,N-dimethylcarbamate and 2,4,6-trimethylphenyl group]

| | —CH₂— | H | H |
| | —(CH₂)₂— | H | H |
| | —CH(CH₃)—CH(CH₃)— | H | H |
| | —(CH₂)₂— | CH₃ | CH₃ |
| | —(CH₂)₃— | H | H |
| | —(CH₂)₂—CHCH₃— | H | H |
| | —(CH₂)₂—CHOCH₃— | H | H |
| | —CH₂—CHCH₃—CH₂— | H | H |
| | —CH₂—CHOCH₃—CH₂— | H | H |
| | —CH₂—CHCH₃—CHCH₃— | H | H |
| | —CH₂—CHOCH₃—CHOCH₃— | H | H |
| | —(CH₂)₄— | H | H |
| | —(CH₂)₃—CHCH₃— | H | H |
| | —(CH₂)₃—CHOCH₃— | H | H |
| | —(CH₂)₂—CHCH₃—CH₂— | H | H |
| | —(CH₂)₂—CHOCH₃—CH₂— | H | H |
| | —(CH₂)₃—CHCH₃— | H | H |
| | —(CH₂)₃—CHOCH₃— | H | H |
| | —(CH₂)₄— | CH₃ | H |
| | —CH₂—CHCH₃—CHCH₃—CH₂— | H | H |
| | —(CH₂)₂—CHCH₃—CHCH₃— | H | H |
| | —(CH₂)₂—CHOH—CH₂— | H | H |
| | —CH₂—CHOH—CHOH—CH₂— | H | H |
| | —CH₂—CH(O—CH₂—O)CH—CH₂— | H | H |
| | —CH₂—CH(O—C(CH₃)₂—O)CH—CH₂— | H | H |
| | —(CH₂)₄— | —CH₂— | |
| | —(CH₂)₄— | —(CH₂)₂— | |
| | —(CH₂)₂—C(=O)—CH₂— | H | H |
| | —(CH₂)₂—C(=N—OCH₃)—CH₂— | H | H |

(Ig) [structure: cyclopentanedione with morpholine carbamate and 2,4,6-trimethylphenyl group]

| | —CH₂— | H | H |

TABLE 6-continued

| A | Q | B | B' |
|---|---|---|---|
| —(CH$_2$)$_2$— | | H | H |
| —CH——CH—<br>    |        |<br>  CH$_3$   CH$_3$ | | H | H |
| —(CH$_2$)$_2$— | | CH$_3$ | CH$_3$ |
| —(CH$_2$)$_3$— | | H | H |
| —(CH$_2$)$_2$—CHCH$_3$— | | H | H |
| —(CH$_2$)$_2$—CHOCH$_3$— | | H | H |
| —CH$_2$—CHCH$_3$—CH$_2$— | | H | H |
| —CH$_2$—CHOCH$_3$—CH$_2$— | | H | H |
| —CH$_2$—CHCH$_3$—CHCH$_3$— | | H | H |
| —CH$_2$—CHOCH$_3$—CHOCH$_3$— | | H | H |
| —(CH$_2$)$_4$— | | H | H |
| —(CH$_2$)$_3$—CHCH$_3$— | | H | H |
| —(CH$_2$)$_3$—CHOCH$_3$— | | H | H |
| —(CH$_2$)$_2$—CHCH$_3$—CH$_2$— | | H | H |
| —(CH$_2$)$_2$—CHOCH$_3$—CH$_2$— | | H | H |
| —(CH$_2$)$_3$—CHCH$_3$— | | H | H |
| —(CH$_2$)$_3$—CHOCH$_3$— | | H | H |
| —(CH$_2$)$_4$— | | CH$_3$ | H |
| —CH$_2$—CHCH$_3$—CHCH$_3$—CH$_2$— | | H | H |
| —(CH$_2$)$_2$—CHCH$_3$—CHCH$_3$— | | H | H |
| —(CH$_2$)$_2$—CHOH—CH$_2$— | | H | H |
| —CH$_2$—CHOH—CHOH—CH$_2$— | | H | H |
| —CH$_2$—CH————CH—CH$_2$—<br>         |          |<br>         O—CH$_2$—O | | H | H |
| —CH$_2$—CH————CH—CH$_2$—<br>         |          |<br>        O—C(CH$_3$)$_2$—O | | H | H |
| —(CH$_2$)$_4$— | | —CH$_2$— | |
| —(CH$_2$)$_4$— | | —(CH$_2$)$_2$— | |
| —(CH$_2$)$_2$—C—CH$_2$—<br>         ||<br>         O | | H | H |
| —(CH$_2$)$_2$—C—CH$_2$—<br>         ||<br>       N—OCH$_3$ | | H | H |

If ethyl 5-(2,4,6-trimethylphenyl)-2,3-tetramethylene-4-oxo-valerate is used according to process (A) the course of the process according to the invention can be represented by the following equation:

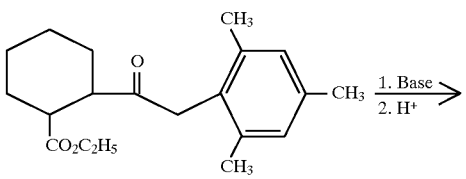

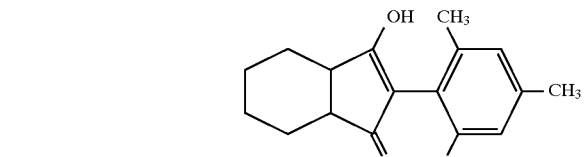

If 2-(2,4,6-trimethylphenyl)-4,5-(2,3-dimethyl)-tetramethylene-3-hydroxy-2-cyclopenten-1-one and piv-aloyl chloride are used as starting substances according to process (B) (variant α), the course of the process according to the invention can be represented by the following equation:

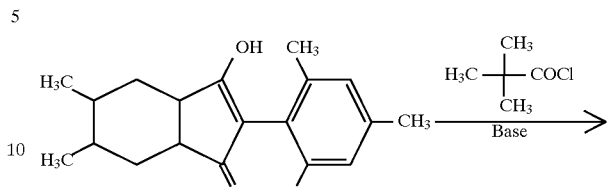

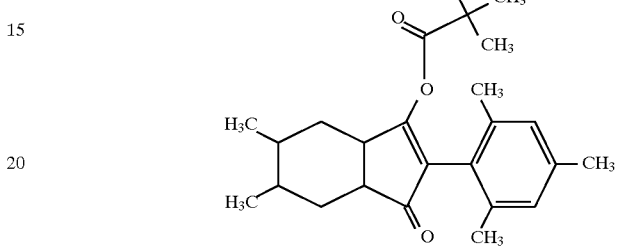

If 2-(2,4,6-trimethylphenyl)-4,5-methylene-3-hydroxy-2-cyclopenten-1-one and acetic anhydride are used as starting compounds according to process B (variant β), the course of the process according to the invention can be represented by the following equation:

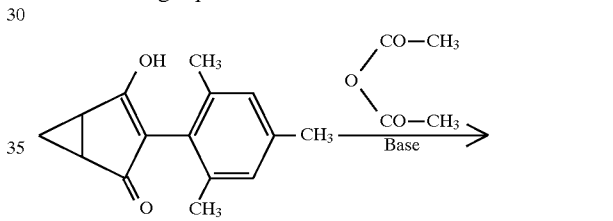

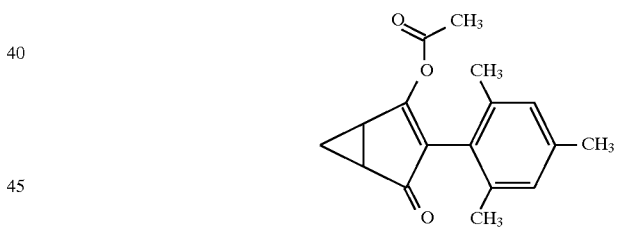

If 2-(2,4,6-trimethylphenyl)-4,5-(3-oxo)-tetramethylene-3-hydroxy-2-cyclopenten-1-one and ethoxyethyl chloroformate are used as starting compounds according to process C, the course of the process according to the invention can be represented by the following equation:

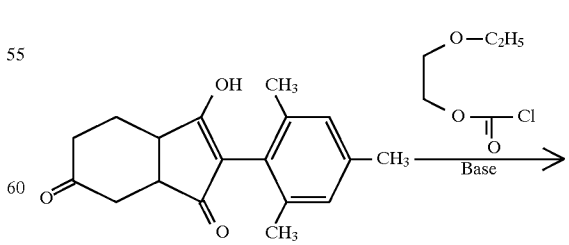

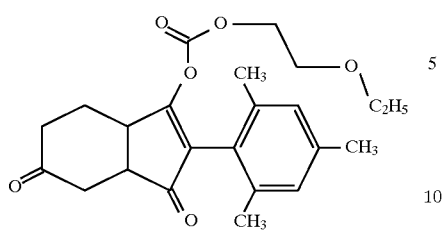

If 2-(2,4,6-trimethylphenyl)-4,5-(3-methyl)-tetramethylene-3-hydroxy-2-cyclopenten-1-one and methyl chloromonothioformate are used as starting substances according to process ($D_\alpha$), the course of the reaction can be represented as follows:

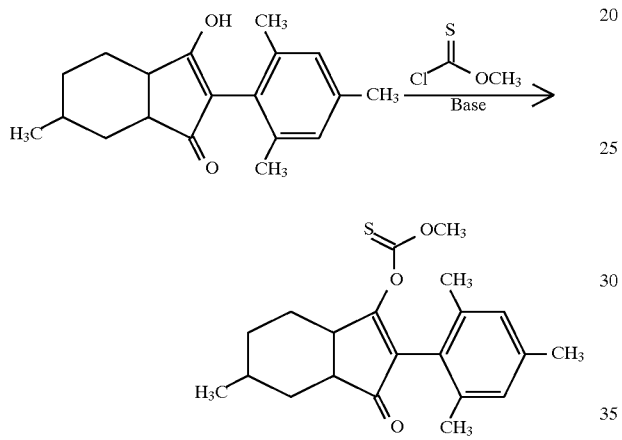

If 2-(2,4,6-trimethylphenyl)-4,5-trimethylene-3-hydroxy-2-cyclopenten-1-one, carbon disulphide and methyl iodide are used as starting components according to process ($D_\beta$), the course of the reaction can be represented as follows:

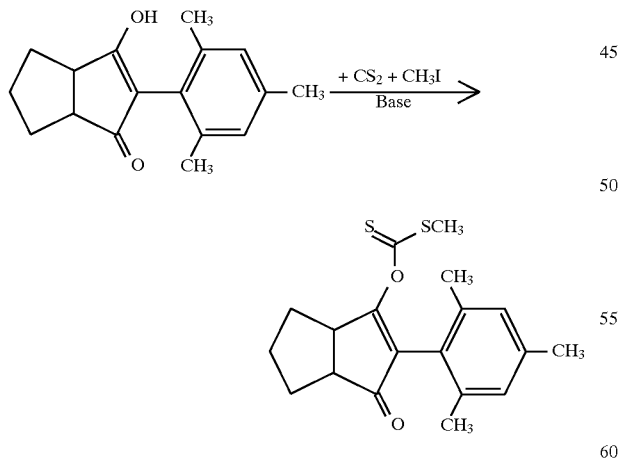

If 2-(2,4,6-trimethylphenyl)-4,5-(3-methoxy)-tetramethylene-3-hydroxy-2-cyclo penten-1-one and methanesulphonyl chloride are used as starting substance according to process (E), the course of the reaction can be represented by the following equation:

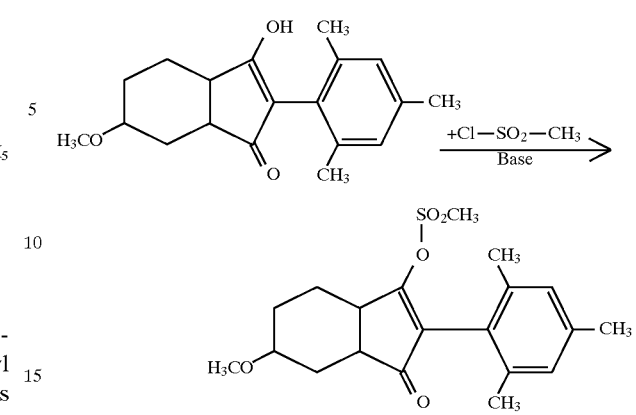

If 2-(2,4,6-trimethylphenyl)-4,5-(4-methyl)-tetramethylene-3-hydroxy-2-cyclopenten-1-one and methanethio-phosphonic acid chloride (2,2,2-trifluoroethyl ester) are used as starting substances according to process (F), the course of the reaction can be represented by the following equation:

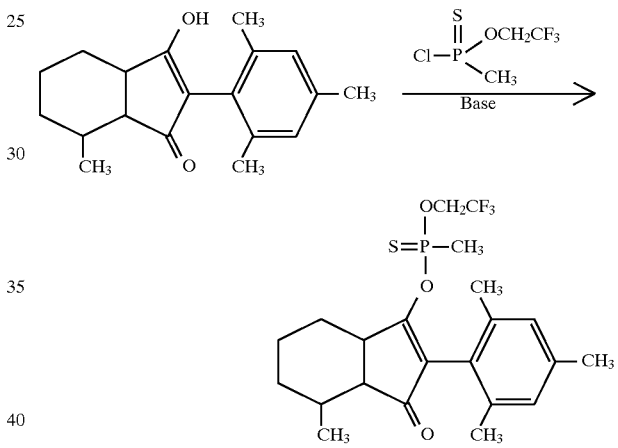

If 2-(2,4,6-trimethylphenyl)-4,5-(3,3-ethylenedioxy)-tetramethylene-3-hydroxy-2-cyclopenten-1-one and NaOH are used as components according to process (G), the course of the process according to the invention can be represented by the following equation:

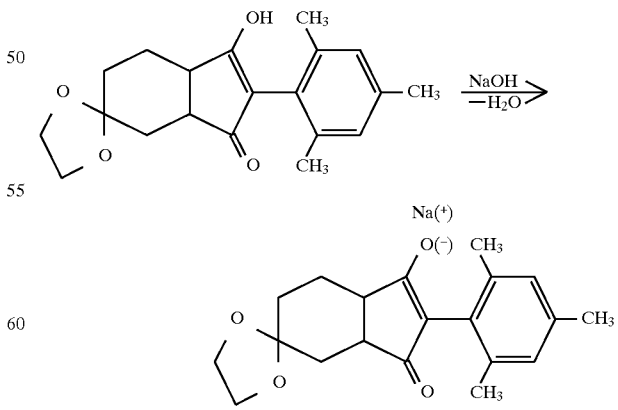

If 2-(2,4,6-trimethylphenyl)-4,5-(3-methoxy)-tetramethylene-3-hydroxy-2-cyclopenten-1-one and ethyl isocyanate are used as starting substances according to process (H$_\alpha$), the course of the reaction can be represented by the following equation:

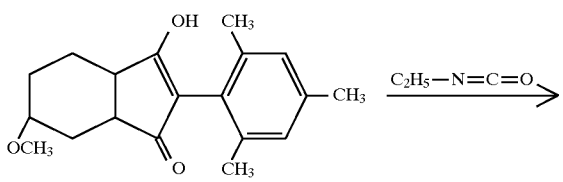

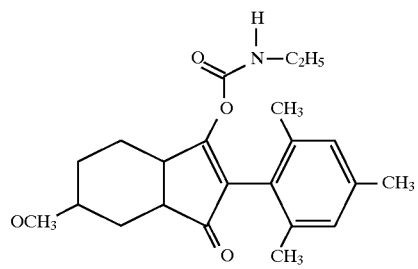

If 2-(2,4,6-trimethylphenyl)-4,5-tertramethylene-3-hydroxy-2-cyclopenten-1-one and dimethylcarbamyl chloride are used as starting substances according to process (H$_\beta$), the course of the reaction can be represented by the following equation:

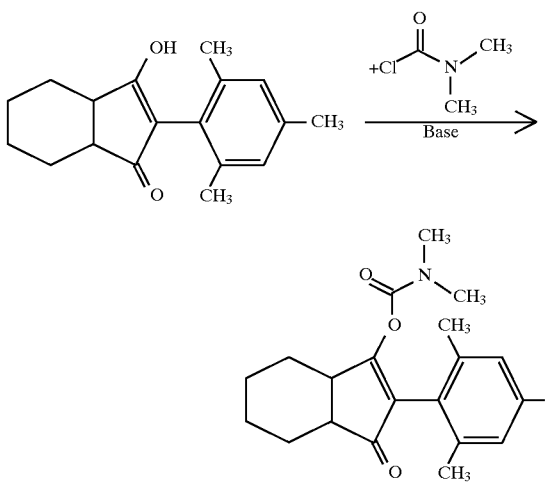

The compounds of the formula (II)

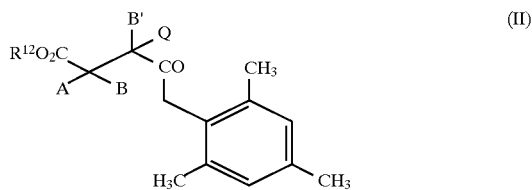

(II)

in which

A, B, B', Q and R$^{12}$ have the abovementioned meaning, required as starting substances in the above process (A) are novel. They can be prepared by methods which are known in principle. The 5-aryl-4-ketocarboxylic acid esters of the formula (II) are obtained, for example, when 5-aryl-4-ketocarboxylic acids of the formula (XIV)

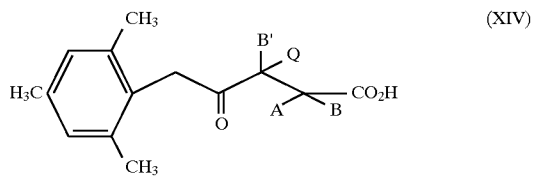

in which

A, B, B' and Q have the abovementioned meaning, are esterified (cf. for example, Organikum, 15th Edition, Berlin, 1977, pages 499).

The 5-aryl-4-ketocarboxylic acids of the formula (XIV)

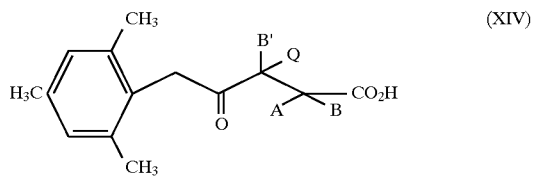

in which

A, B, B' and Q have the abovementioned meaning, are novel, but can be prepared by methods which are known in principle.

The 5-aryl-4-ketocarboxylic acids of the formula (XIV) are obtained, for example, when carboxylic acid anhydrides of the formula (XV)

in which

A, B, B' and Q have the abovementioned meaning, are reacted with organometallic compounds of the formula (XVI)

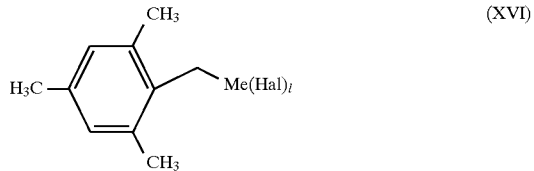

in which

Me represents mono- or divalent metal ions (for example of lithium or magnesium), Hal represents chlorine or bromine and l represents a number 0 or 1 in the presence of a diluent (cf. for example, Organikum, 15th Edition, Berlin, 1977, Page 623).

The compounds (XV) and (XVI) are known in some cases and/or can be prepared in a simple manner by known processes (cf. for example, Organikum, 15th Edition, Berlin, 1977, pages 525, 526 and 623).

5-Aryl-4-ketocarboxylic acids of the formula (XIV)

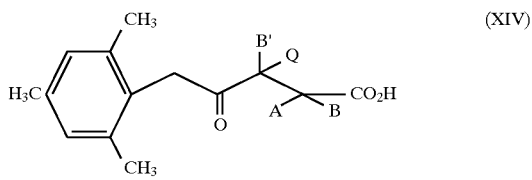

in which

A, B, B' and Q have the abovementioned meaning, furthermore are obtained when 2-mesityl-3-oxo-adipic acid esters of the formula (XVII)

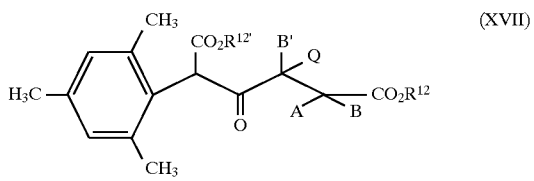

in which

A, B, B' and Q have the abovementioned meaning and $R^{12}$ and $R^{12'}$ represent alkyl (preferably $C_1$–$C_6$-alkyl), are decarboxylated, if appropriate in the presence of a diluent and if appropriate in the presence of a base or acid (cf., for example, Organikum, 15th Edition, Berlin, 1977, pages 519 to 521).

The compounds of the formula (XVII)

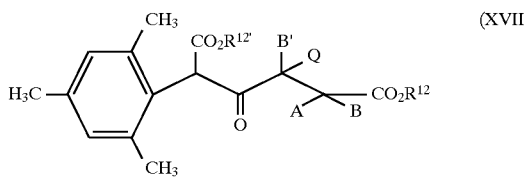

in which

A, B, B', Q, $R^{12}$ and $R^{12'}$ have the abovementioned meaning, are novel and are obtainable when dicarboxylic acid half-ester chlorides of the formula (XVIII)

in which

A, B, B', Q and $R^{12}$ have the abovementioned meaning and

Hal represents chlorine or bromine, are acylated with a substituted phenylacetic acid ester of the formula (XIX)

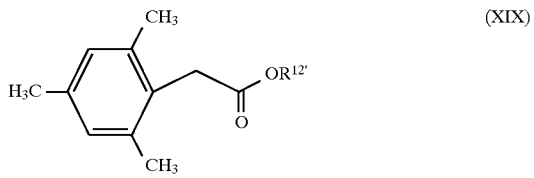

in which $R^{12'}$ represents alkyl, in the presence of a diluent and in the presence of a base (cf., for example, M. S. Chambers, E. J. Thomas, D. J. Williams, J. Chem. Soc. Chem. Commun., (1987), 1228).

The compounds of the formula XVIII and XIX are known in some cases and/or can be prepared by known processes.

Process (A) is characterized in that compounds of the formula (II) in which A, B, B', Q and $R^{12}$ have the abovementioned meaning are subjected to an intra-molecular condensation reaction in the presence of bases.

Diluents which can be employed in process (A) according to the invention are all the organic solvents which are inert towards the reaction participants. Solvents which can preferably be used are hydrocarbons, such as toluene and xylene, and furthermore ethers, such as dibutyl ether, tetrahydrofuran, dioxane, glycol dimethyl ether and diglycol dimethyl ether, and furthermore polar solvents, such as dimethyl sulphoxide, sulpholane, dimethylformamide and N-methyl-pyrrolidone. Alcohols, such as methanol, ethanol, propanol, iso-propanol, butanol, isobutanol, tert-butanol, can moreover be employed.

Bases (deprotonating agents) which can be employed in carrying out process (A) according to the invention are all the customary proton acceptors. Proton acceptors which can preferably be used are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 (methyltrialkyl($C_8$–$C_{10}$)ammonium chloride) or TDA 1 (tris(methoxyethoxyethyl)-amine). Alkali metals, such as sodium or potassium, can moreover be used. It is furthermore possible to employ alkali metal and alkaline earth metal amides and hydrides, such as sodium amide, sodium hydride and calcium hydride, and in addition also alkali metal alcoholates, such as sodium methylate, sodium ethylate and potassium tert-butylate.

The reaction temperatures can be varied within a substantial range in carrying out process (A) according to the invention. The reaction is in general carried out at temperatures between 0° C. and 250° C., preferably between 50° C. and 150° C.

Process (A) according to the invention is in general carried out under normal pressure.

In carrying out process (A) according to the invention, the reaction components of the formula (II) and the deprotonating bases are in general employed in approximately equimolar amounts. However, it is also possible to use one or other of the components in a relatively large excess (up to 3 mol).

Process (Bα) is characterized in that compounds of the formula (Ia) are reacted with carboxylic acid halides of the formula (III).

Diluents which can be employed in process (Bα) according to the invention are all the solvents which are inert towards the acid halides. Solvents which can preferably be used are hydrocarbons, such as benzine, benzene, toluene, xylene and tetralin, and furthermore halogenated hydrocarbons, such as methylene chloride, chloroform, carbon tetrachloride, chlorobenzene and o-dichlorobenzene, and in addition ketones, such as acetone and methyl isopropyl ketone, and furthermore ethers, such as diethyl ether, tetrahydrofuran and dioxane, and additionally carboxylic acid esters, such as ethyl acetate, and also strongly polar solvents, such as dimethyl sulphoxide and sulpholane. If the stability of the acid halide to hydrolysis allows, a reaction can also be carried out in the presence of water.

Possible acid-binding agents in the reaction by process (Bα) according to the invention are all the customary acid acceptors. Acid acceptors which can preferably be used are tertiary amines, such as triethylamine, pyridine, diazabicyclooctane (DABCO), diazabicycloundecane (DBU), diazabicyclononene (DBN), Hünig base and N,N-dimethyl aniline, and furthermore alkaline earth metal oxides, such as magnesium oxide and calcium oxide, and additionally alkali metal and alkaline earth metal carbonates, such as sodium carbonate, potassium carbonate and calcium carbonate.

The reaction temperatures can be varied within a substantial range in process (Bα) according to the invention. The reaction is in general carried out at temperatures between −20° C. and +150° C., preferably between 0° C and 100° C.

In carrying out process (Bα) according to the invention, the starting substances of the formula (Ia) and the carboxylic acid halide of the formula (III) are in general used in approximately equivalent amounts. However, it is also possible to employ the carboxylic acid halide in a relatively large excess (up to 5 mol). Working up is carried out by customary methods.

Process (Bβ) is characterized in that compounds of the formula (Ia) are reacted with carboxylic acid anhydrides of the formula (IV).

Diluents which can be used in process (Bβ) according to the invention are preferably those diluents which are also preferably possible when acid halides are used. In addition, a carboxylic acid anhydride employed in excess can also simultaneously function as the diluent.

The reaction temperatures can be varied within a substantial range in process (Bβ) according to the invention. The reaction is in general carried out at temperatures between −20° C. and +150° C., preferably between 0° C and 100° C.

In carrying out the process according to the invention, the starting substances of the formula (Ia) and the carboxylic acid anhydride of the formula (IV) are in general used in approximately equivalent amounts. However, it is also possible to employ the carboxylic acid anhydride in a relatively large excess (up to 5 mol). Working up is carried out by customary methods.

In general, a procedure is followed in which the diluent and the carboxylic acid anhydride present in excess, as well as the carboxylic acid formed, are removed by distillation or by washing with an organic solvent or with water.

Process (C) is characterized in that compounds of the formula (Ia) are reacted with chloroformic acid esters or chloroformic acid thioesters of the formula (V).

Possible acid-binding agents in the reaction by process (C) according to the invention are all the customary acid acceptors. Acid acceptors which can preferably be used are tertiary amines, such as triethylamine, pyridine, DABCO, DBU, DBN, Hünig base and N,N-dimethylaniline, and furthermore alkaline earth metal oxides, such as magnesium oxide and calcium oxide, and in addition alkali metal and alkaline earth metal carbonates, such as sodium carbonate, potassium carbonate and calcium carbonate.

Diluents which can be employed in process (C) according to the invention are all the solvents which are inert towards the starting substances. Solvents which can preferably be used are hydrocarbons, such as benzine, benzene, toluene, xylene and tetralin, and furthermore halogenated hydrocarbons, such as methylene chloride, chloroform, carbon tetrachloride, chlorobenzene and o-dichlorobenzene, and in addition ketones, such as acetone and methyl isopropyl ketone, and moreover ethers, such as diethyl ether, methyl tert-butyl ether, tetrahydrofuran and dioxane, and additionally carboxylic acid esters, such as ethyl acetate, and also strongly polar solvents, such as dimethyl sulphoxide and sulpholane.

The reaction temperatures can be varied within a substantial range in carrying out process (C) according to the invention. If the reaction is carried out in the presence of a diluent and an acid-binding agent, the reaction temperatures are in general between −20° C. and +100° C., preferably between 0C and 50° C. Process (C) according to the invention is in general carried out under normal pressure.

In carrying out process (C) according to the invention, the starting substances of the formula (Ia) and the corresponding chloroformic acid esters or chloroformic acid thioesters of the formula (V) are in general used in approximately equivalent amounts. However, it is also possible to employ one or other of the components in a relatively large excess (up to 2 mol). Working up is then carried out by customary methods. In general, a procedure is followed in which salts which have precipitated out are removed and the reaction mixture which remains is concentrated by stripping off the diluent.

In preparation process (Dα), about 1 mol of chloromonothioformic acid ester or chlorodithioformic acid ester of the formula (VI) is reacted per mole of starting compound of the formula (Ia) at 0° to 120° C., preferably at 20° to 60° C.

Possible diluents which are optionally added are all the inert organic solvents, such as halogenated hydrocarbons, ethers, amides, alcohols, nitriles, sulphones and sulphoxides.

Acetonitrile, dimethyl sulphoxide, methyl tert-butyl ether, tetrahydrofuran, dimethylformamide, ethyl acetate or methylene chloride are preferably employed.

If, in a preferred embodiment, the enolate salt of the compound of the formula (Ia) is prepared by addition of strong deprotonating agents, such as, for example, sodium hydride or potassium tert-butylate, further addition of acid-binding agents can be omitted.

If acid-binding agents are employed, the customary inorganic or organic bases are possible, and sodium hydroxide, sodium carbonate, potassium carbonate, pyridine and triethylamine may be listed as examples.

The reaction can be carried out under normal pressure or under increased pressure, and is preferably carried out under normal pressure. Working up is carried out by customary methods.

In preparation process (Dβ), the equimolar amount or an excess of carbon disulphide is added per mole of starting compound of the formula (II). This reaction is preferably carried out at temperatures from 0° to 50° C. and in particular at 20° to 30° C.

Bases which can be employed in process (Dβ) are all the customary proton acceptors. Proton acceptors which can preferably be used are alkali metal hydrides, alkali metal alcoholates, alkali metal or alkaline earth metal carbonates or bicarbonates or nitrogen bases. Examples which may be mentioned are sodium hydride, sodium methanolate, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

Diluents which can be used in this process are all the customary solvents.

Solvents which can preferably be used are aromatic hydrocarbons, such as benzene or toluene, alcohols, such as methanol, ethanol, isopropanol or ethylene glycol, nitrites, such as acetonitrile, ethers, such as tetrahydrofuran or dioxane, amides, such as dimethylformamide, or other polar solvents, such as dimethyl sulphoxide or sulpholane.

It is often expedient first to prepare the corresponding salt from the compound of the formula (Ia) by addition of a deprotonating agent (such as, for example, potassium tert-butylate or sodium hydride). The compound of the formula (Ia) is reacted with carbon disulphide until the formation of the intermediate compound has ended, for example after the mixture has been stirred at room temperature for several hours.

The further reaction with the alkyl halide of the formula (VII) is preferably carried out at 0° to 70° C., and in particular at 20° to 50° C. At least the equimolar amount of alkyl halide is employed for this reaction.

The reaction is carried out under normal pressure or under increased pressure, preferably under normal pressure.

Working up is again carried out by customary methods.

In preparation process (E), about 1 mol of sulphonic acid chloride of the formula (VIII) is reacted per mole of starting compound of the formula (Ia) at 0° to 150° C. preferably at 20° to 70° C.

Possible diluents which are optionally added are all the inert organic solvents, such as halogenated hydrocarbons, ethers, amides, carboxylic acid esters, nitriles, sulphones or sulphoxides.

Acetonitrile, dimethyl sulphoxide, ethyl acetate, methyl tert-butyl ether, tetrahydrofuran, dimethylformamide or methylene chloride are preferably employed.

If, in a preferred embodiment, the enolate salt of the compound of the formula (Ia) is prepared by addition of strong deprotonating agents (such as, for example, sodium hydride or potassium tert-butylate), further addition of acid-biding agents can be omitted.

If acid-binding agents are employed, the customary inorganic or organic bases are possible, examples which may be mentioned being sodium hydroxide, sodium carbonate, potassium carbonate and pyridine.

The reaction can be carried out under normal pressure or under increased pressure, and is preferably carried out under normal pressure. Working up is carried out by customary methods.

If appropriate, preparation process (E) can be carried out under phase transfer conditions (W. J. Spillane et. al.; J. Chem. Soc., Perkin Trans I, (3) 677–9 (1982)). In this case, 0.3 to 5 mol of sulphonic acid chloride of the formula (VIII), preferably 1 mol, are reacted per mole of starting compound of the formula (Ia) at 0° to 150° C., preferably at 20° to 70° C.

Phase transfer catalysts which can be used are all the quaternary ammonium salts, preferably tetraoctylammonium bromide and benzyltriethylammonium chloride. Organic solvents which can be used in this case are all the non-polar inert solvents, and benzene or toluene are preferably employed.

In preparation process (F), 1 mol of the compound of the formula (Ia) and 1 to 2, preferably 1 to 1.3, mol of the phosphorus compound of the formula (IX) are reacted per mole of the compound of the formula (Ia) at temperatures between −40° C. and 150° C., preferably between −10° and 110° C., to give compounds of the formula (Ie).

Possible diluents which are optionally added are all the inert organic solvents, such as halogenated hydrocarbons, ethers, amides, nitriles, carboxylic acid esters, sulphones, sulphoxides and the like.

Acetonitrile, dimethyl sulphoxide, ethyl acetate, methyl tert-butyl ether, tetrahydrofuran, dimethylformamide or methylene chloride are preferably employed.

Possible acid-binding agents which are optionally added are the customary inorganic or organic bases, such as hydroxides, amines and carbonates. Examples which may be mentioned are sodium hydroxide, sodium carbonate, potassium carbonate, pyridine, triethylamine or DABCO.

The reaction can be carried out under normal pressure or under increased pressure, and is preferably carried out under normal pressure. Working up is carried out by customary methods of organic chemistry. Purification of the end products obtained is preferably carried out by crystallization, chromatographic purification or by so-called "incipient distillation", i.e. removal of the volatile constituents in vacuo.

Process (G) is characterized in that compounds of the formula (Ia) are reacted with metal compounds of the formula (X) or amines of the formula (XI).

Diluents which can be employed in the process according to the invention are preferably ethers, such as tetrahydrofuran, dioxane or diethyl ether, or also alcohols, such as methanol, ethanol or isopropanol, as well as water. Process (G) according to the invention is in general carried out under normal pressure. The reaction temperatures are in general between −20° C. and 100° C., preferably between 0° C. and 50° C.

In carrying out process (H) according to the invention, the starting substances of the formulae (Ia) and (XII) or (XIII) are in general used in approximately equimolar amounts. However, it is also possible to employ one or other of the components in a relatively large excess (up to 2 mol). In general, a procedure is followed in which the reaction mixture is concentrated by stripping off the diluent.

In preparation process (Hα), about 1 mol of isocyanate or isothiocyanate of the formula (XII) is reacted per mole of starting compound of the formula (Ia) at 0° to 100° C., preferably at 20° to 50° C.

Possible diluents which are optionally added are all the inert organic solvents, such as hydrocarbons, halogenated hydrocarbons, ethers, carboxylic acid esters, amines, nitriles, sulphones and sulphoxides.

Toluene, methylene chloride, tetrahydrofuran, ethyl acetate, dimethylformamide or dimethyl sulphoxide are preferably employed.

If appropriate, catalysts can be added to accelerate the reaction. Catalysts which can very advantageously be employed are organotin compounds, such as, for example, dibutyltin dilaurate. The reaction is preferably carried out under normal pressure.

In preparation process (Hβ), about 1 mol of carbamic acid chloride or thiocarbamic acid chloride of the formula (XIII) is reacted per mole of starting compound of the formula (Ia) at 0° to 150° C., preferably at 20° to 70° C.

Possible diluents which are optionally added are all the inert polar organic solvents, such as halogenated hydrocarbons, carboxylic acid esters, ethers, amides, nitriles, sulphones or sulphoxides.

Acetonitrile, ethyl acetate, dimethyl sulphoxide, methyl tert-butyl ether, tetrahydrofuran, dimethylformamide or methylene chloride are preferably employed.

If, in a preferred embodiment, the enolate salt of the compound of the formula (Ia) is prepared by addition of strong deprotonating agents (such as, for example, sodium hydride or potassium tert-butylate), further addition of acid-binding agents can be omitted.

If acid-binding agents are employed, the customary inorganic organic bases are possible, examples which may be mentioned being sodium hydroxide, sodium carbonate, potassium carbonate, pyridine, triethylamine or DABCO.

The reaction can be carried out under normal pressure or under increased pressure, and is preferably carried out under normal pressure. Working up is carried out by customary methods.

The following compounds of the formula (II) may be mentioned as examples:

methyl 3,3-dimethyl-2-(2,4,6-trimethylphenyl)-acetyl-cyclopropanecarboxylate, methyl 2-(2,4,6-trimethylphenyl)-acetyl-cyclobutanecarboxylate, methyl 1,2-dimethyl-2-(2,4,6-trimethylphenyl)-acetyl-cyclobutanecarboxylate,
methyl 3,4-dimethyl-2-(2,4,6-trimethylphenyl)-acetyl-cyclobutanecarboxylate,
methyl 2-(2,4,6-trimethylphenyl)-acetyl-cyclopentanecarboxylate,
methyl 3-methyl-2-(2,4,6-trimethylphenyl)-acetyl-cyclopentanecarboxylate,
methyl 3-methoxy-2-(2,4,6-trimethylphenyl)-acetyl-cyclopentanecarboxylate,
methyl 4-methyl-2-(2,4,6-trimethylphenyl)-acetyl-cyclopentanecarboxylate,
methyl 4-methoxy-2-(2,4,6-trimethylphenyl)-acetyl-cyclopentanecarboxylate,
methyl 3,4-dimethyl-2-(2,4,6-trimethylphenyl)-acetyl-cyclopentanecarboxylate,
3,4-dimethoxy-2-(2,4,6-trimethylphenyl)-acetyl-cyclopentanecarboxylate,
methyl 3,4-dihydroxy-2-(2,4,6-trimethylphenyl)-acetyl-cyclopentanecarboxylate,
methyl 3-oxo-2-(2,4,6-trimethylphenyl)-acetyl-cyclopentanecarboxylate,
methyl 4-oxo-2-(2,4,6-trimethylphenyl)-acetyl-cyclopentanecarboxylate,
methyl 3,4-methylenedioxy-2-(2,4,6-trimethylphenyl)-acetyl-cyclopentanecarboxylate,
methyl 4,5-methylenedioxy-2-(2,4,6-trimethylphenyl)-acetyl-cyclohexanecarboxylate,
methyl 2-(2,4,6-trimethylphenyl)-acetyl-cyclohexanecarboxylate,
methyl 3-methyl-2-(2,4,6-trimethylphenyl)-acetyl-cyclohexanecarboxylate,
methyl 3-methoxy-2-(2,4-6-trimethylphenyl)-acetyl-cyclohexanecarboxylate,
methyl 4-methyl-2-(2,4,6-trimethylphenyl)-acetyl-cyclohexanecarboxylate,
methyl 4-methoxy-2-(2,4,6-trimethylphenyl)-acetyl-cyclohexanecarboxylate,
methyl 5-methyl-2-(2,4,6-trimethylphenyl)-acetyl-cyclohexanecarboxylate,
methyl 5-methoxy-2-(2,4,6-trimethylphenyl)-acetyl-cyclohexanecarboxylate,
methyl 6-methyl-2-(2,4,6-trimethylphenyl)-acetyl-cyclohexanecarboxylate,
methyl 6-methoxy-2-(2,4,6-trimethylphenyl)-acetyl-cyclohexanecarboxylate,
methyl 1-methyl-2-(2,4,6-trimethylphenyl)-acetyl-cyclohexanecarboxylate,
methyl 2-methyl-2-(2,4,6-trimethylphenyl)-acetyl-cyclohexanecarboxylate,
methyl 3,4-dimethyl-2-(2,4,6-trimethylphenyl)-acetyl-cyclohexanecarboxylate,
methyl 5,6-dimethyl-2-(2,4,6-trimethylphenyl)-acetyl-cyclohexanecarboxylate,
methyl 4,5-dimethyl-2-(2,4,6-trimethylphenyl)-acetyl-cyclohexanecarboxylate,
methyl 4,5-dihydroxy-2-(2,4,6-trimethylphenyl)-acetyl-cyclohexanecarboxylate,
methyl 4,5-methylenedioxy-2-(2,4,6-trimethylphenyl)-acetyl-cyclohexanecarboxylate,
methyl 4,5-dihydroxy-O-methylidene-2-(2,4,6-trimethylphenyl)-acetyl-cyclohexanecarboxylate,
methyl 1,2-methylene-2-(2,4,6-trimethylphenyl)-acetyl-cyclohexanecarboxylate,
methyl 4-oxo-2-(2,4,6-trimethylphenyl)-acetyl-cyclohexanecarboxylate,
methyl 1,2-tetramethylene-2-(2,4,6-trimethylphenyl)-acetyl-cyclohexanecarboxylate,
methyl 3,6-methylene-2-(2,4,6-trimethylphenyl)-acetyl-cyclohexanecarboxylate,
methyl 3,6-ethylene-2-(2,4,6-trimethylphenyl)-acetyl-cyclohexanecarboxylate,
ethyl 3,3-dimethyl-2-(2,4,6-trimethylphenyl)-acetyl-cyclopropanecarboxylate,
ethyl 2-(2,4,6-trimethylphenyl)-acetyl-cyclobutanecarboxylate,
ethyl 1,2-dimethyl-2-(2,4,6-trimethylphenyl)-acetyl-cyclobutanecarboxylate,
Methyl 3,4-dimethyl-2-(2,4,6-trimethylphenyl)-acetyl-cyclobutanecarboxylate,
ethyl 2-(2,4,6-trimethylphenyl)-acetyl-cyclopentanecarboxylate,
methyl 3-methyl-2-(2,4,6-trimethylphenyl)-acetyl-cyclopentanecarboxylate,
ethyl 3-methoxy-2-(2,4,6-trimethylphenyl)-acetyl-cyclopentanecarboxylate,
ethyl 4-methyl-2-(2,4,6-trimethylphenyl)-acetyl-cyclopentanecarboxylate,
ethyl 4-methoxy-2-(2,4,6-trimethylphenyl)-acetyl-cyclopentanecarboxylate,
ethyl 3,4-dimethyl-2-(2,4,6-trimethylphenyl)-acetyl-cyclopentanecarboxylate,
ethyl 3,4-dimethoxy-2-(2,4,6-trimethylphenyl)-acetyl-cyclopentanecarboxylate,
ethyl 3,4-dihydroxy-2-(2,4,6-trimethylphenyl)-acetyl-cyclopentanecarboxylate,
ethyl 3-oxo-2-(2,4,6-trimethylphenyl)-acetyl-cyclopentanecarboxylate,
ethyl 4-oxo-2-(2,4,6-trimethylphenyl)-acetyl-cyclopentanecarboxylate,
ethyl 3,4-methylethylidenedioxy-(2,4,6-trimethylphenyl)-acetyl-cyclopentanecarboxylate,
ethyl 4,5-methylethylidenedioxy-2-(2,4,6-(trimethylphenyl)-acetyl-cyclohexanecarboxylate,
ethyl 3-methyl-2-(2,4,6-trimethylphenyl)-acetyl-cyclohexanecarboxylate,
ethyl 3-methoxy-2-(2,4,6-trimethylphenyl)-acetyl-cyclohexanecarboxylate,
ethyl 4-methyl-2-(2,4,6-trimethylphenyl)-acetyl-cyclohexanecarboxylate,
ethyl 4-methoxy-2-(2,4,6-trimethylphenyl)-acetyl-cyclohexanecarboxylate,
ethyl 5-methyl-2-(2,4,6-trimethylphenyl)-acetyl-cyclohexanecarboxylate,
ethyl 5-methoxy-2-(2,4,6-trimethylphenyl)-acetyl-cyclohexanecarboxylate,
ethyl 6-methyl-2-(2,4,6-trimethylphenyl)-acetyl-cyclohexanecarboxylate,
ethyl 6-methoxy-2-(2,4,6-trimethylphenyl)-acetyl-cyclohexanecarboxylate,
ethyl 1-methyl-2-(2,4,6-trimethylphenyl)-acetyl-cyclohexanecarboxylate,
ethyl 2-methyl-2-(2,4,6-trimethylphenyl)-acetyl-cyclohexanecarboxylate,
ethyl 3,4-dimethyl-2-(2,4,6-trimethylphenyl)-acetyl-cyclohexanecarboxylate,
ethyl 5,6-dimethyl-2-(2,4,6-trimethylphenyl)-acetyl-cyclohexanecarboxylate,
ethyl 4,5-dimethyl-2-(2,4,6-trimethylphenyl)-acetyl-cyclohexanecarboxylate,
ethyl 4,5-dihydroxy-2-(2,4,6-trimethylphenyl)-acetyl-cyclohexanecarboxylate,
ethyl 4,5-methylidenedioxy-2-(2,4,6-trimethylphenyl)-acetyl-cyclohexanecarboxylate,
ethyl 4,5-methylidenedioxy-2-(2,4,6-trimethylphenyl)-acetyl-cyclohexanecarboxylate, ethyl 1,2-methylene-2-(2,4,6-trimethylphenyl)-acetyl-cyclohexanecarboxylate,
ethyl 4-oxo-2-(2,4,6-trimethylphenyl)-acetyl-cyclohexanecarboxylate,
ethyl 1,2-tetramethylene-2-(2,46-trimethylphenyl)-acetyl-cyclohexanecarboxylate,
ethyl 3,6-methylene-2-(2,4,6-trimethylphenyl)-acetyl-cyclohexanecarboxylate, The following compounds of the formula (XIV) may be mentioned as examples:
3,3-dimethyl-2-(2,4,6-trimethylphenyl)-acetyl-cyclopropanecarboxylic acid,
2-(2,4,6-trimethylphenyl)-acetyl-cyclobutanecarboxylic acid,
1,2-dimethyl-2-(2,4,6-trimethylphenyl)-acetyl-cyclobutanecarboxylic acid,
2-(2,4,6-trimethylphenyl)-acetyl-cyclobutanecarboxylic acid,
3,4-dimethyl-2-(2,4,6-trimethylphenyl)-acetyl-cyclopentanecarboxylic acid,
3-methyl-2-(2,4,6-trimethylphenyl)-acetyl-cyclopentanecarboxylic acid,
3-methoxy-2-(2,4,6-trimethylphenyl)-acetyl-cyclopentanecarboxylic acid,
4-methyl-2-(2,4,6-trimethylphenyl)-acetyl-cyclopentanecarboxylic acid,
4-methoxy-2-(2,4,6-trimethylphenyl)-acetyl-cyclopentanecarboxylic acid,
3,4-dimethyl-2-(2,4,6-trimethylphenyl)-acetyl-cyclopentanecarboxylic acid,
3,4-dimethoxy-2-(2,4,6-trimethylphenyl)-acetyl-cyclopentanecarboxylic acid,
3,4-dihydroxy-2-(2,4,6-trimethylphenyl)-acetyl-cyclopentanecarboxylic acid,
3-oxo-2-(2,4,6-trimethylphenyl)-acetyl-cyclopentanecarboxylic acid,
4-oxo-2-(2,4,6-trimethylphenyl)-acetyl-cyclopentanecarboxylic acid,
3,4-methyl ethylidenedioxy-2-(2,4,6-trimethylphenyl)-acetyl-cyclopentanecarboxylic acid,
2-(2,4,6-trimethylphenyl)-acetyl-cyclohexanecarboxylic acid,
3-methyl-2-(2,4,6-trimethylphenyl)-acetyl-cyclohexanecarboxylic acid,
3-methoxy-2-(2,4,6-trimethylphenyl)-acetyl-cyclohexanecarboxylic acid,
4-methyl-2-(2,4,6-trimethylphenyl)-acetyl-cyclohexanecarboxylic acid,
4-methoxy-2-(2,4,6-trimethylphenyl)-acetyl-cyclohexanecarboxylic acid,
5-methyl-2-(2,4,6-trimethylphenyl)-acetyl-cyclohexanecarboxylic acid,
5-methoxy-2-(2,4,6-trimethylphenyl)-acetyl-cyclohexanecarboxylic acid,
6-methyl-2-(2,4,6-trimethylphenyl)-acetyl-cyclohexanecarboxylic acid,
6-methoxy-2-(2,4,6-trimethylphenyl)-acetyl-cyclohexanecarboxylic acid,
1-methyl-2-(2,4,6-trimethylphenyl)-acetyl-cyclohexanecarboxylic acid,
2-methyl-2-(2,4,6-trimethylphenyl)-acetyl-cyclohexanecarboxylic acid,
3,4-dimethyl-2-(2,4,6-trimethylphenyl)-acetyl-cyclohexanecarboxylic acid,
5,6-dimethyl-2-(2,4,6-trimethylphenyl)-acetyl-cyclohexanecarboxylic acid,
4,5-dimethyl-2-(2,4,6-trimethylphenyl)-acetyl-cyclohexanecarboxylic acid,
4,5-dihydroxy-2-(2,4,6-trimethylphenyl)-acetyl-cyclohexanecarboxylic acid,
4,5-methylethylidenedioxy-2-(2,4,6-trimethylphenyl)-acetyl-cyclohexanecarboxylic acid,
4,5-methylenedioxy-2-(2,4,6-trimethylphenyl)-acetyl-cyclohexanecarboxylic acid,
1,2-methylene-2-(2,4,6-trimethylphenyl)-acetyl-cyclohexanecarboxylic acid,
4-oxo-2-(2,4,6-trimethylphenyl)-acetyl-cyclohexanecarboxylic acid,
1,2-tetramethylene-2-(2,4,6-trimethylphenyl)-acetyl-cyclohexanecarboxylic acid,
3,6-methylene-2-(2,4,6-trimethylphenyl)-acetyl-cyclohexanecarboxylic acid,
3,6-ethylene-2-(2,4,6-trimethylphenyl)-acetyl-cyclohexanecarboxylic acid, The active compounds are suitable for controlling animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria* migratorioides, *Melanoplus differentialis Schistocerca gregaria* and Supella spp.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., Phthirus spp., Pediculus spp., Haematopinus spp., Linognathus spp. and Solenopotes spp.

From the order of the Mallophaga, for example, Trichodectes spp., Damalinea spp., Trimenopon spp., Monopon spp., Trinoton spp., Bovicola spp., Werneckiella spp., Lepikentron spp. and Felicola spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus*, Triatoma spp. and Panstrogylus spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varive stis*, Atomaria spp., *Oryzaephilus surinamensis*, Antho nomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., Meligethes aeneus, Ptinus spp., *Niptus hololeucus, Gibbium psylloides*, Tribolium spp., Tenebrio molitor, Agriotes spp., Cono derus spp., *Melolontha melolontha, Amphimallon solsti* tialis and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., Calliphora spp., Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae, Tipula paludosa*, Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Hydrotaea spp., Stomoxys spp., Haematobia spp., Morellia spp., Fannia spp., Glossina spp., Calliphora spp., Wohlfahrtia spp., Sarcophaga spp., Oestrus spp., Hypoderma spp., Gasterophilus spp., Hippobosca spp., Lipoptena spp., Melophagus spp. and Muscina spp.

From the order of the Siphonapterida, for example, Xenopsylla spp., Ceratophyllus spp., Pulex spp. and Ctenocephalides spp.

From the order of the Arachnida, for example, *Scorpio maurus* and *Latrodectus mactans*.

From the order of the Acarina, for example, Myocoptes spp., Otodectes spp., *Acarus siro*, Argas spp., Ornithodoros spp., Ornithonyssus spp., Dermanyssus spp., *Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Dermacentor spp., Haemaphysalis spp., Raillietia spp., Pneumonyssus spp., Sternostorma spp. and Varroa spp.

From the order of the Actinedida (Prostigmata) and Acaridida (Astigmata), for example: Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds according to the invention are distinguished by a potent insecticidal and acaricidal activity.

They can be employed particularly successfully against insects which are harmful to plants, such as, for example, against the larvae of the mustard beetle (*Phaedon cochleariae*) or against the larvae of the green Reiszikada (*Nephotettix cincticeps*) or against the caterpillars of the cabbage moth (*Plutella maculipennis*).

The active compounds according to the invention can furthermore be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The active compounds according to the invention are particularly suitable for selectively controlling weeds in dicotyledon crops by the pre-and post-emergence method. For example, they can be employed particularly successfully for controlling harmful grasses in cotton or sugar beet.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

Particularly favourable mixing partners are, for example, the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazol-5-carboxanilide; 2,6-di-chloro-N-(4-trifluoromethylbenzyl)-benzamide; (E)-2-methoxyimino-N-methyl-2-(2-phenoxyphenyl)-acetamide; 8-hydroxyquinoline sulfate; methyl-(E)-2-{2-[6-(2-cyanophenoxy)-pyrimidine-4-yloxy]-phenyl}-3-methoxyacrylate; methyl-(E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calciumpolysulphide, captafol, captan, carbendazim, carboxin, chinomethionate, (quinomethionate), chloroneb, chloropicrin, chlorothalonil, chlozolinate, cufraneb, cymoxanil, cyproconazole, cyprofuram, dichlorophen, dichlobutrazole, dichlofluanid, diclomezin, dichloran, diethofencarb, difenoconazole, dimethirimol, dimethirimol, dimethomorph, diniconazole, dinocap, diphenylamine, dipyrithion, ditalimfos, dithianon, dodine, drazoxolon, edifenphos, epoxyconazole, ethirimol, etridiazole, Fenarimol, fenbuconazole, fenfuram, fenitropan, fenpiclonil, fenpropidin, fenpropimorp, fentin acetate, fentin hydroxide, ferbam, ferimzone, fluazinam, fludioxonil, fluoromide, fluquinconazole, flusilazole, flusulphamide, flutolanil, flutriafol, folpet, fosetyl aluminium, fthalide, fuberidazole, furalaxyl, furmecyclox, guazatine, hexachlorobenzene, hexaconazole, hymexazole, imazalil, imibenconazole, iminoctadin, iprobenfos (IBP), iprodione, isoprothiolane, kasugamycin, copper formulations, such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphene, phthalide, pimaricin, piperalin, polycarbamate, polyoxin, probenazole, prochloraz, procymidon, propamocarb, propiconazole, propineb, pyrazophos, pyrifenox, pyrimethanil, pyroquilon, quintozene (PCNB), sulfur and sulfur formulations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxid, trichlamid, tricyclazol, tridemorph, triflumizol, triforin, triticonazole, validamycin A, vinclozolin, zineb, ziram.

Bactericides:

bronopol, dichlorophen, nitrapyrin, nickel dimethyldithiocarbamate, kasugamycin, octhilinon, furancarboxylic acid, oxytetracycline, probenazole, streptomycin, tecloftalam, copper sulphate and other copper formulations.

Insecticides/acaricides/nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezin, cyanophos, cycloprothrin, cyfluthrin, cyhalothrin, cyhexatin, cypermethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfen valerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos, RH 5992, salithion, sebufos, silafluofen, sulphotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxy-alkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound content of the use forms prepared from the commercially available formulations can vary within wide limits. The active compound concentration of the use forms can be from 0.0000001 to 95% by weight of active compound, preferably between 0.0001 and 1% by weight.

Use takes place in a manner suited to the use forms.

When used against hygiene pests and pests of stored products, the active compound is distinguished by an outstanding residual action on wood and clay and by a good stability to alkali on limed substrates.

The active compounds according to the invention act not only against plant pests, hygiene pests and pests of stored products, but also in the veterinary medicine sector against animal parasites (ectoparasites), such as hard ticks, soft ticks, mange mites, harvest mites, flies (biting and licking), parasitic fly larvae, lice, hair lice, feather lice and fleas. For example, they display an outstanding activity against ticks, such as, for example, Boophilus microplus.

The active compounds of the formula (I) according to the invention are also suitable for combating arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice.

By combating these anthropods cases of death and reductions in productivity (for meat, milk, wool, hides, eggs, honey etc) should be diminished, so that more economical and simple animal husbandry is possible by use of the active compounds according to the invention.

The active compounds according to the invention are used in the veterinary sector in a known manner by enteral administration in the form of, for example, tablets, capsules, potions, drenches, granules, pastes boli, the feed-through process and suppositories, by parental administration, such as, for example, by injection (intramuscular, subcutaneous, intravenous, intraperitoneal etc), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices, etc.

When used for livestock, poultry, pets and the like, the active compounds of the formula (I) can be used as formulations (for example powders, emulsions, free-flowing compositions), which comprise the active compounds in an amount of 1 to 80% by weight, directly or after a 100 to 10,000 fold dilution, or they can be used as a chemical bath.

The preparation and the use of the substances according to the invention is illustrated by the following examples.

PREPARATION EXAMPLES

Example Ia-1 and Ia-2

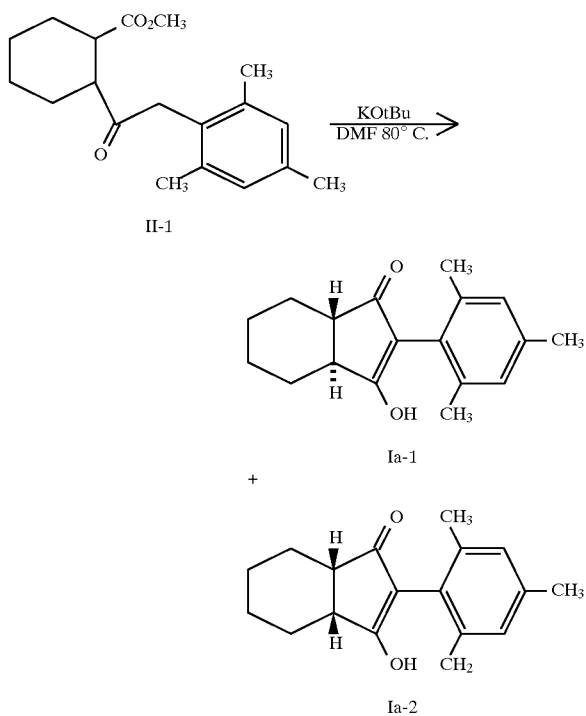

2.8g of potassium tert-butylate are added to a solution of the compound according to Example II-1 (4.96 g; 16.4 mmol) in dimethylformamide (30 ml) and the mixture is stirred at 80° C. for 1 hour. 5 ml of acetic acid are added, the mixture is concentrated and the residue is chromatographed over silica gel (1:1 ethyl acetate:hexane). First 1.96 g (44%) of the compound Ia-1 shown above (colourless solid, melting point: 192° C.) and then 1.27 g (29%) of the compound Ia-2 shown above (colourless solid, melting point 184° C.) are isolated.

Example Ia-5

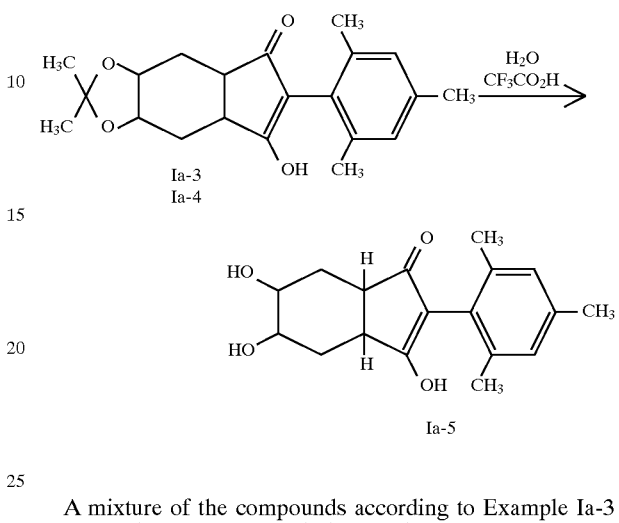

A mixture of the compounds according to Example Ia-3 and Ia-4 (cis-trans mixture) (300 mg), trifluoroacetic acid (10 ml) and water (10 ml) is stirred at room temperature for 24 hours and concentrated. The solid residue is washed with hot cyclohexane.

Yield: 110 mg, diastereomer mixture.

$^1$H-NMR (CDCl$_3$, δ ppm): 2.25 (s, 3H); 4.69 and 4.80 (2s, 1H); 6.88 (s, 2H).

The compounds of the formula (Ia) listed in table 7 were synthesized analogously to examples Ia-1, Ia-2 and Ia-5 and in accordance with the general instructions on the preparation.

TABLE 7

(Ia)

| Ex. No. | A | Q | B | B' | Isomer | M.p. °C. |
|---|---|---|---|---|---|---|
| Ia-3 | —CH$_2$—CH——————CH—CH$_2$—<br>        \|                  \|<br>        O—C(CH$_3$)$_2$—O | | H | H | trans | 160° C. |
| Ia-4 | —CH$_2$—CH——————CH—CH$_2$—<br>        \|                  \|<br>        O—C(CH$_3$)$_2$—O | | H | H | cis | 130° C. |
| Ia-6 | —CH$_2$—CH————CH—CH$_2$—<br>        \|        \|<br>        CH$_3$   CH$_3$ | | H | H | trans | oil |

TABLE 7-continued (Ia) structure shown with A, Q, B, B' substituents on cyclopentanone ring with 2,4,6-trimethylphenyl group and HO.

| Ex. No. | A | Q | B | B' | Isomer | M.p. °C. |
|---|---|---|---|---|---|---|
| Ia-7 | —CH$_2$—CH(CH$_3$)—CH(CH$_3$)—CH$_2$— | | H | H | cis | oil |
| Ia-8 | —CH$_2$—CH(CH$_3$)—(CH$_2$)$_2$— | | H | H | trans | oil |
| Ia-9 | —CH$_2$—CH(CH$_3$)—(CH$_2$)$_2$— | | H | H | cis | oil |
| Ia-10 | —CH—(CH$_2$)$_2$—CH— bridged by —CH$_2$— | | H | H | cis/trans | 235° C. |
| Ia-11 | —(CH$_2$)$_4$— | | CH$_3$ | H | cis/trans | 115° C. |

Example Ib-1

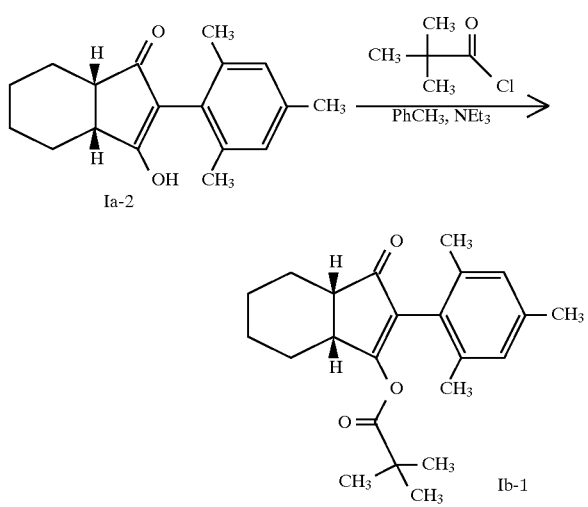

Pivaloyl chloride (0.75 ml) is added to a solution of the compound according to Example Ia-2 (1000 mg) in toluene (10 ml) and triethylamine (1 ml). After reflux for 1 hour, the reaction mixture is filtered directly over silica gel (mobile phase 1:4 ethyl ether: petroleum ether). 1.02 g of an oil are obtained. Yield: 79%.

$^1$H-NMR (200 MHz, CDCl$_3$, δ ppm): 1.10 (s, 9H); 1.4–2.3 (m, 8H); 2.05 (s, 3H); 2.10 (s, 3H); 2.23 (s, 3H); 2.84 (q, 1H, J=6.5 Hz); 3.38 (q, 1H, J=6.5 Hz); 6.82 (bs, 2H).

The compounds of the formula (Ib) listed in Table 8 were prepared analogously to Example Ib-1 and in accordance with the general instructions on the preparation:

TABLE 8

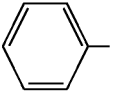

(Ib)

| Ex No | A Q | B | B' | R¹ | Isomer | ¹H-NMR 200 MHz, CDCl₃, δ ppm |
|---|---|---|---|---|---|---|
| Ib-2 | —(CH₂)₄— | H | H | —CH₃ | cis | 2.28 (s, 3H); 2.84 (q, 1H, J = 6.5 Hz); 3.43 (q, 1H, J = 6,5 Hz). |
| Ib-3 | —(CH₂)₄— | H | H | —CH₃ | trans | 2.39 (m, 1H); 2.98 (m, 1H); 6.85 (bs, 2H). |
| Ib-4 | —(CH₂)₄— | H | H | -t-C₄H₉ | trans | 1.11 (s, 9H); 6.81 (bs, 2H). |
| Ib-5 | —CH₂—CH———CH—CH₂—<br>\|  \|<br>O—C(CH₃)₂—O | H | H | -t-C₄H₉ | trans | m.p.: 148° C. |
| Ib-6 | —CH₂—CH———CH—CH₂—<br>\|  \|<br>O—C(CH₃)₂—O | H | H | —CH₃ | trans | m.p.: 150° C. |
| Ib-7 | —CH₂—CH———CH—CH₂—<br>\|  \|<br>O—C(CH₃)₂—O | H | H | Cl—CH₂— | trans | m.p.: 130° C. |
| Ib-8 | —CH₂—CH———CH—CH₂—<br>\|  \|<br>O—C(CH₃)₂—O | H | H | n-C₄H₉—CH—<br>\|<br>C₂H₅ | trans | m.p.: 98° C. |
| Ib-9 | —(CH₂)₄— | H | H | n-C₄H₉—CH—<br>\|<br>C₂H₅ | cis | 2.22 (s, 3H); 6.81 (s, 2H). |
| Ib-10 | —(CH₂)₄— | H | H | —C₆H₅ (phenyl) | cis | m.p.: 111° C. |
| Ib-11 | —CH₂—CH—(CH₂)₂—<br>\|<br>CH₃ | H | H | -t-C₄H₉ | cis/trans | 1.08 (s, 9H); 6.81 (s, 2H). |
| Ib-12 | —CH₂—CH—(CH₂)₂—<br>\|<br>CH₃ | H | H | —CH₃ | cis/trans | 2.26 (s, 3H); 6.86 (s, 2H). |
| Ib-13 | —CH₂—CH—(CH₂)₂—<br>\|<br>CH₃ | H | H | n-C₄H₉—CH—<br>\|<br>C₂H₅ | cis/trans | 2.23 (s, 3H); 6.82 (s, 2H). |
| Ib-14 | —CH₂—CH———CH—CH₂—<br>\|  \|<br>CH₃  CH₃ | H | H | -t-C₄H₉ | cis/trans | 2.25 (s, 3H); 6.82 (s, 2H). |
| Ib-15 | —CH₂—CH———CH—CH₂—<br>\|  \|<br>CH₃  CH₃ | H | H | —CH₃ | cis/trans | 2.28 (s, 3H); 6.86 (s, 2H). |
| Ib-16 | —CH₂—CH———CH—CH₂—<br>\|  \|<br>CH₃  CH₃ | H | H | n-C₄H₉—CH—<br>\|<br>C₂H₅ | cis/trans | 2.25 (s, 3H); 6.82 (s, 2H). |
| Ib-17 | —CH—(CH₂)₂—CH—<br>└—CH₂—┘ | H | H | t-C₄H₉ | cis/trans | m.p.: 106° C. |
| Ib-18 | —CH—(CH₂)₂—CH—<br>└—CH₂—┘ | H | H | CH₃ | cis/trans | m.p.: 142° C. |

Example Ic-1

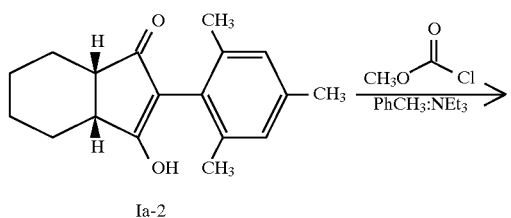

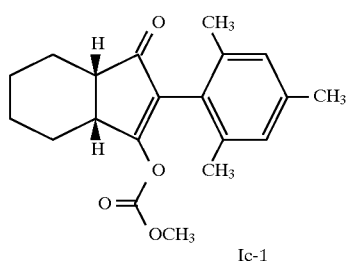

Ic-1

Methyl chloroformate (1.5 ml) is added to a solution of the compound according to Example Ia-2 (1000 mg) in toluene (10 ml) and triethylamine (1 ml). After reflux for 1 hour, the reaction mixture is filtered directly over silica gel (mobile phase 1:4 ethyl ether: petroleum ether). 1.19 g of an oil are obtained. Yield: 98%.

$^1$H-NMR (200 MHz, CDCl$_3$, δ ppm): 1.4–1.85 (m, 8H); 2.06 (s, 3H); 2.11 (s, 3H); 2.28 (s, 4H); 2.87 (q, 1H, J=6.5 Hz); 3.48 (q, 1H, J=6.5 Hz); 3.72 (s, 3H); 6.87 (bs, 2H).

The compound of the formula (Ic) listed in Table 9 was prepared analogously to Example Ic-1 and in accordance with the general instructions on the preparation:

TABLE 9

| Ex No | A | Q | B | B' | L | M | R² | Isomer | $^1$H-NMR 200 MHz, CDCl$_3$, δ ppm |
|---|---|---|---|---|---|---|---|---|---|
| Ic-2 | —(CH$_2$)$_4$— | | H | H | O | O | i-C$_3$H$_7$ | cis | 2.83 (q, 1H, J = 6.5 Hz); 3.45 (q, 1H, J = 6.5 Hz). |
| Ic-3 | —CH$_2$—CH——CH—CH$_2$— <br>          \|                \| <br>          O—C(CH$_3$)$_2$—O | | H | H | O | O | —CH$_3$ | trans | m.p. 162° C. |
| Ic-4 | —CH$_2$—CH——CH—CH$_2$— <br>          \|                \| <br>          O—C(CH$_3$)$_2$—O | | H | H | O | O | i-C$_3$H$_7$ | trans | m.p.: 120° C. |
| Ic-5 | —CH$_2$—CH—(CH$_2$)$_2$— <br>            \| <br>            CH$_3$ | | H | H | O | O | i-C$_3$H$_7$ | cis/trans | 2.26 (s, 3H); 6.86 (s, 2H). |
| Ic-6 | —CH$_2$—CH—CH—CH$_2$— <br>           \|    \| <br>          CH$_3$ CH$_3$ | | H | H | O | O | i-C$_3$H$_7$ | cis/trans | 2.26 (s. 3H); 6.85 (s, 2H). |
| Ic-7 | —CH$_2$—CH——CH—CH$_2$— <br>          \|                \| <br>          O—C(CH$_3$)$_2$—O | | H | H | O | O | s-C$_4$H$_9$ | trans | m.p.: 103° C. |
| Ic-8 | —CH$_2$—CH——CH—CH$_2$— <br>          \|                \| <br>          O—C(CH$_3$)$_2$—O | | H | H | O | O | i-C$_4$H$_9$ | trans | m.p.: 148° C. |
| Ic-9 | —CH—(CH$_2$)$_2$—CH— <br>                          \| <br>                  CH$_2$ | | H | H | O | O | i-C$_3$H$_7$ | cis/trans | m.p.: 104° C. |

Preparation of the starting compounds

Example II-1

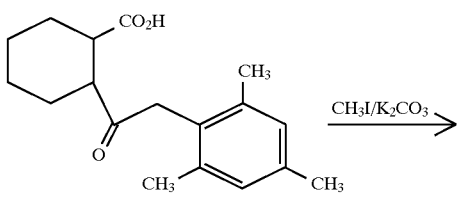

XIV-1

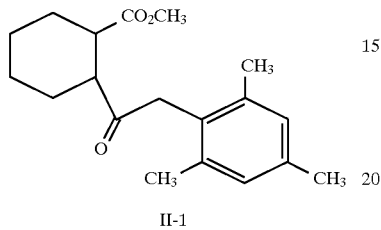

II-1

A mixture of the compound according to Example XIV-1 (2.13 g, 7.4 mmol), potassium carbonate (1 g), acetone (15 ml) and iodomethane (1.4 ml) is boiled under reflux for 5 hours, diluted with ethyl ether (100 ml) and filtered over silica gel and the filtrate is concentrated. 2.22 g (99%) of the compound II-1 shown above are obtained.

White solid: melting point: 97° C.

The compounds of the formula (II) listed in Table 10 were prepared analogously to Example II-1 and in accordance with the general instructions on the preparation:

Example II-9

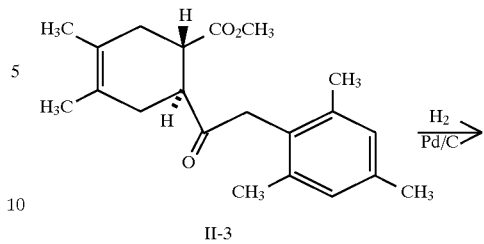

II-3

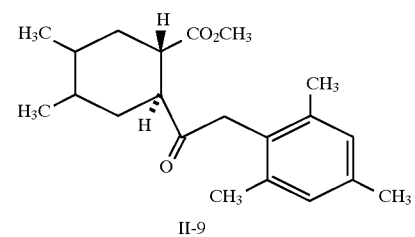

II-9

A suspension of the compound according to Example II-3 (15 g), and 5% of Pd/C (4.5 g) in methanol (300 ml) is stirred in a steel autoclave under a hydrogen pressure of 100 bar (100° C., 24 hours). The reaction mixture is cooled, and filtered and the filtrate is concentrated.

13 g of the compound II-9 shown above is obtained as a diastereomer mixture (oil).

$^1$H-NMR (CDCl$_3$, δ ppm): 3.60 (s, 3H); 3.80–3.90 (m, 2H); 6.85 (bs, 2H).

The compound of the formula (II) listed in table 11 was prepared analogously to Example II-9 and in accordance with the general instructions on the preparation:

TABLE 10

| Ex. | A | Q | B | B' | $R^{12}$ | $^1$H-NMR (CDCl$_3$, δ ppm or m.p. (°C.) |
|---|---|---|---|---|---|---|
| II-2 | (Z)—CH$_2$—CH=CH—CH$_2$— | | H | H | CH$_3$ | 110° C. |
| II-3 | (Z)—CH$_2$—C(CH$_3$)=C(CH$_3$)—CH$_2$— | | H | H | CH$_3$ | 193° C. |
| II-4 | —CH—CH=CH—CH—<br>└—CH$_2$—┘ | | H | H | CH$_3$ | 6.12 (m, 1H);<br>6.27 (m, 1H);<br>6.87 (s, 2H). |
| II-5 | —CH$_2$—CH—CH$_2$—CH$_2$—<br>\|<br>CH$_3$ | | H | H | CH$_3$ | 2.17 (s, 6H);<br>3.90 (m, 2H). |
| II-6 | (Z)—CH$_2$—CH=CH—CH$_2$— | | H | CH$_3$ | CH$_3$ | 5.60—5.75 (m, 2H);<br>6.85 (s, 2H). |

TABLE 11

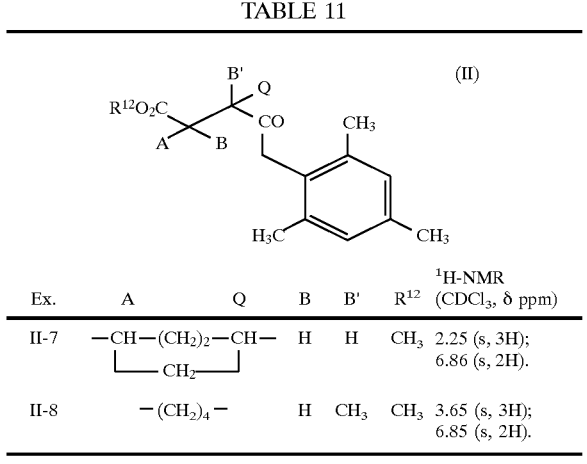

| Ex. | A | Q | B | B' | R[12] | $^1$H-NMR (CDCl$_3$, δ ppm) |
|---|---|---|---|---|---|---|
| II-7 | —CH—(CH$_2$)$_2$—CH—<br>└—CH$_2$—┘ | H | H | CH$_3$ | 2.25 (s, 3H);<br>6.86 (s, 2H). |
| II-8 | —(CH$_2$)$_4$— | H | CH$_3$ | CH$_3$ | 3.65 (s, 3H);<br>6.85 (s, 2H). |

Example II-10

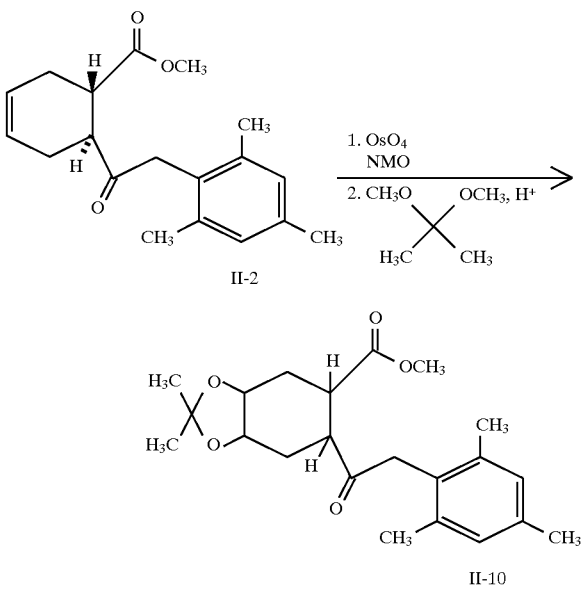

43.6g of the compound according to Example II-2 and 8.7 ml of 2.5% strength OsO$_4$ in t-butanol are added to a solution of N-methylmorpholine oxide (NMO) (21.4 g) in acetone (145 ml) and water (28 ml). The mixture is stirred at room temperature for 4 hours, 17.4 g of sodium thiosulphate are added and the mixture is stirred at room temperature for half an hour. The product is extracted with ether.

45.5 g (94.5% of theory) of a colourless solid (diastereomer mixture) are obtained.

This material is dissolved in 2,2-dimethoxypropane (100 ml), and 200 mg of 4-toluenesulphonic acid hydrate are added. After 20 hours at room temperature, the reaction mixture is washed with 10% strength aqueous potassium carbonate solution, dried and concentrated.

45 g of the compound II-10 shown above (oil, diastereomer mixture) are obtained.

$^1$H-NMR (CDCl$_3$, δ ppm); 2.26 (s, 3H); 3.62 (s, 3H); 6.82 (bs, 2H).

Example XIV-1

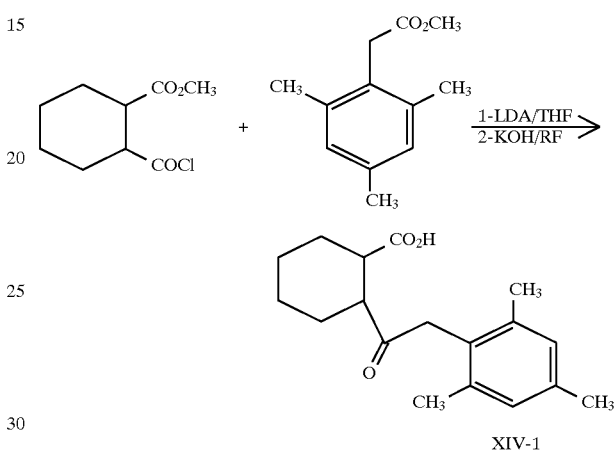

13.2g (68.7 mmol) of methyl 2,4,6-trimethylphenyl acetate are added to a solution of lithium diisopropylamide (75 mmol) in tetrahydrofuran (100 ml). After 30 minutes at room temperature, 14 g of 3,4-tetramethylenesuccinic acid methyl ester chloride are added and the mixture is stirred at room temperature (1 hour). 100 ml of water and 30 g of ammonium chloride are then added. The intermediate product is extracted with ether and filtered over silica gel. After concentration, the residue (oil, about 25 g) is boiled under reflux with 75 g of potassium hydroxide and 250 ml of water (2 days). The mixture is cooled and acidified (concentrated HCl) and the solid is filtered off. After recrystallization from ethyl acetate: cyclohexane 1:1, 7.5 g (38%) of the compound XIV-1 shown above are obtained.

White solid, m.p.: 195° C.

The compound of the formula (XIV) listed in Table 12 was prepared analogously to Example XIV-1 and in accordance with the general instructions on the preparation:

TABLE 12

(XIV)

[Structure: 2,4,6-trimethylphenyl group -CH2-C(=O)-C(B')(Q)-C(A)(B)-CO2H]

| Ex. No. | A | Q | B | B' | $^1$H-NMR (CDCl$_3$, δ ppm) or m.p. (°C.) |
|---|---|---|---|---|---|
| XIV-2 | (Z)—CH$_2$—CH=CH—CH$_2$— | | H | H | 193° C. |
| XIV-3 | (Z)—CH$_2$—C≡C—CH$_2$— (with CH$_3$, CH$_3$ on the triple bond carbons) | | H | H | 1.11 (bs, 6H); 3.90 (s, 2H). |
| XIV-4 | (Z)—CH—CH=CH—CH— (bridged by CH$_2$) | | H | H | 6.17 (m, 1H); 6.27 (m, 1H); 6.87 (s, 2H). |
| XIV-5 | (Z)—CH$_2$—CH(CH$_3$)—CH$_2$—CH$_2$— | | H | H | 3.88 (m, 2H); 6.85 (s, 2H). |
| XIV-6 | (Z)—CH$_2$—CH=CH—CH$_2$— | | H | CH$_3$ | oil |

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, for example, compound Ia-1 showed a 100% action against Alopecurus myosuroides, Avena fatua and Setaria viridis when applied in an amount of, for example, 250 g/ha.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control. The figures denote:

0%=no action (like untreated control)

100%=total destruction

In this test, for example, compound Ib-1 showed 100% action against Avena fatua and Setaria viridis when applied in an amount of, for example, 250 g/ha.

Example C

Test with Boophilus microplus resistant/SP-resistant Parkhurst strain

Test animals: Adult satiated females

Solvent: Dimethyl sulphoxide 20 mg of active compound are dissolved in 1 ml of dimethyl sulphoxide, and lower concentrations are prepared by dilution with the same solvent.

The test is carried out as a 5-fold determination. 1 μl of the solutions is injected into the abdomen and the animals are transferred to dishes and kept in a controlled-environment chamber. The action is controlled 7 days after fertile eggs have been laid. Eggs of which the fertility is not externally visible are kept in glass tubes in a climatically controlled cabinet until the larvae hatch. An action of 100% means that no tick has laid fertile eggs.

In this test, for example, the compounds according to preparation examples Ia-1 and Ia-2 had an action of 100% at an active compound concentration of, for example, 1000 ppm.

Example D

Blowfly larvae test/development-inhibiting action

Test animals: Lucilia cuprina larvae

Solvent: 35 parts by weight of ethylene glycol monomethyl ether 35 parts by weight of nonylphenol polyglycol ether To produce a suitable formulation, 3 parts by weight of active compound are mixed with 7 parts of the abovementioned solvent/emulsifier mixture, and the emulsion concentrate thus obtained is diluted with water to the particular desired concentration.

About 20 Lucilia cuprina larvae are introduced into a test tube which contains approx. 1 cm$^3$ of horse meat and 0.5 ml of the active compound preparation to be tested. The activity of the active compound preparation is determined after 24 and 48 hours. The test tubes are transferred to a beaker with a sand-covered base. After a further 2 days, the test tubes are removed and the pupae are counted.

The action of the active compound preparation is evaluated according to the number of flies which have hatched after 1.5 times the development time and the untreated control. 100% here means that no flies have hatched; 0% means that all the flies have hatched normally.

In this test, for example, the compounds according to Preparation Examples Ia-1, Ib-2 and Ib-4 had an action of 100% at a concentration of, for example, 1000 ppm.

Example E

Tetranychus Test (OP-resistant/dipping treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all the development stages of the common spider mite (*Tetranychus urticae*) are treated by being dipped into the preparation of the active compound of the desired concentration.

After the specified period of time, the destruction in % is determined. 100% means that all the spider mites have been killed; 0% means that none of the spider mites have been killed.

In this test, for example, the compounds according to Preparation Examples Ia-1 and Ia-2 had an action of at least 98% after 13 days at an active compound concentration of, for example 0.1%.

Example F

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified period of time, the destruction in % is determined. 100% means that all the beetle larvae have been killed; 0% means that none of the beetle larvae have been killed.

In this test, for example, the compounds according to Preparation Examples Ia-1, Ia-2, Ib-1 and Ib-4 caused a destruction of 100% after 7 days at an active compound concentration of, for example, 0.1%.

Example G

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, for example, the compounds according to Preparation Examples Ia-1, Ia-2, Ib-1, Ib-2 and Ib-4 caused a destruction of 100% after 7 days at an active compound concentration of, for example, 0.1%.

Example H

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), as long as the leaves are still moist.

After the specified period of time, the destruction in % is determined. 100% means that all the caterpillars have been killed; 0% means that none of the caterpillars have been killed.

In this test, for example, the compound according to Preparation Example Ia-1 caused a destruction of 100% after 7 days at an active compound concentration of, for example 0.1%.

Example I

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are infested with larvae of the green rice leafhopper (*Nephotettix cincticeps*), as long as the seedlings are still moist.

After the specified period of time, the destruction in % is determined. 100% means that all the leafhoppers have been killed; 0% means that none of the leaf-hoppers have been killed.

In this test, for example, the compounds according to Preparation Examples Ia-1, Ia-2, Ib-1, Ib-2 and Ib-4 caused

We claim:
1. Compounds of the formula (I)

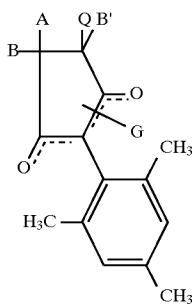

in which

A and Q together represent alkanediyl or alkenediyl, which is in each case optionally substituted by halogen, hydroxyl, mercapto or in each case optionally substituted alkyl, alkoxy, alkylthio, cycloalkyl, benzyloxy or aryl, and which furthermore optionally contains one of the following groups

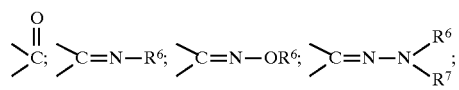

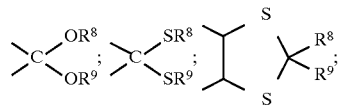

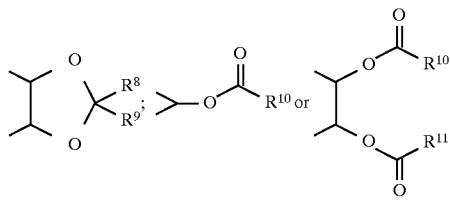

or is bridged by an alkanediyl group,

B and B' independently of one another represent hydrogen, halogen or alkyl, or together represent in each case optionally substituted alkanediyl or alkenediyl, G represents hydrogen (a), or represents one of the groups

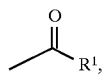 (b)

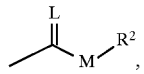 (c)

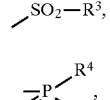 (d)

 (e)

E (f)

or

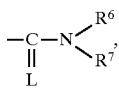 (g)

in which

E represents a metal ion equivalent or an ammonium ion,

L represents oxygen or sulphur and

M represents oxygen or sulphur, $R^1$ represents in each case optionally substituted alkyl, alkenyl, alkoxyalkyl, alkylthioalkyl, polyalkoxyalkyl or cycloalkyl, which can contain at least one heteroatom, or in each case optionally substituted phenyl, phenylalkyl, hetaryl, phenoxyalkyl or hetaryloxyalkyl, $R^2$ represents in each case optionally substituted alkyl, cycloalkyl, alkenyl, alkoxyalkyl or polyalkoxyalkyl, or in each case optionally substituted phenyl or benzyl, $R^3$ represents in each case optionally substituted alkyl, phenyl or phenylalkyl, $R^4$ and $R^5$ independently of one another represent in each case optionally halogen-substituted alkyl, alkoxy, alkylamino, dialkylamino, alkylthio, alkenylthio, cycloalkylthio, or represent in each case optionally substituted phenyl, phenoxy or phenylthio, $R^6$ represents hydrogen or in each case optionally halogen-substituted alkyl, alkenyl or alkoxyalkyl, or represents in each case optionally substituted cycloalkyl or phenyl, or represents optionally substituted benzyl, $R^7$ represents hydrogen or in each case optionally halogen-substituted alkyl or alkenyl, or $R^6$ and $R^7$, together with the N atom to which they are bonded, represent a ring which optionally contains oxygen or sulphur, $R^8$ and $R^9$ independently of one another represent hydrogen or in each case optionally substituted alkyl, phenyl or phenylalkyl, or together represent an optionally substituted alkanediyl radical and $R^{10}$ and $R^{11}$ independently of one another represent in each case optionally halogen-substituted alkyl, alkenyl, alkoxy, alkylamino, dialkylamino, alkenylamino or dialkenylamino or in each case optionally substituted phenyl or benzyl.

2. Compounds of the formula (I) according to claim 1 which, incorporating the various meanings (a), (b), (c), (d), (e), (f) and (g) of the group G, have the following structures (Ia) to (Ig):

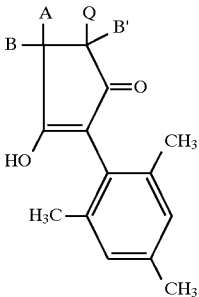

-continued

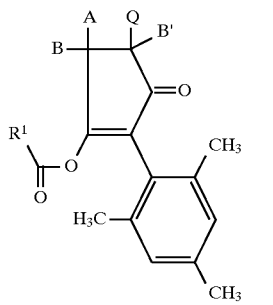 (Ib)

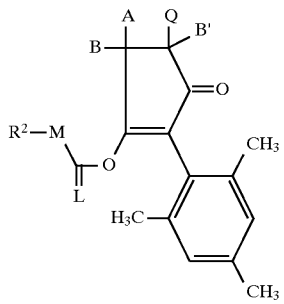 (Ic)

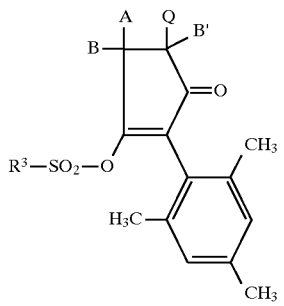 (Id)

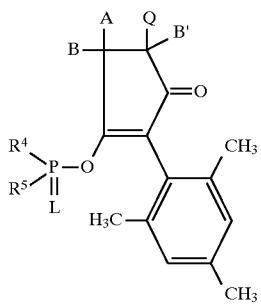 (Ie)

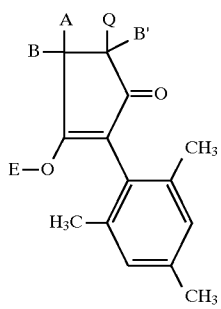 (If)

-continued

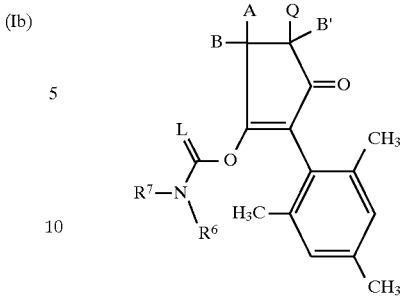 (Ig)

wherein

A, B, B', E, L, M, Q, $R^1$, $R^2$, $R^3$, $R^4$, $R^5$, $R^6$ and $R^7$ have the abovementioned meanings.

3. Compounds of the formula (I) according to claim 1, in which

A and Q together represent $C_1$–$C_6$-alkanediyl or $C_2$–$C_6$-alkenediyl, which is in each case optionally substituted once to three times in an identical or different manner by halogen, hydroxyl or mercapto, or by $C_1$–$C_{10}$-alkyl, $C_1$–$C_6$-alkoxy, $C_1$–$C_6$-alkylthio or $C_3$–$C_7$-cycloalkyl, in each case optionally halogen-substituted once to nine times in an identical or different manner, or by benzyloxy or phenyl, in each case optionally substituted once to five times in an identical or different manner by halogen, $C_1$–$C_6$-alkyl or $C_1$–$C_6$-alkoxy, and which furthermore optionally contains one of the following groupings

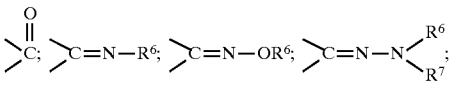

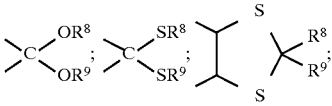

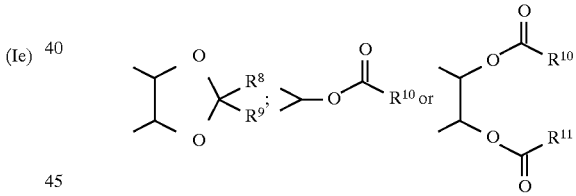

or is bridged by a $C_1$–$C_2$-alkanediyl group,

B and B' independently of one another represent hydrogen, halogen or $C_1$–$C_6$-alkyl, or together represent $C_1$–$C_6$-alkanediyl or $C_4$-alkenediyl, in each case optionally substituted by $C_1$–$C_6$-alkyl, G represents hydrogen (a), or represents one of the groups

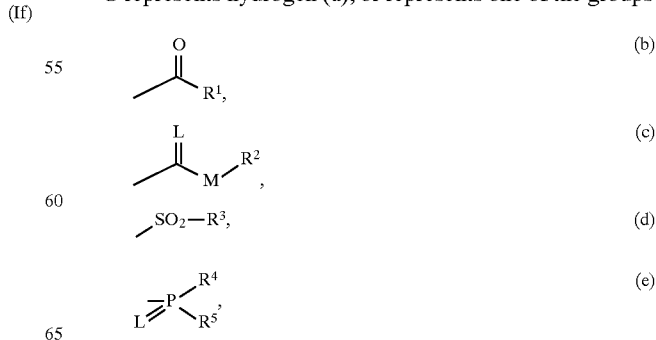

-continued

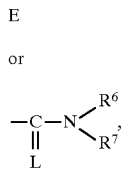

in which
E represents a metal ion equivalent or an ammonium ion,
L represents oxygen or sulphur and
M represents oxygen or sulphur, $R^1$ represents $C_1$–$C_{20}$-alkyl, $C_2$–$C_{10}$-alkenyl, $C_1$–$C_8$-alkoxy-$C_1$–$C_8$-alkyl, $C_1$–$C_8$-alkylthio-$C_1$–$C_8$-alkyl, or poly-$C_1$–$C_8$-alkoxy-$C_1$–$C_8$-alkyl, in each case optionally substituted once or several times in an identical or different manner by halogen, or represents cycloalkyl having 3 to 8 ring atoms, which is optionally substituted once or several times in an identical or different manner by halogen, $C_1$–$C_6$-alkyl or $C_1$–$C_6$-alkoxy and in which at least one methylene group can be replaced by an oxygen and/or sulphur atom, or represents phenyl which is optionally substituted once or several times in an identical or different manner by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents phenyl-$C_1$–$C_6$-alkyl which is optionally substituted once or several times in an identical or different manner by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which has 5 or 6 ring atoms and is optionally substituted once or several times in an identical or different manner by halogen or $C_1$–$C_6$-alkyl, or represents phenoxy-$C_1$–$C_6$-alkyl which is optionally substituted once or several times in an identical or different manner by halogen or $C_1$–$C_6$-alkyl, or represents hetaryloxy-$C_1$–$C_6$-alkyl which has 5 or 6 ring atoms and is optionally substituted once or several times in an identical or different manner by halogen, amino or $C_1$–$C_6$-alkyl, $R^2$ represents $C_1$–$C_{20}$-alkyl, $C_2$–$C_{10}$-alkenyl, $C_1$–$C_8$-alkoxy-$C_2$–$C_8$-alkyl, or poly-$C_1$–$C_8$-alkoxy-$C_2$–$C_8$-alkyl, in each case optionally substituted once or several times in an identical or different manner by halogen, or represents $C_3$–$C_6$-cycloalkyl which is optionally substituted once or several times in an identical or different manner by halogen, $C_1$–$C_6$-alkyl or $C_1$–$C_6$-alkoxy, or represents phenyl or benzyl, in each case optionally substituted once or several times in an identical or different manner by halogen, nitro, cyano, $C_1$–$C_6$-alkyl, $C_1$–$C_6$-alkoxy, $C_1$–$C_3$-halogenoalkoxy or $C_1$–$C_3$-halogenoalkyl, $R^3$ represents $C_1$–$C_{12}$-alkyl which is optionally substituted once or several times in an identical or different manner by halogen, or represents phenyl or phenyl-$C_1$–$C_4$-alkyl, in each case optionally substituted once or several times in an identical or different manner by halogen, $C_1$–$C_6$-alkyl, $C_1$–$C_6$-alkoxy, $C_1$–$C_3$-halogenoalkyl, $C_1$–$C_3$-halogenoalkoxy, cyano or nitro, $R^4$ and $R^5$ independently of one another represent $C_1$–$C_8$-alkyl, $C_1$–$C_8$-alkoxy, $C_1$–$C_8$-alkylamino, di-($C_1$–$C_8$-alkyl)-amino, $C_1$–$C_8$-alkylthio, $C_3$–$C_5$-alkenylthio, or $C_3$–$C_7$-cycloalkylthio, in each case optionally substituted once or several times in an identical or different manner by halogen, or represent phenyl, phenoxy or phenylthio, in each case optionally substituted once or several times in an identical or different manner by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ represents hydrogen or $C_1$–$C_{10}$-alkyl, $C_3$–$C_8$-alkenyl or $C_1$–$C_8$-alkoxy-$C_2$–$C_8$-alkyl, in each case optionally substituted once or several times in an identical or different manner by halogen, or represents $C_3$–$C_{10}$-cycloalkyl which is optionally substituted once or several times in an identical or different manner by halogen, $C_1$–$C_6$-alkyl, $C_1$–$C_6$-alkoxy, $C_1$–$C_3$-halogenoalkyl or $C_1$–$C_3$-halogenoalkoxy, or represents phenyl which is optionally substituted once or several times in an identical or different manner by halogen, $C_1$–$C_3$-halogenoalkyl, $C_1$–$C_8$-alkyl, $C_1$–$C_3$-halogenoalkoxy or $C_1$–$C_8$-alkoxy, or represents benzyl which is optionally substituted once or several times in an identical or different manner by halogen, $C_1$–$C_8$-alkyl, $C_1$–$C_3$-halogenoalkyl, $C_1$–$C_3$-halogenoalkoxy or $C_1$–$C_8$-alkoxy, $R^7$ represents hydrogen or $C_1$–$C_{10}$-alkyl or $C_3$–$C_{10}$-alkenyl, in each case optionally substituted once or several times in an identical or different manner by halogen, or $R^6$ and $R^7$, together with the N atom to which they are bonded, represent a 3- to 7-membered ring which optionally contains oxygen or sulphur, $R^8$ and $R^9$ independently of one another represent hydrogen or $C_1$–$C_6$-alkyl which is optionally substituted once or several times in an identical or different manner by halogen, or represent phenyl or phenyl-$C_1$–$C_4$-alkyl, in each case optionally substituted once or several times in an identical or different manner by halogen, $C_1$–$C_6$-alkyl, $C_1$–$C_6$-alkoxy, $C_1$–$C_6$-halogenoalkyl, $C_1$–$C_6$-halogenoalkoxy, nitro or cyano, or together represent $C_2$–$C_6$-alkanediyl which is optionally substituted once or several times in an identical or different manner by halogen, $C_1$–$C_6$-alkyl, $C_1$–$C_6$-alkoxy or $C_1$–$C_3$-halogenoalkyl and $R^{10}$ and $R^{11}$ independently of one another represent $C_1$–$C_{10}$-alkyl, $C_2$–$C_{10}$-alkenyl, $C_1$–$C_{10}$-alkoxy, $C_1$–$C_{10}$-alkylamino or di-($C_1$–$C_{10}$-alkyl)-amino, $C_3$–$C_{10}$-alkenylamino or di-($C_3$–$C_{10}$-alkenyl)-amino, in each case optionally substituted once or several times in an identical or different manner by halogen, or phenyl or benzyl, in each case substituted once or several times in an identical or different manner by halogen, $C_1$–$C_4$-alkyl, $C_1$–$C_4$-alkoxy, $C_1$–$C_4$-halogenoalkyl, nitro or cyano.

4. Compounds of the formula (I) according to claim 1, in which

A and Q together represent $C_1$–$C_5$-alkanediyl or $C_2$–$C_5$-alkenediyl, which is in each case optionally substituted once to three times in an identical or different manner by fluorine, chlorine, bromine, hydroxyl or mercapto, or by $C_1$–$C_8$-alkyl, $C_1$–$C_4$-alkoxy, $C_1$–$C_4$-alkylthio, $C_5$–$C_7$-cycloalkyl or phenyl, in each case optionally substituted once to five times in an identical or different manner by fluorine or chlorine, and which furthermore optionally contains one of the following groupings:

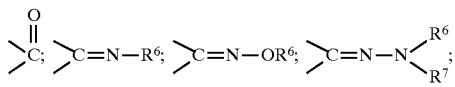
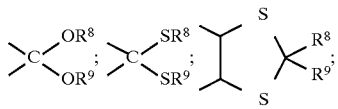
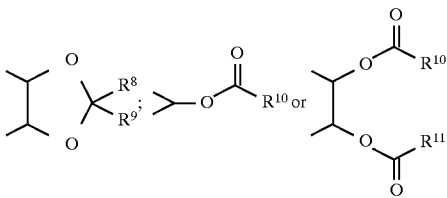

or is bridged by a $C_1$–$C_2$-alkanediyl group,

B and B' independently of one another represent hydrogen, fluorine, chlorine or $C_1$–$C_4$-alkyl, or together represent $C_1$–$C_5$-alkanediyl or $C_4$-alkenediyl, in each case optionally substituted by $C_1$–$C_4$-alkyl, G represents hydrogen (a) or represents one of the groups

 (b)

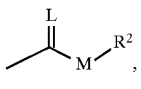 (c)

 (d)

 (e)

E (f)

or

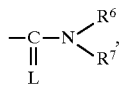 (g)

in which

E represents a metal ion equivalent or an ammonium ion,

L represents oxygen or sulphur and

M represents oxygen or sulphur, $R^1$ represents $C_1$–$C_{16}$-alkyl, $C_2$–$C_8$-alkenyl, $C_1$–$C_6$-alkoxy-$C_1$–$C_6$-alkyl, $C_1$–$C_6$-alkylthio-$C_1$–$C_6$-alkyl, or poly-$C_1$–$C_6$-alkoxy-$C_1$–$C_6$-alkyl, in each case optionally substituted once to nine times in an identical or different manner by fluorine or chlorine, or represents cycloalkyl which has 3 to 7 ring atoms and is optionally substituted once to three times in an identical or different manner by fluorine, chlorine, $C_1$–$C_4$-alkyl or $C_1$–$C_4$-alkoxy, and in which one or two methylene groups can be replaced by oxygen and/or sulphur atoms, or represents phenyl which is optionally substituted once to three times in an identical or different manner by fluorine, chlorine, bromine, cyano, nitro, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted once to three times in an identical or different manner by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents furanyl, thienyl, pyridyl, pyrimidyl, thiazolyl or pyrazolyl, in each case optionally substituted once or twice in an identical or different manner by fluorine, chlorine, bromine or $C_1$–$C_4$-alkyl, or represents phenoxy-$C_1$–$C_5$-alkyl which is optionally substituted once to three times in an identical or different manner by fluorine, chlorine or $C_1$–$C_4$-alkyl, or represents pyridyloxy-$C_1$–$C_6$-alkyl, pyrimidinyloxy-$C_1$–$C_6$-alkyl or thiazolyloxy-$C_1$–$C_6$-alkyl, in each case optionally substituted once or twice in an identical or different manner by fluorine, chlorine, amino or $C_1$–$C_4$-alkyl, $R^2$ represents $C_1$–$C_{16}$-alkyl, $C_2$–$C_8$-alkenyl, $C_1$–$C_6$-alkoxy-$C_2$–$C_6$-alkyl, or poly-$C_1$–$C_6$-alkoxy-$C_2$–$C_6$-alkyl, in each case optionally substituted once to nine times in an identical or different manner by fluorine or chlorine, or represents $C_3$–$C_6$-cycloalkyl which is optionally substituted once to five times in an identical or different manner by fluorine, chlorine, $C_1$–$C_4$-alkyl or $C_1$–$C_4$-alkoxy, or represents phenyl or benzyl, in each case optionally substituted once to three times in an identical or different manner by fluorine, chlorine, bromine, nitro, cyano, $C_1$–$C_4$-alkyl, $C_1$–$C_4$-alkoxy, $C_1$–$C_2$-halogenoalkoxy or $C_1$–$C_2$-halogenoalkyl, $R^3$ represents $C_1$–$C_9$-alkyl which is optionally substituted once to five times in an identical or different manner by fluorine or chlorine, or represents phenyl or phenyl-$C_1$–$C_2$-alkyl, in each case optionally substituted once to three times in an identical or different manner by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, $R^4$ and $R^5$ independently of one another represent $C_1$–$C_6$-alkyl, $C_1$–$C_6$-alkoxy, $C_1$–$C_6$-alkylamino, di-($C_1$–$C_6$-alkyl)-amino, $C_1$–$C_6$-alkylthio, $C_3$–$C_4$-alkenylthio, or $C_3$–$C_6$-cycloalkylthio, optionally substituted once to five times in an identical or different manner by fluorine or chlorine, or represent phenyl, phenoxy or phenylthio, in each case optionally substituted once to three times in an identical or different manner by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ represents hydrogen or $C_1$–$C_8$-alkyl, $C_3$–$C_6$-alkenyl or $C_1$–$C_6$-alkoxy-$C_2$–$C_6$-alkyl, in each case optionally substituted once to five times in an identical or different manner by fluorine or chlorine, or represents $C_3$–$C_8$-cycloalkyl which is in each case optionally substituted once to three times in an identical or different manner by fluorine, chlorine, $C_1$–$C_4$-alkyl, $C_1$–$C_4$-alkoxy, $C_1$–$C_2$-halogenoalkyl or $C_1$–$C_2$-halogenoalkoxy, or represents phenyl which is optionally substituted once to three times in an identical or different manner by fluorine, chlorine, bromine, $C_1$–$C_2$-halogenoalkyl, $C_1$–$C_5$-alkyl, $C_1$–$C_2$-halogenoalkoxy or $C_1$–$C_5$-alkoxy, or represents benzyl which is optionally substituted once to three times in an identical or different manner by fluorine, chlorine, bromine, $C_1$–$C_5$-alkyl, $C_1$–$C_2$-halogenoalkyl, $C_1$–$C_2$-halogenoalkoxy or $C_1$–$C_5$-alkoxy, $R^7$ represents hydrogen or $C_1$–$C_8$-alkyl or $C_3$–$C_8$-alkenyl, in each case optionally substituted once to five times in an identical or different manner by fluorine or chlorine, or $R^6$ and $R^7$, together with the N atom to which they are bonded, represent a 4- to 7-membered ring which optionally contains oxygen or sulphur, $R^8$ and $R^9$ independently of one another represent hydrogen or $C_1$–$C_4$-alkyl which is optionally substituted once to five times in an identical or different manner by fluorine or chlorine, or represent phenyl which is optionally substituted once to three times in an identical or different manner by fluorine, chlorine, $C_1$–$C_4$-alkyl, $C_1$–$C_4$-alkoxy, $C_1$–$C_2$-halogenoalkyl, $C_1$–$C_2$-halogenoalkoxy, nitro or cyano, or together represent $C_2$–$C_5$-alkanediyl which is optionally substituted once to three times in an identical or different manner by fluorine, chlorine, $C_1$–$C_4$-alkyl, $C_1$–$C_4$-alkoxy or $C_1$–$C_2$-halogenoalkyl and $R^{10}$ and $R^{11}$ independently of one another represent $C_1$–$C_8$-alkyl, $C_2$–$C_8$-alkenyl, $C_1$–$C_8$-alkoxy, $C_1$–$C_8$-alkylamino, $C_3$–$C_8$-alkenylamino, di-($C_1$–$C_8$-alkyl)-amino or di-($C_3$–$C_8$-alkenyl)-amino, in each case optionally substituted once to five times in an identical or different manner by fluorine or chlorine.

5. Compounds of the formula (I) according to claim 1, in which

A and Q together represent $C_1$–$C_4$-alkanediyl or $C_2$–$C_4$-alkenediyl, which is in each case optionally substituted once or twice in an identical or different manner by fluorine, chlorine, hydroxyl or mercapto, or by $C_1$–$C_6$-alkyl, $C_1$–$C_2$-alkoxy, $C_1$–$C_2$-alkylthio, $C_5$–$C_6$-cycloalkyl or phenyl, in each case optionally substituted once to three times in an identical or different manner by fluorine or chlorine, and which furthermore optionally contains one of the following groupings:

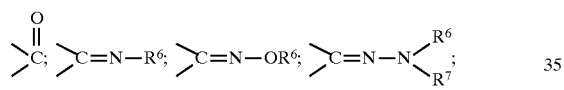

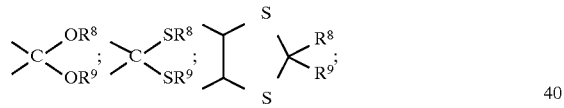

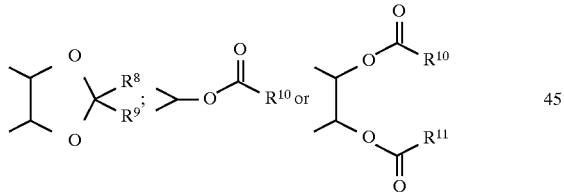

or is bridged by a $C_1$–$C_2$-alkanediyl group,

B and B' independently of one another represent hydrogen, fluorine, chlorine, methyl or ethyl, or together represent $C_1$–$C_4$-alkanediyl or $C_4$-alkenediyl, in each case optionally substituted by methyl or ethyl, G represents hydrogen (a) or represents one of the groups

 (b)

 (c)

 (d)

 (e)

E (f)

or

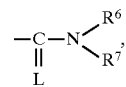 (g)

in which

E represents a metal ion equivalent or an ammonium ion,

L represents oxygen or sulphur and

M represents oxygen or sulphur, $R^1$ represents $C_1$–$C_{14}$-alkyl, $C_2$–$C_6$-alkenyl, $C_1$–$C_4$-alkoxy-$C_1$–$C_6$-alkyl, $C_1$–$C_4$-alkylthio-$C_1$–$C_6$-alkyl, or poly-$C_1$–$C_4$-alkoxy-$C_1$–$C_4$-alkyl, in each case optionally substituted once to five times in an identical or different manner by fluorine or chlorine, or represents cycloalkyl which has 3 to 6 ring atoms and is optionally substituted once or twice in an identical or different manner by fluorine, chlorine, methyl, ethyl, methoxy or ethoxy, and in which one or two methylene groups can be replaced by oxygen and/or sulphur atoms, or represents phenyl which is optionally substituted once or twice in an identical or different manner by fluorine, chlorine, bromine, methyl, ethyl, propyl, i-propyl, methoxy, ethoxy, trifluoromethyl, trifluoromethoxy, cyano or nitro, or represents benzyl which is optionally substituted once or twice in an identical or different manner by fluorine, chlorine, bromine, methyl, ethyl, propyl, i-propyl, methoxy, ethoxy, trifluoromethyl or trifluoromethoxy, or represents thienyl, furanyl or pyridyl, in each case optionally substituted once or twice in an identical or different manner by fluorine, chlorine, bromine, methyl or ethyl, or represents phenoxy-$C_1$–$C_4$-alkyl which is optionally substituted once or twice in an identical or different manner by fluorine, chlorine, methyl or ethyl, or represents pyridyloxy-$C_1$–$C_4$-alkyl, pyrimidyloxy-$C_1$–$C_4$-alkyl or thiazolyloxy-$C_1$–$C_4$-alkyl, in each case optionally substituted once or twice in an identical or different manner by fluorine, chlorine, amino, methyl or ethyl, $R^2$ represents $C_1$–$C_{14}$-alkyl, $C_2$–$C_6$-alkenyl, $C_1$–$C_4$-alkoxy-$C_2$–$C_6$-alkyl, or poly-$C_1$–$C_4$-alkoxy-$C_2$–$C_6$-alkyl, in each case optionally substituted once to five times in an identical or different manner by fluorine or chlorine, or represents $C_3$–$C_6$-cycloalkyl which is optionally substituted once to three times in an identical or different manner by fluorine, chlorine, methyl, ethyl, methoxy or ethoxy, or represents phenyl or benzyl, in each case optionally substituted once or twice in an identical or different manner by fluorine, chlorine, nitro, cyano, methyl, ethyl, propyl, i-propyl, methoxy, ethoxy, trifluoromethoxy or trifluoromethyl, $R^3$ represents $C_1$–$C_6$-alkyl which is optionally substituted once to three times in an identical or different manner by fluorine or chlorine, or represents phenyl or benzyl, in each case optionally substituted once or twice by fluorine, chlorine, bromine, methyl, ethyl, methoxy, ethoxy, trifluoromethyl, trifluoromethoxy, cyano or nitro, $R^4$ and $R^5$ independently of one another represent $C_1$–$C_4$-alkyl, $C_1$–$C_4$-alkoxy, $C_1$–$C_4$-alkylamino, di-($C_1$–$C_4$- alkyl)-amino, $C_1$–$C_4$-alkylthio, in each case optionally substituted once to three times in an identical or different manner by fluorine or chlorine, or represent phenyl, phenoxy or phenylthio, in each case optionally substituted once or twice in an identical or different manner by fluorine, chlorine, bromine, nitro, cyano, $C_1$–$C_2$-alkoxy, trifluoromethoxy, $C_1$–$C_2$-alkylthio, trifluoromethyl or $C_1$–$C_3$-alkyl, $R^6$ represents hydrogen or $C_1$–$C_6$-alkyl or $C_1$–$C_6$-alkoxy-$C_2$–$C_4$-alkyl, in each case optionally substituted once to three times in an identical or different manner by fluorine or chlorine, or represents $C_3$–$C_6$-cycloalkyl which is optionally substituted once or twice in an identical or different manner by fluorine, chlorine, methyl, methoxy, trifluoromethyl or trifluoromethoxy, or represents phenyl which is optionally substituted once or twice in an identical or different manner by fluorine, chlorine, trifluoromethyl, $C_1$–$C_4$-alkyl, trifluoromethoxy or $C_1$–$C_4$-alkoxy, or represents benzyl which is optionally substituted once or twice in an identical or different manner by fluorine, chlorine, $C_1$–$C_4$-alkyl, trifluoromethyl, trifluoromethoxy or $C_1$–$C_4$-alkoxy, $R^7$ represents hydrogen or $C_1$–$C_6$-alkyl or $C_3$–$C_6$-alkenyl, in each case optionally substituted once to three times in an identical or different manner by fluorine or chlorine, or $R^6$ and $R^7$, together with the N atom to which they are bonded, a 5- to 7-membered ring which optionally contains oxygen or sulphur, $R^8$ and $R^9$ independently of one another represent hydrogen or $C_1$–$C_4$-alkyl which is optionally substituted once to three times in an identical or different manner by fluorine or chlorine, or represent phenyl which is optionally substituted once or twice in an identical or different manner by fluorine, chlorine, methyl, ethyl, methoxy, ethoxy, trifluoromethyl, trifluoromethoxy, nitro or cyano, or together represent $C_2$–$C_5$-alkanediyl which is optionally substituted once or twice in an identical or different manner by fluorine, chlorine, methyl, ethyl, methoxy, ethoxy or trifluoromethyl and $R^{10}$ and $R^{11}$ independently of one another represent $C_1$–$C_6$-alkyl or $C_2$–$C_6$-alkenyl.

6. Process for the preparation of compounds of the formula (I) according to claim 1, characterized in that to prepare (A) compounds of the formula (Ia)

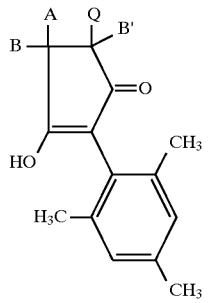
(Ia)

in which

A, B, B' and Q have the meaning given in claim 1, compounds of the formula (II)

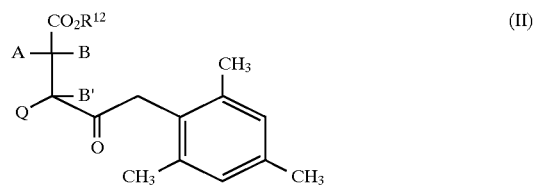
(II)

in which

A, B, B' and Q have the abovementioned meaning and $R^{12}$ represents alkyl, are subjected to an intramolecular condensation reaction in the presence of a diluent and in the presence of a base; or (B) of the formula (Ib)

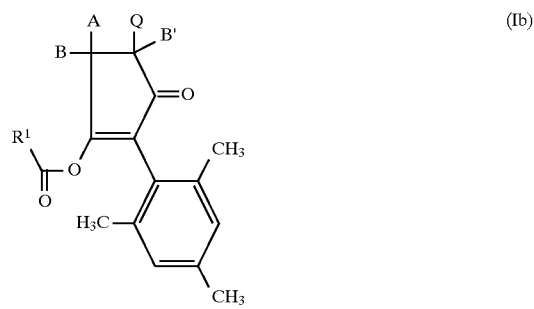
(Ib)

in which

A, B, B', Q and $R^1$ have the meaning given in claim 1, compounds of the formula (Ia)

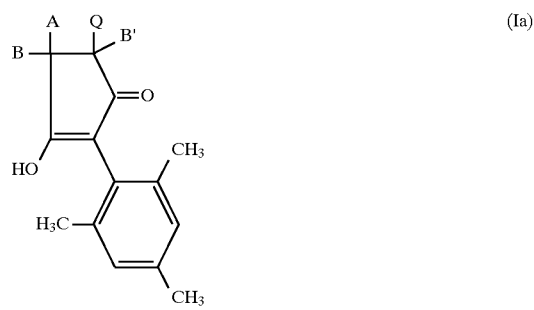
(Ia)

in which

A, B, B' and Q have the abovementioned meaning,

α) are reacted with acid halides of the formula (III)

(III)

in which $R^1$ has the abovementioned meaning and

Hal represents halogen, if appropriate in the presence of a diluent and if appropriate in the presence of an acid-binding agent, or β) are reacted with carboxylic acid anhydrides of the formula (IV)

$R^1$—CO—O—CO—$R^1$ (IV)

in which $R^1$ has the abovementioned meaning, if appropriate in the presence of a diluent and if appropriate in the presence of an acid-binding agent; or (C) of the formula (Ic-1)

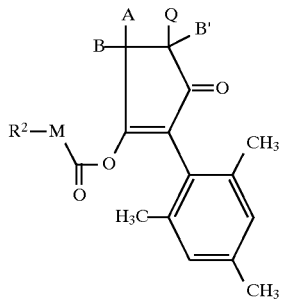
(Ic-1)

in which

A, B, B', Q and $R^2$ have the meaning given in claim 1, and

M represents oxygen or sulphur, compounds of the formula (Ia)

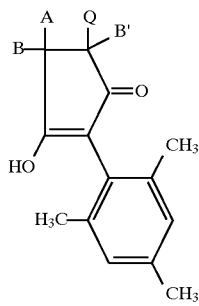
(Ia)

in which

A, B, B' and Q have the abovementioned meaning, are reacted with chloroformic acid esters or chloroformic acid thiolesters of the formula (V)

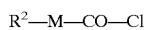
$R^2$—M—CO—Cl   (V)

in which $R^2$ and M have the abovementioned meaning, if appropriate in the presence of a diluent and if appropriate in the presence of an acid-binding agent; or (D) of the formula (Ic-2)

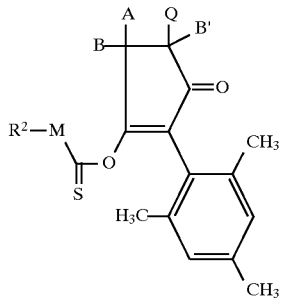
(Ic-2)

in which

A, B, B', Q and $R^2$ have the abovementioned meaning and

M represents oxygen or sulphur, compounds of the formula (Ia)

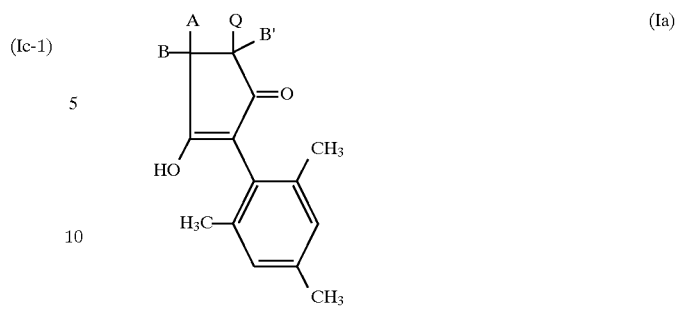
(Ia)

in which

A, B, B' and Q have the abovementioned meaning,

α) are reacted with chloromonothioformic acid esters or chlorodithioformic acid esters of the formula (VI)

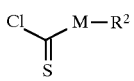
(VI)

in which

M and $R^2$ have the abovementioned meaning, if appropriate in the presence of a diluent and if appropriate in the presence of an acid-binding agent, or β) are reacted with carbon disulphide and then with alkyl halides of the general formula (VII)

$R^2$-Hal   (VII)

in which $R^2$ has the abovementioned meaning and

Hal represents chlorine, bromine or iodine, if appropriate in the presence of a diluent and if appropriate in the presence of a base; or (E) of the formula (Id)

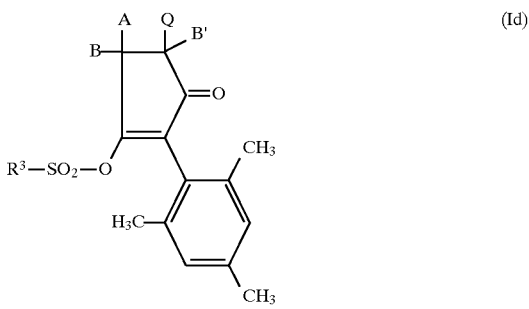
(Id)

in which

A, B, B', Q and $R^3$ have the meaning given in claim 1, compounds of the formula (Ia)

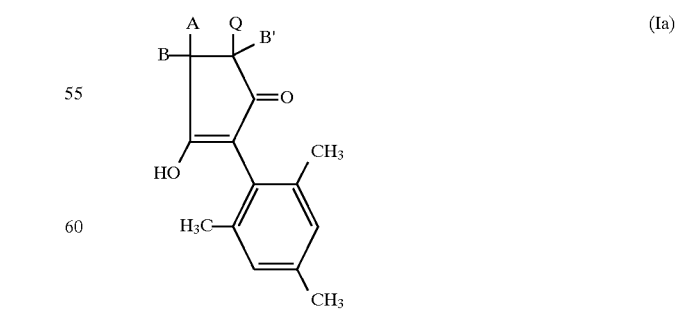
(Ia)

in which

A, B, B' and Q have the abovementioned meaning, are reacted with sulphonic acid chlorides of the formula (VIII)

$R^3$—$SO_2$—Cl (VIII)

in which
$R^3$ has the abovementioned meaning,
if appropriate in the presence of a diluent and if appropriate in the presence of an acid-binding agent; or (F) of the formula (Ie)

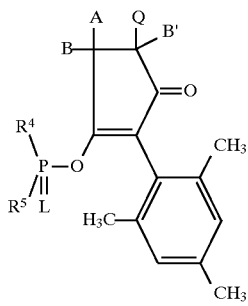
(Ie)

in which
A, B, L, B', Q, $R^4$ and $R^5$ have the meaning given in claim 1, compounds of the formula (Ia) or enols thereof

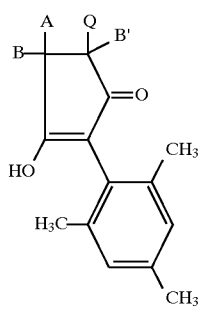
(Ia)

in which
A, B, B' and Q have the abovementioned meaning, are reacted with phosphorus compounds of the formula (IX)

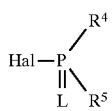
(IX)

in which
L, $R^4$ and $R^5$ have the abovementioned meaning and
Hal represents halogen
if appropriate in the presence of a diluent and if appropriate in the presence of an acid-binding agent; or (G) of the formula (If)

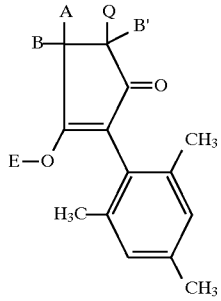
(If)

in which
A, B, B' and Q have the abovementioned meaning and

E represents a metal ion equivalent, or represents an ammonium ion, compounds of the formula (Ia)

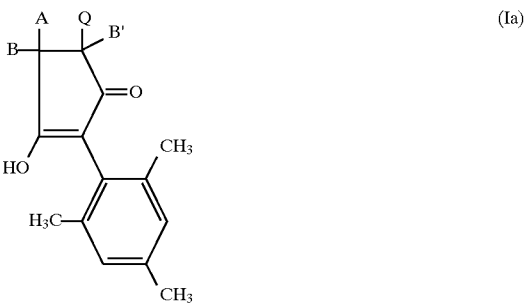
(Ia)

in which
A, B, B' and Q have the abovementioned meaning, are reacted with metal compounds or amines of the formulae (X) and (XI)

(X)
(XI)

in which
Me represents mono- or divalent metal ions,
t represents the number 1 or 2,
$R^{13}$, $R^{14}$ and $R^{15}$, independently of one another, represent hydrogen or alkyl and
$R^{16}$ represents hydrogen, hydroxyl or $C_1$–$C_4$-alkoxy,
if appropriate in the presence of a diluent, or (H) of the formula (Ig)

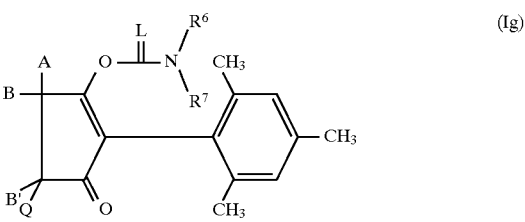
(Ig)

in which
A, B, L, B', Q, $R^6$ and $R^7$ have the meaning given in claim 1, compounds of the formula (Ia)

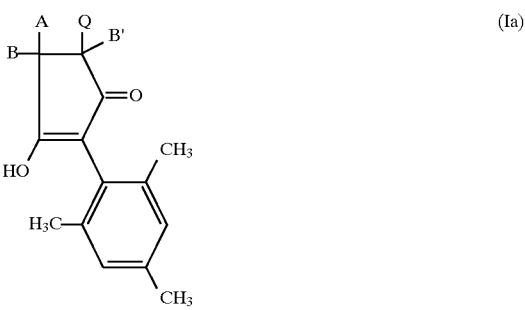
(Ia)

in which
A, B, B' and Q have the abovementioned meaning, are reacted

α) with compounds of the formula (XII)

$$R^6—N=C=L \quad (XII)$$

in which

L and $R^6$ have the abovementioned meaning, if appropriate in the presence of a diluent and if appropriate in the presence of a catalyst, or β) with carbamic acid chlorides or thiocarbamic acid chlorides of the formula (XIII)

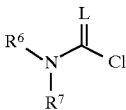

(XIII)

in which

L, $R^6$ and $R^7$ have the abovementioned meaning, if appropriate in the presence of a diluent and if appropriate in the presence of an acid-binding agent.

* * * * *

UNITED STATES PATENT AND TRADEMARK OFFICE
CERTIFICATE OF CORRECTION

PATENT NO : 5, 808, 135
DATED : September 15, 1998
INVENTOR(S) : Fischer, et al.

It is certified that error appears in the above-identified patent and that said Letters Patent are hereby corrected as shown below:

Title Page [30] "Foreign Application Priority Data"   Delete " 195 92 945.3 " and substitute --- 195 02 945.3 ---

Signed and Sealed this

Twenty-seventh Day of July, 1999

*Attest:*

Q. TODD DICKINSON

*Attesting Officer*   *Acting Commissioner of Patents and Trademarks*